US010544397B2

(12) United States Patent
Howley et al.

(10) Patent No.: US 10,544,397 B2
(45) Date of Patent: Jan. 28, 2020

(54) VIRAL VECTOR MANUFACTURE

(71) Applicant: Sementis Limited, Victoria (AU)

(72) Inventors: Paul Michael Howley, Victoria (AU); Liang Liu, South Australia (AU)

(73) Assignee: SEMENTIS LIMITED, Berwick, Victoria (AU)

( * ) Notice: Subject to any disclaimer, the term of this patent is extended or adjusted under 35 U.S.C. 154(b) by 416 days.

(21) Appl. No.: 15/033,541

(22) PCT Filed: Nov. 3, 2014

(86) PCT No.: PCT/AU2014/050330

§ 371 (c)(1),
(2) Date: Apr. 29, 2016

(87) PCT Pub. No.: WO2015/061858

PCT Pub. Date: May 7, 2015

(65) Prior Publication Data

US 2017/0029784 A1 Feb. 2, 2017

(30) Foreign Application Priority Data

Nov. 1, 2013 (AU) ................................ 2013904242
Feb. 7, 2014 (AU) ................................ 2014900370

(51) Int. Cl.
*C12N 7/00* (2006.01)
*C12N 15/86* (2006.01)

(52) U.S. Cl.
CPC ............... *C12N 7/00* (2013.01); *C12N 15/86* (2013.01); *C12N 2710/24122* (2013.01); *C12N 2710/24143* (2013.01); *C12N 2710/24152* (2013.01)

(58) Field of Classification Search
None
See application file for complete search history.

(56) References Cited

U.S. PATENT DOCUMENTS 5,766,882 A * 6/1998 Falkner ................ C07K 14/005 435/320.1
5,830,688 A 11/1998 Drillien et al.
7,473,536 B2 * 1/2009 Howley ............... C07K 14/005 424/199.1

FOREIGN PATENT DOCUMENTS

JP S63-157988 A 6/1988
JP H09-512707 A 12/1997
WO 1995/030018 A2 11/1995

OTHER PUBLICATIONS

Schuenadel et al., Generation and characterization of a Cowpox virus mutant lacking host range factor CP77, 2012, Virus Research , vol. 168, pp. 23-32.*
Extended European Search Report dated Mar. 14, 2017 issued in European Patent Application No. 14858802.3.
Y. Zhang, et al., "Immature Viral Envelope Formation is Interrupted at the Same Stage by lac Operator-Mediated Repression of the Vaccinia Virus D13L Gene and by the Drug Rifampicin," Virology, No. 187, 1992, pp. 643-653.
K. A. Bratke, et al., "A survey of host range genes in poxvirus genomes," Infection, Genetics and Evolution, No. 14, 2013, pp. 406-425.
A. L. Ramsey-Ewing, et al., "Complementation of a Vaccinia Virus Host-Range K1L Gene Deletion by the Nonhomologous CP77 Gene," Virology, No. 222, 1996, pp. 75-86.
Japanese Office Action dated Jul. 31, 2018 issued in Japanese Patent Application No. 2016-550897 (with English translation).
G. Sutter, et al., "Stable Expression of the Vaccinia Virus K1L Gene in Rabbit Cells Complements the Host Range Defect of a Vaccinia Virus Mutant," Journal of Virology, Jul. 1994, vol. 68, No. 7, pp. 4109-4116.
Livia Schuenadel, et al., "Generation and characterization of a Cowpox virus mutant lacking host range factor CP77," Virus Research, vol. 168, 2012, pp. 27-32.
Yan-min Zhang, et al., "Establishment of BHK 21 Cell Line Stably Expressing Vaccinia Virus D13L Gene," Journal of Tropical Medicine, vol. 4, No. 3, Jun. 2004, pp. 2-8.
pmCherry-N1 Vector Information, Protocol No. PT3974-5, Catalog No. 632523, Clontech Laboratories, Inc., Sep. 2, 2008 www.takarabio.com/assets/documents/Vector%20Documents/pmCherry-N1%20Vector%20Information.pdf.
pEGFP-C2 Vector Information, Protocol No. PT3051-5, Catalog No. 6083-1, Clontech Laboratories, Inc., 1997 www.yrgene.com/documents/vector/pegfp-c2mapmcs.pdf.
Office Action issued in corresponding Japanese Application No. 2016-550897, dated Jun. 18, 2019.

* cited by examiner

*Primary Examiner* — Benjamin P Blumel
(74) *Attorney, Agent, or Firm* — McDermott Will & Emery LLP

(57) ABSTRACT

This present invention relates to a modified mammalian cell in which the genome of the cell is modified to comprise a sequence encoding CP77 under the control of a promoter such that the modified cell line sustains propagation of a poxvirus that is less able or unable to propagate in the unmodified cell.

9 Claims, No Drawings

Specification includes a Sequence Listing.

SEQUENCE LISTING

```
<160> NUMBER OF SEQ ID NOS: 23

<210> SEQ ID NO 1
<211> LENGTH: 2031
<212> TYPE: DNA
<213> ORGANISM: Artificial Sequence
<220> FEATURE:
<223> OTHER INFORMATION: Description of Artificial Sequence: Synthetic
      Nucleotide sequence of CP77 codon optimised for expression
      in mammalian cells (CHO)

<400> SEQUENCE: 1

atgttcgact acctggaaaa tgaggaagtg gccctggacg agctgaagca gatgctgcgg     60

gaccgggacc ccaacgacac ccggaaccag ttcaagaaca acgccctgca cgcctacctg    120

tttaacgagc actgcaacaa cgtggaagtg gtcaagctgc tgctggactc cggcaccaac    180

cccctgcaca agaactggcg gcagctgacc cccctgggcg agtacaccaa ctcccggcac    240

ggcaaagtga acaaggatat cgccatggtg ctgctggaag ctaccggcta ctccaacatc    300

aacgacttca acatcttcac ctacatgaag tccaagaacg tggacatcga cctgatcaag    360

gtgctggtgg aacacggctt cgacttctcc gtgaagtgcg agaagcacca ctccgtgatc    420

gagaactacg tgatgaccga cgaccccgtg cctgagatca tcgacctgtt catcgagaac    480

ggctgctccg tgatctacga ggacgaggac gacgagtacg gctacgccta cgaggaatac    540

cactcccaga acgacgacta ccagccccgg aactgcggca ccgtgctgca cctgtacatc    600

atctcccacc tgtactccga gagcgactcc cggtcttgcg tgaaccccga ggtggtcaag    660

tgcctgatca accacggcat caacccctcc agcatcgata agaactactg caccgccctg    720
```

-continued

```
cagtactaca tcaagtcctc ccacatcgac atcgatatcg tgaagctgct gatgaagggc    780

atcgacaaca ccgcctacag ctacatcgac gacctgacct gctgcacccg gggcatcatg    840

gccgactacc tgaacagcga ctaccggtac aacaaggacg tggacctgga tctggtcaaa    900

ctgttcctgg aaaacggcaa gcctcacggc atcatgtgct ccatcgtgcc cctgtggcgg    960

aacgacaaag agacaatctc cctgatcctg aaaaccatga actccgacgt gctgcagcat   1020

atcctgatcg agtacatcac cttctccgat atcgacatct ctctggtcga gtacatgctg   1080

gaatacggcg ctgtggtcaa caaagaggcc atccacggct acttcaagaa catcaacatc   1140

gactcctaca ccatgaagta cctgctgaaa aaagagggcg gcgacgccgt caaccacctg   1200

gacgacggcg agatccccat cggccacctg tgcaagagca actacggccg gtacaacttt   1260

tacaccgaca cctaccggca gggcttccgg gacatgtcct acgcctgccc catcctgtcc   1320

accatcaaca tctgcctgcc ctacctgaag gacatcaata tgatcgataa gcggggcgag   1380

acactgctgc acaaggccgt gcgctacaac aagcagtccc tggtgtccct gctgctggaa   1440

agcggctccg acgtgaacat ccggtccaac aacggctaca cctgtatcgc tatcgccatc   1500

aacgagtccc ggaacatcga gctgctgaat atgctgctgt gccacaagcc taccctggac   1560

tgcgtgatcg actccctgcg cgagatcagc aacatcgtgg acaacgccta cgccatcaag   1620

cagtgcatca gatacgccat gattatcgac gactgcatct cctccaagat ccccgagtcc   1680

atctccaagc actacaacga ctacattgac atctgcaacc aggaactgaa cgagatgaag   1740

aaaatcatcg tgggcggcaa caccatgttc agcctgatct tcaccgatca cggcgccaag   1800

atcatccacc gctacgccaa caaccccgag ctgcgggcct actacgagtc caagcagaac   1860

aagatctacg tcgaggtcta cgacatcatc agcaacgcca tcgtgaagca caacaagatt   1920

cacaagaaca tcgagtccgt ggacgacaac acctacatct ccaacctgcc ctataccatc   1980

aagtacaaga tcttcgagca gcaggattac aaggatgacg atgacaagtg a            2031
```

<210> SEQ ID NO 2
<211> LENGTH: 676
<212> TYPE: PRT
<213> ORGANISM: Artificial Sequence
<220> FEATURE:
<223> OTHER INFORMATION: Description of Artificial Sequence: Synthetic
      Amino acid sequence of CP77 encoded by SEQ ID NO: 1

<400> SEQUENCE: 2

```
Met Phe Asp Tyr Leu Glu Asn Glu Glu Val Ala Leu Asp Glu Leu Lys
1               5                   10                  15

Gln Met Leu Arg Asp Arg Asp Pro Asn Asp Thr Arg Asn Gln Phe Lys
            20                  25                  30

Asn Asn Ala Leu His Ala Tyr Leu Phe Asn Glu His Cys Asn Asn Val
        35                  40                  45

Glu Val Val Lys Leu Leu Leu Asp Ser Gly Thr Asn Pro Leu His Lys
    50                  55                  60

Asn Trp Arg Gln Leu Thr Pro Leu Gly Glu Tyr Thr Asn Ser Arg His
65                  70                  75                  80

Gly Lys Val Asn Lys Asp Ile Ala Met Val Leu Leu Glu Ala Thr Gly
                85                  90                  95

Tyr Ser Asn Ile Asn Asp Phe Asn Ile Phe Thr Tyr Met Lys Ser Lys
            100                 105                 110

Asn Val Asp Ile Asp Leu Ile Lys Val Leu Val Glu His Gly Phe Asp
        115                 120                 125
```

-continued

```
Phe Ser Val Lys Cys Glu Lys His His Ser Val Ile Glu Asn Tyr Val
    130                 135                 140

Met Thr Asp Asp Pro Val Pro Glu Ile Ile Asp Leu Phe Ile Glu Asn
145                 150                 155                 160

Gly Cys Ser Val Ile Tyr Glu Asp Glu Asp Asp Glu Tyr Gly Tyr Ala
                165                 170                 175

Tyr Glu Glu Tyr His Ser Gln Asn Asp Asp Tyr Gln Pro Arg Asn Cys
            180                 185                 190

Gly Thr Val Leu His Leu Tyr Ile Ile Ser His Leu Tyr Ser Glu Ser
        195                 200                 205

Asp Ser Arg Ser Cys Val Asn Pro Glu Val Val Lys Cys Leu Ile Asn
    210                 215                 220

His Gly Ile Asn Pro Ser Ser Ile Asp Lys Asn Tyr Cys Thr Ala Leu
225                 230                 235                 240

Gln Tyr Tyr Ile Lys Ser Ser His Ile Asp Ile Asp Ile Val Lys Leu
                245                 250                 255

Leu Met Lys Gly Ile Asp Asn Thr Ala Tyr Ser Tyr Ile Asp Asp Leu
            260                 265                 270

Thr Cys Cys Thr Arg Gly Ile Met Ala Asp Tyr Leu Asn Ser Asp Tyr
        275                 280                 285

Arg Tyr Asn Lys Asp Val Asp Leu Asp Leu Val Lys Leu Phe Leu Glu
    290                 295                 300

Asn Gly Lys Pro His Gly Ile Met Cys Ser Ile Val Pro Leu Trp Arg
305                 310                 315                 320

Asn Asp Lys Glu Thr Ile Ser Leu Ile Leu Lys Thr Met Asn Ser Asp
                325                 330                 335

Val Leu Gln His Ile Leu Ile Glu Tyr Ile Thr Phe Ser Asp Ile Asp
            340                 345                 350

Ile Ser Leu Val Glu Tyr Met Leu Glu Tyr Gly Ala Val Val Asn Lys
        355                 360                 365

Glu Ala Ile His Gly Tyr Phe Lys Asn Ile Asn Ile Asp Ser Tyr Thr
    370                 375                 380

Met Lys Tyr Leu Leu Lys Lys Glu Gly Gly Asp Ala Val Asn His Leu
385                 390                 395                 400

Asp Asp Gly Glu Ile Pro Ile Gly His Leu Cys Lys Ser Asn Tyr Gly
                405                 410                 415

Arg Tyr Asn Phe Tyr Thr Asp Thr Tyr Arg Gln Gly Phe Arg Asp Met
            420                 425                 430

Ser Tyr Ala Cys Pro Ile Leu Ser Thr Ile Asn Ile Cys Leu Pro Tyr
        435                 440                 445

Leu Lys Asp Ile Asn Met Ile Asp Lys Arg Gly Glu Thr Leu Leu His
    450                 455                 460

Lys Ala Val Arg Tyr Asn Lys Gln Ser Leu Val Ser Leu Leu Leu Glu
465                 470                 475                 480

Ser Gly Ser Asp Val Asn Ile Arg Ser Asn Asn Gly Tyr Thr Cys Ile
                485                 490                 495

Ala Ile Ala Ile Asn Glu Ser Arg Asn Ile Glu Leu Leu Asn Met Leu
            500                 505                 510

Leu Cys His Lys Pro Thr Leu Asp Cys Val Ile Asp Ser Leu Arg Glu
        515                 520                 525

Ile Ser Asn Ile Val Asp Asn Ala Tyr Ala Ile Lys Gln Cys Ile Arg
    530                 535                 540

Tyr Ala Met Ile Ile Asp Asp Cys Ile Ser Ser Lys Ile Pro Glu Ser
```

-continued

```
545                 550                 555                 560

Ile Ser Lys His Tyr Asn Asp Tyr Ile Asp Ile Cys Asn Gln Glu Leu
                565                 570                 575

Asn Glu Met Lys Lys Ile Ile Val Gly Gly Asn Thr Met Phe Ser Leu
            580                 585                 590

Ile Phe Thr Asp His Gly Ala Lys Ile Ile His Arg Tyr Ala Asn Asn
        595                 600                 605

Pro Glu Leu Arg Ala Tyr Tyr Glu Ser Lys Gln Asn Lys Ile Tyr Val
    610                 615                 620

Glu Val Tyr Asp Ile Ile Ser Asn Ala Ile Val Lys His Asn Lys Ile
625                 630                 635                 640

His Lys Asn Ile Glu Ser Val Asp Asp Asn Thr Tyr Ile Ser Asn Leu
                645                 650                 655

Pro Tyr Thr Ile Lys Tyr Lys Ile Phe Glu Gln Gln Asp Tyr Lys Asp
            660                 665                 670

Asp Asp Asp Lys
        675
```

<210> SEQ ID NO 3
<211> LENGTH: 11742
<212> TYPE: DNA
<213> ORGANISM: Artificial Sequence
<220> FEATURE:
<223> OTHER INFORMATION: Description of Artificial Sequence: Synthetic
      Nucleotide sequence of pLL07

<400> SEQUENCE: 3

```
tcagaattgg ttaattggtt gtaacactga cccctatttg tttatttttc taaatacatt     60

caaatatgta tccgctcatg agacaataac cctgataaat gcttcaataa tattgaaaaa    120

ggaagaatat gagccatatt caacgggaaa cgtcgaggcc gcgattaaat tccaacatgg    180

atgctgattt atatgggtat aaatgggctc gcgataatgt cgggcaatca ggtgcgacaa    240

tctatcgctt gtatgggaag cccgatgcgc cagagttgtt tctgaaacat ggcaaaggta    300

gcgttgccaa tgatgttaca gatgagatgg tcagactaaa ctggctgacg gaatttatgc    360

cacttccgac catcaagcat tttatccgta ctcctgatga tgcatggtta ctcaccactg    420

cgatccccgg aaaaacagcg ttccaggtat tagaagaata tcctgattca ggtgaaaata    480

ttgttgatgc gctggcagtg ttcctgcgcc ggttgcactc gattcctgtt tgtaattgtc    540

cttttaacag cgatcgcgta tttcgcctcg ctcaggcgca atcacgaatg aataacggtt    600

tggttgatgc gagtgatttt gatgacgagc gtaatggctg gcctgttgaa caagtctgga    660

aagaaatgca taaacttttg ccattctcac cggattcagt cgtcactcat ggtgatttct    720

cacttgataa ccttattttt gacgagggga aattaatagg ttgtattgat gttggacgag    780

tcggaatcgc agaccgatac caggatcttg ccatcctatg gaactgcctc ggtgagtttt    840

ctccttcatt acagaaacgg ctttttcaaa aatatggtat tgataatcct gatatgaata    900

aattgcagtt tcatttgatg ctcgatgagt ttttctaact catgaccaaa atcccttaac    960

gtgagttacg cgcgcgtcgt tccactgagc gtcagacccc gtagaaaaga tcaaaggatc   1020

ttcttgagat cctttttttc tgcgcgtaat ctgctgcttg caaacaaaaa aaccaccgct   1080

accagcggtg gtttgtttgc cggatcaaga gctaccaact ctttttccga aggtaactgg   1140

cttcagcaga gcgcagatac caaatactgt tcttctagtg tagccgtagt tagcccacca   1200

cttcaagaac tctgtagcac cgcctacata cctcgctctg ctaatcctgt taccagtggc   1260
```

-continued

```
tgctgccagt ggcgataagt cgtgtcttac cgggttggac tcaagacgat agttaccgga   1320
taaggcgcag cggtcgggct gaacgggggg ttcgtgcaca cagcccagct tggagcgaac   1380
gacctacacc gaactgagat acctacagcg tgagctatga gaaagcgcca cgcttcccga   1440
agggagaaag gcggacaggt atccggtaag cggcagggtc ggaacaggag agcgcacgag   1500
ggagcttcca gggggaaacg cctggtatct ttatagtcct gtcgggtttc gccacctctg   1560
acttgagcgt cgatttttgt gatgctcgtc aggggggcgg agcctatgga aaaacgccag   1620
caacgcggcc tttttacggt tcctggcctt ttgctggcct tttgctcaca tgttctttcc   1680
tgcgttatcc cctgattctg tggataaccg tattaccgcc tttgagtgag ctgataccgc   1740
tctcaatatt ggccattagc catattattc attggttata tagcataaat caatattggc   1800
tattggccat tgcatacgtt gtatctatat cataatatgt acatttatat tggctcatgt   1860
ccaatatgac cgccatgttg gcattgatta ttgactagtt attaatagta atcaattacg   1920
gggtcattag ttcatagccc atatatggag ttccgcgtta cataacttac ggtaaatggc   1980
ccgcctggct gaccgcccaa cgacccccgc ccattgacgt caataatgac gtatgttccc   2040
atagtaacgc caatagggac tttccattga cgtcaatggg tggagtattt acggtaaact   2100
gcccacttgg cagtacatca agtgtatcat atgccaagtc cgccccctat tgacgtcaat   2160
gacggtaaat ggcccgcctg gcattatgcc cagtacatga ccttacggga ctttcctact   2220
tggcagtaca tctacgtatt agtcatcgct attaccatgc tgatgcggtt ttggcagtac   2280
accaatgggc gtggatagcg gtttgactca cggggatttc caagtctcca ccccattgac   2340
gtcaatggga gtttgttttg gcaccaaaat caacgggact ttccaaaatg tcgtaataac   2400
cccgccccgt tgacgcaaat gggcggtagg cgtgtacggt gggaggtcta tataagcaga   2460
gctcgtttag tgaaccgtca gatcactaga agctttattg cggtagttta tcacagttaa   2520
attgctaacg cagtcaggcc aacatgggct ctagcctgga cgacgagcac atcctgagcg   2580
ccctgctgca gagcgacgac gaactggtgg gcgaggacag cgacagcgag gtcagcgacc   2640
acgtgtccga ggacgacgtg cagtccgaca ccgaggaagc cttcatcgac gaggtgcacg   2700
aagtgcagcc taccagcagc ggctccgaga tcctggacga gcagaacgtg atcgagcagc   2760
ctggcagctc cctggccagc aacagaatcc tgaccctgcc ccagagaacc atcagaggca   2820
agaacaagca ctgctggtcc acctccaaga gcaccaggcg gagcagagtg tccgccctga   2880
acatcgtgcg gagccagagg ggccccacca gaatgtgcag aaacatctac gacccccctgc   2940
tgtgcttcaa gctgttcttc accgacgaga tcatcagcga gatcgtgaag tggaccaacg   3000
ccgagatcag cctgaagagg cgggagagca tgaccagcgc caccttcaga gacaccaacg   3060
aggacgagat ctacgccttc ttcggcatcc tggtgatgac cgccgtgaga aaggacaacc   3120
acatgagcac cgacgacctg ttcgacagat ccctgagcat ggtgtacgtg tccgtgatga   3180
gcagagacag attcgacttc ctgatcagat gcctgagaat ggacgacaag agcatcagac   3240
ccaccctgcg ggagaacgac gtgttcaccc ccgtgcggaa gatctgggac ctgttcatcc   3300
accagtgcat ccagaactac acccctggcg cccacctgac catcgatgag cagctgctgg   3360
gcttcagagg cagatgcccc ttcagagtgt acatccccaa caagcccagc aagtacggca   3420
tcaagatcct gatgatgtgc gacagcggca ccaagtacat gatcaacggc atgccctacc   3480
tgggcagagg cacccagaca aacggcgtgc ccctgggcga gtactacgtg aaagaactga   3540
gcaagcctgt gcatggcagc tgcaggaaca tcacatgcga caactggttc accagcatcc   3600
ccctggccaa gaacctcctg caggaaccct acaagctgac catcgtgggc accgtgcgga   3660
```

-continued

```
gcaacaagcg ggagatccca gaggtgctga agaacagcag atccagacct gtgggaacaa   3720
gcatgttctg cttcgacggc cccctgaccc tggtgtccta caagcccaag cccgccaaga   3780
tggtgtacct cctgtccagc tgcgacgagg acgccagcat caacgagagc accggcaagc   3840
cccagatggt gatgtactac aaccagacca agggcggcgt ggacaccctg gaccagatgt   3900
gcagcgtgat gacatgcagc agaaagacca acagatggcc tatggccctg ctgtacggca   3960
tgatcaatat cgcctgcatc aacagcttca tcatctacag ccacaacgtg tccagcaagg   4020
gcgagaaggt gcagagccgg aagaaattca tgcggaacct gtacatgagc ctgacctcca   4080
gcttcatgag aaagagactg gaagccccca ccctgaagag atacctccgg gacaacatca   4140
gcaacatcct gcccaaggaa gtgccaggaa caagcgacga cagcaccgag gaacccgtga   4200
tgaagaagag gacctactgc acctactgtc ccagcaagat cagaagaaag gccaacgcca   4260
gctgcaagaa atgcaaaaaa gtgatctgcc gggagcacaa catcgacatg tgccagagct   4320
gtttctgatt cagacatgat aagatacatt gatgagtttg gacaaaccac aactagaatg   4380
cagtgaaaaa aatgctttat ttgtgaaatt tgtgatgcta ttgctttatt tgtaaccatt   4440
ataagctgca ataaacaagt taacaacaac aattgcattc attttatgtt tcaggttcag   4500
ggggagatgt gggaggtttt ttaaagcaag taaaacctct acaaatgtgg taagcaggtt   4560
taaccctaga aagatagtct gcgtaaaatt gacgcatgca ttcttgaaat attgctctct   4620
ctttctaaat agcgcgaatc cgtcgctgtg catttaggac atctcagtcg ccgcttggag   4680
ctcccgtgag gcgtgcttgt caatgcggta agtgtcactg attttgaact ataacgaccg   4740
cgtgagtcaa aatgacgcat gattatcttt tacgtgactt ttaagattta actcatacga   4800
taattatatt gttatttcat gttctactta cgtgataact tattatatat atattttctt   4860
gttatagata tctttcttta tgttttaaat gcactgacct cccacattcc ctttttagta   4920
aaatattcag aaataattta aatacatcat tgcaatgaaa ataaatgttt tttattaggc   4980
agaatccaga tgctcaaggc ccttcataat atcccccagt ttagtagttg gacttaggga   5040
acaaaggaac ctttaataga aattggacag caagaaagcg agctattcct ttgccctcgg   5100
acgagtgctg gggcgtcggt ttccactatc ggcgagtact tctacacagc catcggtcca   5160
gacggccgcg cttctgcggg cgatttgtgt acgcccgaca gtcccggctc cggatcggac   5220
gattgcgtcg catcgaccct gcgcccaagc tgcatcatcg aaattgccgt caaccaagct   5280
ctgatagagt tggtcaagac caatgcggag catatacgcc cggagccgcg gcgatcctgc   5340
aagctccgga tgcctccgct cgaagtagcg cgtctgctgc tccatacaag ccaaccacgg   5400
cctccagaag aagatgttgg cgacctcgta ttgggaatcc ccgaacatcg cctcgctcca   5460
gtcaatgacc gctgttatgc ggccattgtc cgtcaggaca ttgttggagc cgaaatccgc   5520
gtgcacgagg tgccggactt cggggcagtc ctcggcccaa agcatcagct catcgagagc   5580
ctgcgcgacg gacgcactga cggtgtcgtc catcacagtt tgccagtgat acacatgggg   5640
atcagcaatc gcgcatatga aatcacgcca tgtagtgtat tgaccgattc cttgcggtcc   5700
gaatgggccg aacccgctcg tctggctaag atcggccgca gcgatcgcat ccatggcctc   5760
cgcgaccggc tgcagaacag cgggcagttc ggtttcaggc agatcttgca acgtgacacc   5820
ctgtgcacgg cgggagatgc aataggtcag gctctcgctg aattccccaa tgtcaagcac   5880
ttccggaatc gggagcgcgg ccgatgcaaa gtgccgataa acataacgat ctttgtagaa   5940
accatcggcg cagctattta cccgcaggac atatccacgc cctcctacat cgaagctgaa   6000
```

-continued

```
agcacgagat tcttcgccct ccgagagctg catcaggtcg gacacgctgt cgaacttttc   6060
gatcagaaac ttctcgacag acgtcgcggt gagttcaggc tttttcatgg tggcggacga   6120
aaggcccgga gatgaggaag aggagaacag cgcggcagac gtgcgctttt gaagcgtgca   6180
gaatgccggg cctccggagg accttcgggc gcccgccccg cccctgagcc cgcccctgag   6240
cccgcccccg gacccacccc ttcccagcct ctgagcccag aaagcgaagg agcaaagctg   6300
ctattggccg ctgccccaaa ggcctacccg cttccattgc tcagcggtgc tgtccatctg   6360
cacgagacta gtgagtcgtg ctacttccat ttgtcacgtc ctgcacgacg cgagctgcgg   6420
ggcggggggg aacttcctga ctaggggagg agtagaaggt ggcgcgaagg ggccaccaaa   6480
gaacggagcc ggttggcgcc taccggtgga tgtggaatgt gtgcgaggcc agaggccact   6540
tgtgtagcgc caagtgccca gcggggctgc taaagcgcat gctccagact gccttgggaa   6600
aagcgcctcc cctacccggt agagaaactt gatctgtcgc cgcaattcaa gcttcgtgag   6660
gctccggtgc ccgtcagtga cctgctatac tctggagacg gcacatcgcc cacagtcccc   6720
gagaagttgg gaggggtcgg caattgaacc ggtgcctaga gaaggtggcg cggggtaaac   6780
tgggaaagtg atgtcgtgta ctggctccgc ctttttcccg agggtggggg agaaccgtat   6840
ataagtgcag tagtcgccgt gaacgttctt tttcgcaacg ggtttgccgc cagaacacag   6900
gtaagtgccg tgtgtggttc ccgcgggcct ggcctcttta cgggttatgg cccttgcgtg   6960
ccttgaatta cttccacctg gctccagtac gtgattcttg atcccgagct ggagccaggg   7020
gcgggccttg cgctttagga gccccttcgc ctcgtgcttg agttgaggcc tggcctgggc   7080
gctggggccg ccgcgtgcga atctggtggc accttcgcgc ctgtctcgct gctttcgata   7140
agtctctagc catttaaaat ttttgatgac gtgctgcgac gcttttttc tggcaagata    7200
gtcttgtaaa tgcgggccag gatctgcaca ctggtatttc ggtttttggg cccgcggccg   7260
gcgacggggc ccgtgcgtcc cagcgcacat gttcggcgag gcggggcctg cgagcgcggc   7320
caccgagaat cggacggggg tagtctcaag ctggccggcc tgctctggtg cctggcctcg   7380
cgccgccgtg tatcgccccg ccctgggcgg caaggctggc ccggtcggca ccagttgcgt   7440
gagcggaaag atggccgctt cccggccctg ctccaggggg ctcaaaatgg aggacgcggc   7500
gctcgggaga gcgggcgggt gagtcaccca cacaaaggaa aagggccttt ccgtcctcag   7560
ccgtcgcttc atgtgactcc acggagtacc gggcgccgtc caggcacctc gattagttct   7620
ggagcttttg gagtacgtcg tctttaggtt ggggggaggg gttttatgcg atggagtttc   7680
cccacactga gtgggtggag actgaagtta ggccagcttg gcacttgatg taattctcct   7740
tggaatttgg cctttttgag tttggatctt ggttcattct caagcctcag acagtggttc   7800
aaagtttttt tcttccattt caggtgtcgt gaacacgtct cgggggggccg ccaccatgtt  7860
cgactacctg gaaaatgagg aagtggccct ggacgagctg aagcagatgc tgcgggaccg   7920
ggaccccaac gacacccgga accagttcaa gaacaacgcc ctgcacgcct acctgtttaa   7980
cgagcactgc aacaacgtgg aagtggtcaa gctgctgctg gactccggca ccaacccccct  8040
gcacaagaac tggcggcagc tgaccccccct gggcgagtac accaactccc ggcacggcaa  8100
agtgaacaag gatatcgcca tggtgctgct ggaagctacc ggctactcca acatcaacga   8160
cttcaacatc ttcacctaca tgaagtccaa gaacgtggac atcgacctga tcaaggtgct   8220
ggtggaacac ggcttcgact tctccgtgaa gtgcgagaag caccactccg tgatcgagaa   8280
ctacgtgatg accgacgacc ccgtgcctga gatcatcgac ctgttcatcg agaacggctg   8340
ctccgtgatc tacgaggacg aggacgacga gtacggctac gcctacgagg aataccactc   8400
```

-continued

```
ccagaacgac gactaccagc cccggaactg cggcaccgtg ctgcacctgt acatcatctc   8460
ccacctgtac tccgagagcg actcccggtc ttgcgtgaac cccgaggtgg tcaagtgcct   8520
gatcaaccac ggcatcaacc cctccagcat cgataagaac tactgcaccg ccctgcagta   8580
ctacatcaag tcctcccaca tcgacatcga tatcgtgaag ctgctgatga agggcatcga   8640
caacaccgcc tacagctaca tcgacgacct gacctgctgc acccggggca tcatggccga   8700
ctacctgaac agcgactacc ggtacaacaa ggacgtggac ctggatctgg tcaaactgtt   8760
cctggaaaac ggcaagcctc acggcatcat gtgctccatc gtgcccctgt ggcggaacga   8820
caaagagaca atctccctga tcctgaaaac catgaactcc gacgtgctgc agcatatcct   8880
gatcgagtac atcaccttct ccgatatcga catctctctg gtcgagtaca tgctggaata   8940
cggcgctgtg gtcaacaaag aggccatcca cggctacttc aagaacatca acatcgactc   9000
ctacaccatg aagtacctgc tgaaaaaaga gggcggcgac gccgtcaacc acctggacga   9060
cggcgagatc cccatcggcc acctgtgcaa gagcaactac ggccggtaca acttttacac   9120
cgacacctac cggcagggct tccgggacat gtcctacgcc tgccccatcc tgtccaccat   9180
caacatctgc ctgccctacc tgaaggacat caatatgatc gataagcggg gcgagacact   9240
gctgcacaag gccgtgcgct acaacaagca gtccctggtg tccctgctgc tggaaagcgg   9300
ctccgacgtg aacatccggt ccaacaacgg ctacacctgt atcgctatcg ccatcaacga   9360
gtcccggaac atcgagctgc tgaatatgct gctgtgccac aagcctaccc tggactgcgt   9420
gatcgactcc ctgcgcgaga tcagcaacat cgtggacaac gcctacgcca tcaagcagtg   9480
catcagatac gccatgatta tcgacgactg catctcctcc aagatccccg agtccatctc   9540
caagcactac aacgactaca ttgacatctg caaccaggaa ctgaacgaga tgaagaaaat   9600
catcgtgggc ggcaacacca tgttcagcct gatcttcacc gatcacggcg ccaagatcat   9660
ccaccgctac gccaacaacc ccgagctgcg ggcctactac gagtccaagc agaacaagat   9720
ctacgtcgag gtctacgaca tcatcagcaa cgccatcgtg aagcacaaca agattcacaa   9780
gaacatcgag tccgtggacg acaacaccta catctccaac ctgccctata ccatcaagta   9840
caagatcttc gagcagcagg attacaagga tgacgatgac aagtgaaaaa gcgtcttcct   9900
gttctcatca catcatatca aggttatata ccatcaatat tgccacagat gttacttagc   9960
cttttaatat ttctctaatt tagtgtatat gcaatgatag ttctctgatt tctgagattg  10020
agtttctcat gtgtaatgat tatttagagt ttctctttca tctgttcaaa tttttgtcta  10080
gttttatttt ttactgattt gtaagacttc tttttataat ctgcatatta caattctctt  10140
tactggggtg ttgcaaatat tttctgtcat tctatggcct gacttttctt aatggttttt  10200
taattttaaa aataagtctt aatattcatg caatctaatt aacaatcttt tctttgtggt  10260
taggactttg agtcataaga aatttttctc tacactgaag tcatgatggc atgcttctat  10320
attattttct aaaagattta aagttttgcc ttctccattt agacttataa ttcactggaa  10380
ttttttgtg tgtatggtat gacatatggg ttccctttta ttttttacat ataaatatat  10440
ttccctgttt ttctaaaaaa gaaaaagatc atcattttcc cattgtaaaa tgccatattt  10500
ttttcatagg tcacttacat atatcaatgg gtctgtttct gagctctact ctattttatc  10560
agcctcactg tctatcccca cacatctcat gctttgctct aaatcttgat atttagtgga  10620
acattctttc ccattttgtt ctacaagaat atttttgtta ttgtctttgg gctttctata  10680
tacattttga aatgaggttg acaagttaat aatcaacctc tggattacaa aatttgtgaa  10740
```

-continued

```
agattgactg gtattcttaa ctatgttgct ccttttacgc tatgtggata cgctgcttta  10800

atgcctttgt atcatgctat tgcttcccgt atggctttca ttttctcctc cttgtataaa  10860

tcctggttgc tgtctcttta tgaggagttg tggcccgttg tcaggcaacg tggcgtggtg  10920

tgcactgtgt ttgctgacgc aacccccact ggttggggca ttgccaccac ctgtcagctc  10980

ctttccggga ctttcgcttt ccccctccct attgccacgg cggaactcat cgccgcctgc  11040

cttgcccgct gctggacagg ggctcggctg ttgggcactg acaattccgt ggtgttgtcg  11100

gggaaatcat cgtcctttcc ttggctgctc gcctgtgttg ccacctggat tctgcgcggg  11160

acgtccttct gctacgtccc ttcggccctc aatccagcgg accttccttc ccgcggcctg  11220

ctgccggctc tgcggcctct tccgcctctt cgccttcgcc ctcagacgag tcggatctcc  11280

ctttgggccg cctccccgca tcgcctgcta ttgtcttgcc aatcctcccc cttgctgtcc  11340

tgccccaccc caccccccag aatagaatga cacctactca gacaatgcga tgcaatttcc  11400

tcattttatt aggaaaggac agtgggagtg gcaccttcca gggtcaagga aggcacgggg  11460

gaggggcaaa caacagatgg ctggcaacta gaaggcacat ttgttacttt atagaagaaa  11520

ttttgagttt ttgttttttt ttaataaata aataaacata aataaattgt ttgttgaatt  11580

tattattagt atgtaagtgt aaatataata aaacttaata tctattcaaa ttaataaata  11640

aacctcgata tacagaccga taaaacacat gcgtcaattt tacgcatgat tatctttaac  11700

gtacgtcaca atatgattat ctttctaggg ttaagaagac tg                     11742
```

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic Forward primer for CP77-CHO gene from pPH51 plasmid

<400> SEQUENCE: 4

```
aacacgtctc gggggccgc caccatgttc gactacctgg aaaatgagga agtg           54
```

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic Reverse primer for CP77-CHO gene from pPH51 plasmid

<400> SEQUENCE: 5

```
caggaagacg ctttttcact tgtcatcgtc atccttgtaa tcctgctgct cgaagatctt     60

gtact                                                                 65
```

<210> SEQ ID NO 6
<211> LENGTH: 855
<212> TYPE: DNA
<213> ORGANISM: Artificial Sequence
<220> FEATURE:
<223> OTHER INFORMATION: Description of Artificial Sequence: Synthetic Nucleotide sequence of vaccinia Copenhagen K1L gene (extract from Genbank M35027.1)

<400> SEQUENCE: 6

```
atggatctgt cacgaattaa tacttggaag tctaagcagc tgaaaagctt tctctctagt     60

aaagatacat ttaaggcgga tgtccatgga catagtgcct tgtattatgc aatagctgat    120

aataacgtgc gtctagtatg tacgttgttg aacgctggag cattgaaaaa tcttctagag    180
```

```
aatgaatttc cattacatca ggcagccaca ttagaagata ccaaaatagt aaagattttg    240

ctattcagtg gaatggatga ttcacaattt gatgacaaag gaaacaccgc attgtattat    300

gcggttgata gtggtaacat gcaaacggtg aaactgtttg ttaagaaaaa ttggagactg    360

atgttctatg ggaaaactgg atggaaaact tcattttatc atgccgtcat gcttaatgat    420

gtaagtattg tatcatactt tctttcagaa ataccatcta cttttgatct ggctattctc    480

cttagttgta ttcacaccac tataaaaaat ggacacgtgg atatgatgat tctcttgctc    540

gactatatga cgtcgacaaa caccaataat tcccttctct tcattccgga cattaaattg    600

gctatagata ataaagacat tgagatgtta caggctctgt tcaaatacga cattaatatc    660

tactctgtta atctggaaaa tgtactattg gatgatgccg aaataactaa gatgattata    720

gaaaagcatg ttgaatacaa gtctgactcc tatacaaaag atctcgatat cgtcaagaat    780

aataaattgg atgaaataat tagcaaaaac aaggaactca gactcatgta cgtcaattgt    840

gtaaagaaaa actaa                                                      855
```

<210> SEQ ID NO 7
<211> LENGTH: 284
<212> TYPE: PRT
<213> ORGANISM: Artificial Sequence
<220> FEATURE:
<223> OTHER INFORMATION: Description of Artificial Sequence: Synthetic
      Amino acid sequence of vaccinia Copenhagen K1L
      (extract from Genbank M35027.1) encoded by SEQ ID NO: 6

<400> SEQUENCE: 7

```
Met Asp Leu Ser Arg Ile Asn Thr Trp Lys Ser Lys Gln Leu Lys Ser
1               5                   10                  15

Phe Leu Ser Ser Lys Asp Thr Phe Lys Ala Asp Val His Gly His Ser
            20                  25                  30

Ala Leu Tyr Tyr Ala Ile Ala Asp Asn Asn Val Arg Leu Val Cys Thr
        35                  40                  45

Leu Leu Asn Ala Gly Ala Leu Lys Asn Leu Leu Glu Asn Glu Phe Pro
    50                  55                  60

Leu His Gln Ala Ala Thr Leu Glu Asp Thr Lys Ile Val Lys Ile Leu
65                  70                  75                  80

Leu Phe Ser Gly Met Asp Asp Ser Gln Phe Asp Asp Lys Gly Asn Thr
                85                  90                  95

Ala Leu Tyr Tyr Ala Val Asp Ser Gly Asn Met Gln Thr Val Lys Leu
            100                 105                 110

Phe Val Lys Lys Asn Trp Arg Leu Met Phe Tyr Gly Lys Thr Gly Trp
        115                 120                 125

Lys Thr Ser Phe Tyr His Ala Val Met Leu Asn Asp Val Ser Ile Val
    130                 135                 140

Ser Tyr Phe Leu Ser Glu Ile Pro Ser Thr Phe Asp Leu Ala Ile Leu
145                 150                 155                 160

Leu Ser Cys Ile His Thr Thr Ile Lys Asn Gly His Val Asp Met Met
                165                 170                 175

Ile Leu Leu Leu Asp Tyr Met Thr Ser Thr Asn Thr Asn Asn Ser Leu
            180                 185                 190

Leu Phe Ile Pro Asp Ile Lys Leu Ala Ile Asp Asn Lys Asp Ile Glu
        195                 200                 205

Met Leu Gln Ala Leu Phe Lys Tyr Asp Ile Asn Ile Tyr Ser Val Asn
    210                 215                 220
```

```
Leu Glu Asn Val Leu Leu Asp Asp Ala Glu Ile Thr Lys Met Ile Ile
225                 230                 235                 240

Glu Lys His Val Glu Tyr Lys Ser Asp Ser Tyr Thr Lys Asp Leu Asp
                245                 250                 255

Ile Val Lys Asn Asn Lys Leu Asp Glu Ile Ile Ser Lys Asn Lys Glu
            260                 265                 270

Leu Arg Leu Met Tyr Val Asn Cys Val Lys Lys Asn
        275                 280


<210> SEQ ID NO 8
<211> LENGTH: 551
<212> TYPE: PRT
<213> ORGANISM: Artificial Sequence
<220> FEATURE:
<223> OTHER INFORMATION: Description of Artificial Sequence: Synthetic
      VACV-COP-D13L ORF sequence

<400> SEQUENCE: 8

Met Asn Asn Thr Ile Ile Asn Ser Leu Ile Gly Gly Asp Asp Ser Ile
1               5                   10                  15

Lys Arg Ser Asn Val Phe Ala Val Asp Ser Gln Ile Pro Thr Leu Tyr
            20                  25                  30

Met Pro Gln Tyr Ile Ser Leu Ser Gly Val Met Thr Asn Asp Gly Pro
        35                  40                  45

Asp Asn Gln Ala Ile Ala Ser Phe Glu Ile Arg Asp Gln Tyr Ile Thr
    50                  55                  60

Ala Leu Asn His Leu Val Leu Ser Leu Glu Leu Pro Glu Val Lys Gly
65                  70                  75                  80

Met Gly Arg Phe Gly Tyr Val Pro Tyr Val Gly Tyr Lys Cys Ile Asn
                85                  90                  95

His Val Ser Ile Ser Ser Cys Asn Gly Val Ile Trp Glu Ile Glu Gly
            100                 105                 110

Glu Glu Leu Tyr Asn Asn Cys Ile Asn Asn Thr Ile Ala Leu Lys His
        115                 120                 125

Ser Gly Tyr Ser Ser Glu Leu Asn Asp Ile Ser Ile Gly Leu Thr Pro
    130                 135                 140

Asn Asp Thr Ile Lys Glu Pro Ser Thr Val Tyr Val Tyr Ile Lys Thr
145                 150                 155                 160

Pro Phe Asp Val Glu Asp Thr Phe Ser Ser Leu Lys Leu Ser Asp Ser
                165                 170                 175

Lys Ile Thr Val Thr Val Thr Phe Asn Pro Val Ser Asp Ile Val Ile
            180                 185                 190

Arg Asp Ser Ser Phe Asp Phe Glu Thr Phe Asn Lys Glu Phe Val Tyr
        195                 200                 205

Val Pro Glu Leu Ser Phe Ile Gly Tyr Met Val Lys Asn Val Gln Ile
    210                 215                 220

Lys Pro Ser Phe Ile Glu Lys Pro Arg Arg Val Ile Gly Gln Ile Asn
225                 230                 235                 240

Gln Pro Thr Ala Thr Val Thr Glu Val His Ala Ala Thr Ser Leu Ser
                245                 250                 255

Val Tyr Thr Lys Pro Tyr Tyr Gly Asn Thr Asp Asn Lys Phe Ile Ser
            260                 265                 270

Tyr Pro Gly Tyr Ser Gln Asp Glu Lys Asp Tyr Ile Asp Ala Tyr Val
        275                 280                 285

Ser Arg Leu Leu Asp Asp Leu Val Ile Val Ser Asp Gly Pro Pro Thr
    290                 295                 300
```

-continued

```
Gly Tyr Pro Glu Ser Ala Glu Ile Val Glu Val Pro Glu Asp Gly Ile
305                 310                 315                 320

Val Ser Ile Gln Asp Ala Asp Val Tyr Val Lys Ile Asp Asn Val Pro
                325                 330                 335

Asp Asn Met Ser Val Tyr Leu His Thr Asn Leu Leu Met Phe Gly Thr
            340                 345                 350

Arg Lys Asn Ser Phe Ile Tyr Asn Ile Ser Lys Lys Phe Ser Ala Ile
        355                 360                 365

Thr Gly Thr Tyr Ser Asp Ala Thr Lys Arg Thr Ile Phe Ala His Ile
    370                 375                 380

Ser His Ser Ile Asn Ile Ile Asp Thr Ser Ile Pro Val Ser Leu Trp
385                 390                 395                 400

Thr Ser Gln Arg Asn Val Tyr Asn Gly Asp Asn Arg Ser Ala Glu Ser
                405                 410                 415

Lys Ala Lys Asp Leu Phe Ile Asn Asp Pro Phe Ile Lys Gly Ile Asp
            420                 425                 430

Phe Lys Asn Lys Thr Asp Ile Ile Ser Arg Leu Glu Val Arg Phe Gly
        435                 440                 445

Asn Asp Val Leu Tyr Ser Glu Asn Gly Pro Ile Ser Arg Ile Tyr Asn
    450                 455                 460

Glu Leu Leu Thr Lys Ser Asn Asn Gly Thr Arg Thr Leu Thr Phe Asn
465                 470                 475                 480

Phe Thr Pro Lys Ile Phe Phe Arg Pro Thr Thr Ile Thr Ala Asn Val
                485                 490                 495

Ser Arg Gly Lys Asp Lys Leu Ser Val Arg Val Val Tyr Ser Thr Met
            500                 505                 510

Asp Val Asn His Pro Ile Tyr Tyr Val Gln Lys Gln Leu Val Val Val
        515                 520                 525

Cys Asn Asp Leu Tyr Lys Val Ser Tyr Asp Gln Gly Val Ser Ile Thr
    530                 535                 540

Lys Ile Met Gly Asp Asn Asn
545                 550
```

<210> SEQ ID NO 9
<211> LENGTH: 1680
<212> TYPE: DNA
<213> ORGANISM: Artificial Sequence
<220> FEATURE:
<223> OTHER INFORMATION: Description of Artificial Sequence: Synthetic CHO codon optimised nucleotide sequence encoding SEQ ID NO:1

<400> SEQUENCE: 9

```
atgaacaaca ccatcatcaa ctccctgatc ggcggcgacg actccatcaa gcggtccaac      60

gtgttcgccg tggactccca gatccccacc ctgtacatgc cccagtacat ctccctgtcc     120

ggcgtgatga ccaacgacgg ccctgacaac caggctatcg cctccttcga gatccgggat     180

cagtacatca ccgccctgaa ccacctggtg ctgtccctgg aactgcccga agtgaagggc     240

atgggcagat tcggctacgt gccctacgtg ggctacaagt gcatcaacca cgtgtccatc     300

tccagctgca acggcgtgat ctgggaaatc gagggcgagg aactgtacaa caactgcatt     360

aacaacacaa tcgccctgaa gcactccggc tactcctccg agctgaacga catctccatc     420

ggcctgaccc ccaacgacac catcaaagaa ccctccaccg tgtacgtgta catcaagacc     480

cccttcgacg tggaagatac cttctccagc ctgaagctgt ccgactccaa gatcaccgtg     540

accgtgacct tcaaccctgt gtccgacatc gtgatccggg actccagctt cgacttcgag     600
```

acattcaaca aagaatttgt gtacgtgccc gagctgtcct tcatcggcta catggtcaag 660
aacgtgcaga tcaagcccag cttcatcgag aagcctcgga gagtgatcgg ccagatcaac 720
cagcctaccg ccaccgtgac agaggtgcac gccgccacat ccctgagcgt gtacaccaag 780
ccctactacg gcaacaccga caacaagttc atctcctacc ccggctacag ccaggacgag 840
aaggactaca tcgacgccta cgtgtcccgg ctgctggacg acctcgtgat cgtgtctgat 900
ggccccccta ccggctaccc tgagtctgcc gagatcgtgg aagtgcccga ggacggcatc 960
gtcagcatcc aggacgccga tgtgtatgtg aagatcgaca acgtgccaga caacatgtcc 1020
gtgtacctgc acaccaacct gctgatgttc ggcacccgga agaattcctt catctacaac 1080
atctccaaga agttctccgc catcaccggc acctactccg acgccaccaa gcggaccatc 1140
ttcgcccaca tctcccacag catcaacatc atcgacacct ccatccccgt gtccctgtgg 1200
acctctcaga gaaacgtgta caacggcgac aacagatccg ccgagtccaa ggccaaggac 1260
ctgttcatca acgacccctt catcaagggc atcgacttca agaacaagac cgacatcatc 1320
tcccggctgg aagtgcgctt cggcaacgac gtgctgtact ccgagaacgg ccctatcagc 1380
cggatctaca acgagctgct gaccaagtcc aacaacggca ccagaaccct gacctttaac 1440 tttacccccca agatcttctt ccggcccacc accatcaccg ctaacgtgtc cagaggcaag 1500
gacaagctga gcgtgcgggt ggtgtactcc accatggacg tgaaccaccc catctactac 1560
gtgcagaaac agctggtggt cgtgtgcaac gatctgtaca aggtgtccta cgaccagggc 1620
gtgtccatta ccaagatcat gggcgataac aacgactaca aggacgacga cgacaagtga 1680

<210> SEQ ID NO 10
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
aacacgtctc gggggccgc caccatgaac aacaccatca tcaa 44

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
caggaagacg ctttttcact tgtcgtcgtc gtccttgtag 40

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic Flag-Tag protein

<400> SEQUENCE: 12

Asp Tyr Lys Asp Asp Asp Asp Lys
1 5

<210> SEQ ID NO 13

<211> LENGTH: 16
<212> TYPE: PRT
<213> ORGANISM: Artificial Sequence
<220> FEATURE:
<223> OTHER INFORMATION: Description of Artificial Sequence: Synthetic
      D13L peptide

<400> SEQUENCE: 13

Cys Tyr Asp Gln Gly Val Ser Ile Thr Lys Ile Met Gly Asp Asn Asn
1               5                   10                  15

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggtacccgg ggatcacgaa aaataatagt aacca                                  35

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aatttagtgt gcgcgtggaa aaagcttaca ataaactc                               38

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atatttaaat gcgcgcaata atggaacaag aaccct                                 36

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgactctaga ggatcgcgct gaggtcggca actacg                                 36

<210> SEQ ID NO 18
<211> LENGTH: 668
<212> TYPE: PRT
<213> ORGANISM: Artificial Sequence
<220> FEATURE:
<223> OTHER INFORMATION: Description of Artificial Sequence: Synthetic
      CP77 protein comprising sequence of CPXV-125L Brighton Red

<400> SEQUENCE: 18

Met Phe Asp Tyr Leu Glu Asn Glu Glu Val Ala Leu Asp Glu Leu Lys
1               5                   10                  15

Gln Met Leu Arg Asp Arg Asp Pro Asn Asp Thr Arg Asn Gln Phe Lys

-continued

```
            20                  25                  30

Asn Asn Ala Leu His Ala Tyr Leu Phe Asn Glu His Cys Asn Asn Val
        35                  40                  45

Glu Val Val Lys Leu Leu Leu Asp Ser Gly Thr Asn Pro Leu His Lys
    50                  55                  60

Asn Trp Arg Gln Leu Thr Pro Leu Gly Glu Tyr Thr Asn Ser Arg His
65                  70                  75                  80

Gly Lys Val Asn Lys Asp Ile Ala Met Val Leu Leu Glu Ala Thr Gly
                85                  90                  95

Tyr Ser Asn Ile Asn Asp Phe Asn Ile Phe Thr Tyr Met Lys Ser Lys
            100                 105                 110

Asn Val Asp Ile Asp Leu Ile Lys Val Leu Val Glu His Gly Phe Asp
        115                 120                 125

Phe Ser Val Lys Cys Glu Lys His His Ser Val Ile Glu Asn Tyr Val
    130                 135                 140

Met Thr Asp Asp Pro Val Pro Glu Ile Ile Asp Leu Phe Ile Glu Asn
145                 150                 155                 160

Gly Cys Ser Val Ile Tyr Glu Asp Glu Asp Asp Glu Tyr Gly Tyr Ala
                165                 170                 175

Tyr Glu Glu Tyr His Ser Gln Asn Asp Asp Tyr Gln Pro Arg Asn Cys
            180                 185                 190

Gly Thr Val Leu His Leu Tyr Ile Ile Ser His Leu Tyr Ser Glu Ser
        195                 200                 205

Asp Ser Arg Ser Cys Val Asn Pro Glu Val Val Lys Cys Leu Ile Asn
    210                 215                 220

His Gly Ile Asn Pro Ser Ser Ile Asp Lys Asn Tyr Cys Thr Ala Leu
225                 230                 235                 240

Gln Tyr Tyr Ile Lys Ser Ser His Ile Asp Ile Asp Ile Val Lys Leu
                245                 250                 255

Leu Met Lys Gly Ile Asp Asn Thr Ala Tyr Ser Tyr Ile Asp Asp Leu
            260                 265                 270

Thr Cys Cys Thr Arg Gly Ile Met Ala Asp Tyr Leu Asn Ser Asp Tyr
        275                 280                 285

Arg Tyr Asn Lys Asp Val Asp Leu Asp Leu Val Lys Leu Phe Leu Glu
    290                 295                 300

Asn Gly Lys Pro His Gly Ile Met Cys Ser Ile Val Pro Leu Trp Arg
305                 310                 315                 320

Asn Asp Lys Glu Thr Ile Ser Leu Ile Leu Lys Thr Met Asn Ser Asp
                325                 330                 335

Val Leu Gln His Ile Leu Ile Glu Tyr Ile Thr Phe Ser Asp Ile Asp
            340                 345                 350

Ile Ser Leu Val Glu Tyr Met Leu Glu Tyr Gly Ala Val Val Asn Lys
        355                 360                 365

Glu Ala Ile His Gly Tyr Phe Lys Asn Ile Asn Ile Asp Ser Tyr Thr
    370                 375                 380

Met Lys Tyr Leu Leu Lys Lys Glu Gly Gly Asp Ala Val Asn His Leu
385                 390                 395                 400

Asp Asp Gly Glu Ile Pro Ile Gly His Leu Cys Lys Ser Asn Tyr Gly
                405                 410                 415

Arg Tyr Asn Phe Tyr Thr Asp Thr Tyr Arg Gln Gly Phe Arg Asp Met
            420                 425                 430

Ser Tyr Ala Cys Pro Ile Leu Ser Thr Ile Asn Ile Cys Leu Pro Tyr
        435                 440                 445
```

```
Leu Lys Asp Ile Asn Met Ile Asp Lys Arg Gly Glu Thr Leu Leu His
    450                 455                 460

Lys Ala Val Arg Tyr Asn Lys Gln Ser Leu Val Ser Leu Leu Leu Glu
465                 470                 475                 480

Ser Gly Ser Asp Val Asn Ile Arg Ser Asn Asn Gly Tyr Thr Cys Ile
                485                 490                 495

Ala Ile Ala Ile Asn Glu Ser Arg Asn Ile Glu Leu Leu Asn Met Leu
            500                 505                 510

Leu Cys His Lys Pro Thr Leu Asp Cys Val Ile Asp Ser Leu Arg Glu
        515                 520                 525

Ile Ser Asn Ile Val Asp Asn Ala Tyr Ala Ile Lys Gln Cys Ile Arg
    530                 535                 540

Tyr Ala Met Ile Ile Asp Asp Cys Ile Ser Ser Lys Ile Pro Glu Ser
545                 550                 555                 560

Ile Ser Lys His Tyr Asn Asp Tyr Ile Asp Ile Cys Asn Gln Glu Leu
                565                 570                 575

Asn Glu Met Lys Lys Ile Ile Val Gly Gly Asn Thr Met Phe Ser Leu
            580                 585                 590

Ile Phe Thr Asp His Gly Ala Lys Ile Ile His Arg Tyr Ala Asn Asn
        595                 600                 605

Pro Glu Leu Arg Ala Tyr Tyr Glu Ser Lys Gln Asn Lys Ile Tyr Val
    610                 615                 620

Glu Val Tyr Asp Ile Ile Ser Asn Ala Ile Val Lys His Asn Lys Ile
625                 630                 635                 640

His Lys Asn Ile Glu Ser Val Asp Asp Asn Thr Tyr Ile Ser Asn Leu
                645                 650                 655

Pro Tyr Thr Ile Lys Tyr Lys Ile Phe Glu Gln Gln
            660                 665


<210> SEQ ID NO 19
<211> LENGTH: 2903
<212> TYPE: DNA
<213> ORGANISM: Artificial Sequence
<220> FEATURE:
<223> OTHER INFORMATION: Description of Artificial Sequence: Synthetic
      CP77+DsRed expression cassette sequence

<400> SEQUENCE: 19

gcgcgcacac taaattattt tttattaata attgtacaag tttttgatct ggtataaata     60

cattcaaaaa tgataattta atgacattag ttgtgcgggt gtatagagtt cacagtagct    120

cattcacttc tattcagtca aaatgtttga ttatctggaa aatgaggagg tggctctcga    180

tgaacttaaa cagatgttga gagatagaga tcctaatgat accaggaacc aattcaagaa    240

taatgctcta catgcatacc ttttcaatga gcactgtaat aatgttgagg ttgtcaaact    300

actactagac agtggtacta atccattaca caaaaattgg agacagctta ctccattagg    360

ggaatacaca aatagtagac atggtaaagt taataaggat atagcgatgg ttctactaga    420

agctactgga tatagcaaca taaatgactt taatatattc acctatatga aatccaaaaa    480

tgtagatatt gacttgataa aggtattggt agaacatgga tttgatttta gtgttaaatg    540

cgaaaaacat cattcagtta tagaaaatta tgtaatgaca gatgatcctg ttcctgaaat    600

tattgattta ttcatagaaa atggatgcag tgttatttat gaggacgagg atgatgagta    660

cggatacgcg tatgaagaat atcactcaca aaatgacgat tatcaaccac gaaattgcgg    720

tacagtatta catctgtata tcatctctca tctgtattca gagtcggatt cgagatcatg    780
```

-continued

```
tgtgaacccg gaagttgtta aatgtctgat taatcatgga atcaacccat cttctataga    840
taaaaactat tgtacagctc ttcaatatta tattaagtca tctcatatag atatagacat    900
cgttaaattg ttaatgaaag gaatagataa cacggcttat tcatatatag acgatctaac    960
atgttgtact cgaggaatta tggctgatta tctaaatagt gattatagat acaataaaga   1020
tgtagattta gatttggtca aattgttttt ggagaatgga aaaccgcacg gaataatgtg   1080
tagtattgta ccactatgga gaaatgataa ggaaaccatc tctttgatat tgaaaacaat   1140
gaactcggat gtcctccaac atatactaat tgagtatata acattcagcg atatcgatat   1200
ctctctagtg gaatacatgt tggaatatgg agctgtggta aataaagagg ctattcacgg   1260
atactttaaa aatattaata ttgattctta cacgatgaaa tatctactaa aaaaggaagg   1320
gggagatgcc gtcaatcatc tcgatgatgg agagatcccg attggacacc tatgtaaatc   1380
caactatgga cgttataatt tctacactga tacatacaga cagggttttc gtgatatgtc   1440
ttatgcttgc ccaattctta gtactataaa catttgccta ccttatctta aagacattaa   1500
catgattgac aaacgaggag aaacacttct tcacaaggct gttagatata ataaacaatc   1560
tctagtgtct ttactgctag aatccggttc agatgtcaac attagatcaa ataacggata   1620
tacatgtata gccattgcaa tcaacgaatc tagaaacatt gaactgctga acatgctatt   1680
atgtcataaa cctacattag attgtgtgat tgattcattg agagaaatat ctaacatagt   1740
agataatgcc tatgctataa aacaatgtat tagatatgcc atgattatag atgactgtat   1800
atcgtctaag attccagagt ccataagtaa acactataat gattatatag atatttgcaa   1860
tcaagaattg aacgagatga aaaaaataat agtgggaggc aacactatgt tctcattaat   1920
atttactgat catggagcta aaattattca tcggtatgcc aataatccag aattacgtgc   1980
gtattatgag tcaaaacaaa ataaaatata cgtggaagta tatgatatta tttccaatgc   2040
gatagtgaag cataataaaa ttcataaaaa catagaatca gttgatgaca atacctacat   2100
ttctaatttg ccttatacca tcaaatacaa aatattcgag caacaataag tatttttat   2160
caaaaaattg aaattttatt ttttttttt ggaatataaa taatatggat agcactgaga   2220
acgtcatcaa gcccttcatg cgcttcaagg tgcacatgga gggctccgtg aacggccacg   2280
agttcgagat cgagggcgag ggcgagggca agccctacga gggcacccag accgccaagc   2340
tgcaggtgac caagggcggc cccctgccct tcgcctggga catcctgtcc ccccagttcc   2400
agtacggctc caaggtgtac gtgaagcacc ccgccgacat ccccgactac aagaagctgt   2460
ccttccccga gggcttcaag tgggagcgcg tgatgaactt cgaggacggc ggcgtggtga   2520
ccgtgaccca ggactcctca ctgcaggacg gcaccttcat ctaccacgtg aagttcatcg   2580
gcgtgaactt cccctccgac ggccccgtaa tgcagaagaa gactctgggc tgggagccct   2640
ccaccgagcg cctgtacccc cgcgacggcg tgctgaaggg cgagatccac aaggcgctga   2700
agctgaaggg cggcggccac tacctggtgg agttcaagtc aatctacatg gccaagaagc   2760
ccgtgaagct gcccggctac tactacgtgg actccaagct ggacatcacc tcccacaacg   2820
aggactacac cgtggtggag cagtacgaac gcgccgaggc ccgccaccac ctgttccagt   2880
agtttttata tttaaatgcg cgc                                          2903
```

<210> SEQ ID NO 20
<211> LENGTH: 25
<212> TYPE: DNA
<213> ORGANISM: Artificial Sequence
<220> FEATURE:

-continued

<223> OTHER INFORMATION: Description of Artificial Sequence: Synthetic
      primer

<400> SEQUENCE: 20
tacaaaatca aataatggtc gaaac 25

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgccaagaaa acactccttc taagacaat 29

<210> SEQ ID NO 22
<211> LENGTH: 6809
<212> TYPE: DNA
<213> ORGANISM: Artificial Sequence
<220> FEATURE:
<223> OTHER INFORMATION: Description of Artificial Sequence: Synthetic
      pLL09 homologous recombination vector sequence for the
      deletion of VACV-COP D13L with CP77/DsRed selection

<400> SEQUENCE: 22
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acccggggat 420
cacgaaaaat aatagtaacc aattagtatg ggaaaacttt ttagcacata tgagatctaa 480
aaaacgtgtt actatggtag aggattatgg acacgagtac gtttttgtag atgagaggtt 540
ttctacttgc tcattagaag tataaaaaaa tagttccgta attaaatggc taagcgagta 600
agccttccag atgtggttat ttcagcacct aaagcagtct ttaagcccgc taaagaagaa 660
gcactcgctt gtatactacc aaagtattat aaatctatgg cagatgtgtc tattaagaca 720
aatagtgtaa ttgataagtg ttggttttgt aatcaagatt tggtttttag acctattagt 780
attgagacat acaagggtgg tgaagtaggg tatttctgtt ctaaaatatg tagggattcg 840
ttggcttcta tggttaagtc tcacgtagct cttagagaag aaccaaaaat ttctttgttg 900
cctttagtat tctatgaaga taaggaaaag gttataaata caataaactt actaagagat 960
aaagacggcg tttacggaag ctgttacttt aaggaaaact cacaaattat agatatttct 1020
ctacggagtt tattgtaagc tttttccacg cgcacactaa attatttttt attaataatt 1080
gtacaagttt ttgatctggt ataaatacat tcaaaaatga taatttaatg acattagttg 1140
tgcgggtgta tagagttcac agtagctcat tcacttctat tcagtcaaaa tgtttgatta 1200
tctggaaaat gaggaggtgg ctctcgatga acttaaacag atgttgagag atagagatcc 1260
taatgatacc aggaaccaat tcaagaataa tgctctacat gcataccttt tcaatgagca 1320
ctgtaataat gttgaggttg tcaaactact actagacagt ggtactaatc cattacacaa 1380
aaattggaga cagcttactc cattagggga atacacaaat agtagacatg gtaaagttaa 1440

-continued

```
taaggatata gcgatggttc tactagaagc tactggatat agcaacataa atgactttaa   1500
tatattcacc tatatgaaat ccaaaaatgt agatattgac ttgataaagg tattggtaga   1560
acatggattt gattttagtg ttaaatgcga aaaacatcat tcagttatag aaaattatgt   1620
aatgacagat gatcctgttc ctgaaattat tgatttattc atagaaaatg gatgcagtgt   1680
tatttatgag gacgaggatg atgagtacgg atacgcgtat gaagaatatc actcacaaaa   1740
tgacgattat caaccacgaa attgcggtac agtattacat ctgtatatca tctctcatct   1800
gtattcagag tcggattcga gatcatgtgt gaacccggaa gttgttaaat gtctgattaa   1860
tcatggaatc aacccatctt ctatagataa aaactattgt acagctcttc aatattatat   1920
taagtcatct catatagata tagacatcgt taaattgtta atgaaaggaa tagataacac   1980
ggcttattca tatatagacg atctaacatg ttgtactcga ggaattatgg ctgattatct   2040
aaatagtgat tatagataca ataaagatgt agatttagat ttggtcaaat tgtttttgga   2100
gaatggaaaa ccgcacggaa taatgtgtag tattgtacca ctatggagaa atgataagga   2160
aaccatctct ttgatattga aaacaatgaa ctcggatgtc ctccaacata tactaattga   2220
gtatataaca ttcagcgata tcgatatctc tctagtggaa tacatgttgg aatatggagc   2280
tgtggtaaat aaagaggcta ttcacggata ctttaaaaat attaatattg attcttacac   2340
gatgaaatat ctactaaaaa aggaaggggg agatgccgtc aatcatctcg atgatggaga   2400
gatcccgatt ggacacctat gtaaatccaa ctatggacgt tataatttct acactgatac   2460
atacagacag ggttttcgtg atatgtctta tgcttgccca attcttagta ctataaacat   2520
ttgcctacct tatcttaaag acattaacat gattgacaaa cgaggagaaa cacttcttca   2580
caaggctgtt agatataata aacaatctct agtgtcttta ctgctagaat ccggttcaga   2640
tgtcaacatt agatcaaata acggatatac atgtatagcc attgcaatca acgaatctag   2700
aaacattgaa ctgctgaaca tgctattatg tcataaacct acattagatt gtgtgattga   2760
ttcattgaga gaaatatcta acatagtaga taatgcctat gctataaaac aatgtattag   2820
atatgccatg attatagatg actgtatatc gtctaagatt ccagagtcca taagtaaaca   2880
ctataatgat tatatagata tttgcaatca agaattgaac gagatgaaaa aaataatagt   2940
gggaggcaac actatgttct cattaatatt tactgatcat ggagctaaaa ttattcatcg   3000
gtatgccaat aatccagaat tacgtgcgta ttatgagtca aaacaaaata aaatatacgt   3060
ggaagtatat gatattattt ccaatgcgat agtgaagcat aataaaattc ataaaaacat   3120
agaatcagtt gatgacaata cctacatttc taatttgcct tataccatca aatacaaaat   3180
attcgagcaa caataagtat tttttatcaa aaaattgaaa ttttattttt tttttttgga   3240
atataaataa tatggatagc actgagaacg tcatcaagcc cttcatgcgc ttcaaggtgc   3300
acatggaggg ctccgtgaac ggccacgagt tcgagatcga gggcgagggc gagggcaagc   3360
cctacgaggg cacccagacc gccaagctgc aggtgaccaa gggcggcccc ctgcccttcg   3420
cctgggacat cctgtccccc cagttccagt acggctccaa ggtgtacgtg aagcaccccg   3480
ccgacatccc cgactacaag aagctgtcct tccccgaggg cttcaagtgg gagcgcgtga   3540
tgaacttcga ggacggcggc gtggtgaccg tgacccagga ctcctcactg caggacggca   3600
ccttcatcta ccacgtgaag ttcatcggcg tgaacttccc ctccgacggc cccgtaatgc   3660
agaagaagac tctgggctgg gagccctcca ccgagcgcct gtacccccgc gacggcgtgc   3720
tgaagggcga gatccacaag gcgctgaagc tgaagggcgg cggccactac ctggtggagt   3780
```

-continued

```
tcaagtcaat ctacatggcc aagaagcccg tgaagctgcc cggctactac tacgtggact   3840
ccaagctgga catcacctcc cacaacgagg actacaccgt ggtggagcag tacgaacgcg   3900
ccgaggcccg ccaccacctg ttccagtagt tttatattt aaatgcgcgc aataatggaa    3960
caagaaccct aacttttaac tttacaccaa agatattctt taggccgaca actattacgg   4020
ccaatgtatc tagggggaaa gataaactat ctgttcgagt agtttattcc accatggatg   4080
tcaaccatcc aatctattat gtacaaaaac aattggtagt tgtatgtaat gacctgtata   4140
aggtatctta cgatcaaggg gtaagtatta ccaagattat gggagataat aactaataat   4200
aatgaaaaca aactatagag ttgtaaatgg atgaaattgt aaaaaaatatc cgggagggaa  4260
cgcatgtcct tcttccattt tatgaaacat tgccagaact taatctgtct ctaggtaaaa   4320
gcccattacc tagtctggaa tacggagcta attactttct tcagatttct agagttaatg   4380
atctaaatag aatgccgacc gacatgttaa aactttttac acatgatatc atgttaccag   4440
aaagcgatct agataaagtc tatgaaattt taaagattaa tagcgtaaag tattatggga   4500
ggagtactaa agcggacgcc gtagttgccg acctcagcgc gatcctctag agtcgacctg   4560
caggcatgca agcttggcgt aatcatggtc atagctgttt cctgtgtgaa attgttatcc   4620
gctcacaatt ccacacaaca tacgagccgg aagcataaag tgtaaagcct ggggtgccta   4680
atgagtgagc taactcacat taattgcgtt gcgctcactg cccgctttcc agtcgggaaa   4740
cctgtcgtgc cagctgcatt aatgaatcgg ccaacgcgcg gggagaggcg gtttgcgtat   4800
tgggcgctct tccgcttcct cgctcactga ctcgctgcgc tcggtcgttc ggctgcggcg   4860
agcggtatca gctcactcaa aggcggtaat acggttatcc acagaatcag gggataacgc   4920
aggaaagaac atgtgagcaa aaggccagca aaaggccagg aaccgtaaaa aggccgcgtt   4980
gctggcgttt ttccataggc tccgcccccc tgacgagcat cacaaaaatc gacgctcaag   5040
tcagaggtgg cgaaacccga caggactata aagataccag gcgtttcccc ctggaagctc   5100
cctcgtgcgc tctcctgttc cgaccctgcc gcttaccgga tacctgtccg cctttctccc   5160
ttcgggaagc gtggcgcttt ctcatagctc acgctgtagg tatctcagtt cggtgtaggt   5220
cgttcgctcc aagctgggct gtgtgcacga accccccgtt cagcccgacc gctgcgcctt   5280
atccggtaac tatcgtcttg agtccaaccc ggtaagacac gacttatcgc cactggcagc   5340
agccactggt aacaggatta gcagagcgag gtatgtaggc ggtgctacag agttcttgaa   5400
gtggtggcct aactacggct acactagaag gacagtattt ggtatctgcg ctctgctgaa   5460
gccagttacc ttcggaaaaa gagttggtag ctcttgatcc ggcaaacaaa ccaccgctgg   5520
tagcggtggt ttttttgttt gcaagcagca gattacgcgc agaaaaaaag gatctcaaga   5580
agatcctttg atcttttcta cggggtctga cgctcagtgg aacgaaaact cacgttaagg   5640
gattttggtc atgagattat caaaaaggat cttcacctag atccttttaa attaaaaatg   5700
aagttttaaa tcaatctaaa gtatatatga gtaaacttgg tctgacagtt accaatgctt   5760
aatcagtgag gcacctatct cagcgatctg tctatttcgt tcatccatag ttgcctgact   5820
ccccgtcgtg tagataacta cgatacggga gggcttacca tctggcccca gtgctgcaat   5880
gataccgcga gacccacgct caccggctcc agatttatca gcaataaacc agccagccgg   5940
aagggccgag cgcagaagtg gtcctgcaac tttatccgcc tccatccagt ctattaattg   6000
ttgccgggaa gctagagtaa gtagttcgcc agttaatagt ttgcgcaacg ttgttgccat   6060
tgctacaggc atcgtggtgt cacgctcgtc gtttggtatg gcttcattca gctccggttc   6120
ccaacgatca aggcgagtta catgatcccc catgttgtgc aaaaaagcgg ttagctcctt   6180
```

cggtcctccg atcgttgtca gaagtaagtt ggccgcagtg ttatcactca tggttatggc 6240
agcactgcat aattctctta ctgtcatgcc atccgtaaga tgcttttctg tgactggtga 6300
gtactcaacc aagtcattct gagaatagtg tatgcggcga ccgagttgct cttgcccggc 6360
gtcaatacgg gataataccg cgccacatag cagaacttta aaagtgctca tcattggaaa 6420
acgttcttcg gggcgaaaac tctcaaggat cttaccgctg ttgagatcca gttcgatgta 6480
acccactcgt gcacccaact gatcttcagc atcttttact ttcaccagcg tttctgggtg 6540
agcaaaaaca ggaaggcaaa atgccgcaaa aaagggaata agggcgacac ggaaatgttg 6600
aatactcata ctcttccttt ttcaatatta ttgaagcatt tatcagggtt attgtctcat 6660
gagcggatac atatttgaat gtatttagaa aaataaacaa ataggggttc cgcgcacatt 6720
tccccgaaaa gtgccacctg acgtctaaga aaccattatt atcatgacat taacctataa 6780
aaataggcgt atcacgaggc cctttcgtc 6809

<210> SEQ ID NO 23
<211> LENGTH: 11161
<212> TYPE: DNA
<213> ORGANISM: Artificial Sequence
<220> FEATURE:
<223> OTHER INFORMATION: Description of Artificial Sequence: Synthetic
pLL19 Tagged-D13L-CHO codon optimised transposon mediated
transducing vector sequence for integration into cellular
nuclear genomic DNA

<400> SEQUENCE: 23
tcagaattgg ttaattggtt gtaacactga cccctatttg tttatttttc taaatacatt 60
caaatatgta tccgctcatg agacaataac cctgataaat gcttcaataa tattgaaaaa 120
ggaagaatat gagccatatt caacgggaaa cgtcgaggcc gcgattaaat tccaacatgg 180
atgctgattt atatgggtat aaatgggctc gcgataatgt cgggcaatca ggtgcgacaa 240
tctatcgctt gtatgggaag cccgatgcgc cagagttgtt tctgaaacat ggcaaaggta 300
gcgttgccaa tgatgttaca gatgagatgg tcagactaaa ctggctgacg gaatttatgc 360
cacttccgac catcaagcat tttatccgta ctcctgatga tgcatggtta ctcaccactg 420
cgatccccgg aaaaacagcg ttccaggtat tagaagaata tcctgattca ggtgaaaata 480
ttgttgatgc gctggcagtg ttcctgcgcc ggttgcactc gattcctgtt tgtaattgtc 540
cttttaacag cgatcgcgta tttcgcctcg ctcaggcgca atcacgaatg aataacggtt 600
tggttgatgc gagtgatttt gatgacgagc gtaatggctg gcctgttgaa caagtctgga 660
aagaaatgca taaacttttg ccattctcac cggattcagt cgtcactcat ggtgatttct 720
cacttgataa ccttattttt gacgagggga aattaatagg ttgtattgat gttggacgag 780
tcggaatcgc agaccgatac caggatcttg ccatcctatg gaactgcctc ggtgagtttt 840
ctccttcatt acagaaacgg ctttttcaaa aatatggtat tgataatcct gatatgaata 900
aattgcagtt tcatttgatg ctcgatgagt ttttctaact catgaccaaa atcccttaac 960
gtgagttacg cgcgcgtcgt tccactgagc gtcagacccc gtagaaaaga tcaaaggatc 1020
ttcttgagat cctttttttc tgcgcgtaat ctgctgcttg caaacaaaaa aaccaccgct 1080
accagcggtg gtttgtttgc cggatcaaga gctaccaact ctttttccga aggtaactgg 1140
cttcagcaga gcgcagatac caaatactgt tcttctagtg tagccgtagt tagcccacca 1200
cttcaagaac tctgtagcac cgcctacata cctcgctctg ctaatcctgt taccagtggc 1260
tgctgccagt ggcgataagt cgtgtcttac cgggttggac tcaagacgat agttaccgga 1320

-continued

```
taaggcgcag cggtcgggct gaacgggggg ttcgtgcaca cagcccagct tggagcgaac   1380
gacctacacc gaactgagat acctacagcg tgagctatga gaaagcgcca cgcttcccga   1440
agggagaaag gcggacaggt atccggtaag cggcagggtc ggaacaggag agcgcacgag   1500
ggagcttcca gggggaaacg cctggtatct ttatagtcct gtcgggtttc gccacctctg   1560
acttgagcgt cgatttttgt gatgctcgtc aggggggcgg agcctatgga aaaacgccag   1620
caacgcggcc tttttacggt tcctggcctt ttgctggcct tttgctcaca tgttctttcc   1680
tgcgttatcc cctgattctg tggataaccg tattaccgcc tttgagtgag ctgataccgc   1740
tctcaatatt ggccattagc catattattc attggttata tagcataaat caatattggc   1800
tattggccat tgcatacgtt gtatctatat cataatatgt acatttatat tggctcatgt   1860
ccaatatgac cgccatgttg gcattgatta ttgactagtt attaatagta atcaattacg   1920
gggtcattag ttcatagccc atatatggag ttccgcgtta cataacttac ggtaaatggc   1980
ccgcctggct gaccgcccaa cgacccccgc ccattgacgt caataatgac gtatgttccc   2040
atagtaacgc caatagggac tttccattga cgtcaatggg tggagtattt acggtaaact   2100
gcccacttgg cagtacatca agtgtatcat atgccaagtc cgccccctat tgacgtcaat   2160
gacggtaaat ggcccgcctg gcattatgcc cagtacatga ccttacggga ctttcctact   2220
tggcagtaca tctacgtatt agtcatcgct attaccatgc tgatgcggtt ttggcagtac   2280
accaatgggc gtggatagcg gtttgactca cggggatttc caagtctcca ccccattgac   2340
gtcaatggga gtttgttttg gcaccaaaat caacgggact ttccaaaatg tcgtaataac   2400
cccgccccgt tgacgcaaat gggcggtagg cgtgtacggt gggaggtcta tataagcaga   2460
gctcgtttag tgaaccgtca gatcactaga agctttattg cggtagttta tcacagttaa   2520
attgctaacg cagtcaggcc aacatgggct ctagcctgga cgacgagcac atcctgagcg   2580
ccctgctgca gagcgacgac gaactggtgg gcgaggacag cgacagcgag gtcagcgacc   2640
acgtgtccga ggacgacgtg cagtccgaca ccgaggaagc cttcatcgac gaggtgcacg   2700
aagtgcagcc taccagcagc ggctccgaga tcctggacga gcagaacgtg atcgagcagc   2760
ctggcagctc cctggccagc aacagaatcc tgaccctgcc ccagagaacc atcagaggca   2820
agaacaagca ctgctggtcc acctccaaga gcaccaggcg gagcagagtg tccgccctga   2880
acatcgtgcg gagccagagg ggccccacca gaatgtgcag aaacatctac gacccccctgc  2940
tgtgcttcaa gctgttcttc accgacgaga tcatcagcga gatcgtgaag tggaccaacg   3000
ccgagatcag cctgaagagg cgggagagca tgaccagcgc caccttcaga gacaccaacg   3060
aggacgagat ctacgccttc ttcggcatcc tggtgatgac cgccgtgaga aaggacaacc   3120
acatgagcac cgacgacctg ttcgacagat ccctgagcat ggtgtacgtg tccgtgatga   3180
gcagagacag attcgacttc ctgatcagat gcctgagaat ggacgacaag agcatcagac   3240
ccaccctgcg ggagaacgac gtgttcaccc ccgtgcggaa gatctgggac ctgttcatcc   3300
accagtgcat ccagaactac acccctggcg cccacctgac catcgatgag cagctgctgg   3360
gcttcagagg cagatgcccc ttcagagtgt acatccccaa caagcccagc aagtacggca   3420
tcaagatcct gatgatgtgc gacagcggca ccaagtacat gatcaacggc atgccctacc   3480
tgggcagagg cacccagaca aacggcgtgc ccctgggcga gtactacgtg aaagaactga   3540
gcaagcctgt gcatggcagc tgcaggaaca tcacatgcga caactggttc accagcatcc   3600
ccctggccaa gaacctcctg caggaaccct acaagctgac catcgtgggc accgtgcgga   3660
```

-continued

```
gcaacaagcg ggagatccca gaggtgctga agaacagcag atccagacct gtgggaacaa   3720
gcatgttctg cttcgacggc cccctgaccc tggtgtccta caagcccaag cccgccaaga   3780
tggtgtacct cctgtccagc tgcgacgagg acgccagcat caacgagagc accggcaagc   3840
cccagatggt gatgtactac aaccagacca agggcggcgt ggacaccctg gaccagatgt   3900
gcagcgtgat gacatgcagc agaaagacca acagatggcc tatggccctg ctgtacggca   3960
tgatcaatat cgcctgcatc aacagcttca tcatctacag ccacaacgtg tccagcaagg   4020
gcgagaaggt gcagagccgg aagaaattca tgcggaacct gtacatgagc ctgacctcca   4080
gcttcatgag aaagagactg gaagccccca ccctgaagag atacctccgg gacaacatca   4140
gcaacatcct gcccaaggaa gtgccaggaa caagcgacga cagcaccgag gaacccgtga   4200
tgaagaagag gacctactgc acctactgtc ccagcaagat cagaagaaag gccaacgcca   4260
gctgcaagaa atgcaaaaaa gtgatctgcc gggagcacaa catcgacatg tgccagagct   4320
gtttctgatt cagacatgat aagatacatt gatgagtttg gacaaaccac aactagaatg   4380
cagtgaaaaa aatgctttat ttgtgaaatt tgtgatgcta ttgctttatt tgtaaccatt   4440
ataagctgca ataaacaagt taacaacaac aattgcattc attttatgtt tcaggttcag   4500
ggggagatgt gggaggtttt ttaaagcaag taaaacctct acaaatgtgg taagcaggtt   4560
taaccctaga aagatagtct gcgtaaaatt gacgcatgca ttcttgaaat attgctctct   4620
ctttctaaat agcgcgaatc cgtcgctgtg catttaggac atctcagtcg ccgcttggag   4680
ctcccgtgag gcgtgcttgt caatgcggta agtgtcactg attttgaact ataacgaccg   4740
cgtgagtcaa aatgacgcat gattatcttt tacgtgactt ttaagattta actcatacga   4800
taattatatt gttatttcat gttctactta cgtgataact tattatatat atattttctt   4860
gttatagata tctttcttta tgttttaaat gcactgacct cccacattcc ctttttagta   4920
aaatattcag aaataattta aatacatcat tgcaatgaaa ataaatgttt tttattaggc   4980
agaatccaga tgctcaaggc ccttcataat atcccccagt ttagtagttg gacttaggga   5040
acaaaggaac ctttaataga aattggacag caagaaagcg agtcagaaga actcgtcaag   5100
aaggcgatag aaggcgatgc gctgcgaatc gggagcggcg ataccgtaaa gcacgaggaa   5160
gcggtcagcc cattcgccgc caagttcttc agcaatatca cgggtagcca acgctatgtc   5220
ctgatagcgg tccgccacac ccagccggcc acagtcgatg aatccagaaa agcggccatt   5280
ttccaccatg atattcggca agcaggcatc gccatgggtc acgacgagat cctcgccgtc   5340
gggcatgcgc gccttgagcc tggcgaacag ttcggctggc gcgagcccct gatgttcttc   5400
gtccagatca tcctgatcga caagaccggc ttccatccga gtacgtgctc gctcgatgcg   5460
atgtttcgct tggtggtcga atggacaggt agccggatca agcgtatgca gccgccgcat   5520
tgcatcagcc atgatggata ctttctcggc aggagcaagg tgagatgaca ggagatcctg   5580
ccccggcact tcgcccaata gcagccagtc ccttcccgct tcagtgacaa cgtcgagcac   5640
agctgcgcaa ggaacgcccg tcgtggccag ccacgatagc cgcgctgcct cgtcctgcag   5700
ttcattcagg gcaccggaca ggtcggtctt gacaaaaaga accgggcgcc cctgcgctga   5760
cagccggaac acggcggcat cagagcagcc gattgtctgt tgtgcccagt catagccgaa   5820
tagcctctcc acccaagcgg ccggagagcc tgcgtgcaat ccatcttgtt caatcatggt   5880
ggcggacgaa aggcccggag atgaggaaga ggagaacagc gcggcagacg tgcgcttttg   5940
aagcgtgcag aatgccgggc ctccggagga ccttcgggcg cccgccccgc ccctgagccc   6000
gcccctgagc ccgcccccgg acccacccct tcccagcctc tgagcccaga aagcgaagga   6060
```

-continued

```
gcaaagctgc tattggccgc tgccccaaag gcctacccgc ttccattgct cagcggtgct   6120
gtccatctgc acgagactag tgagtcgtgc tacttccatt tgtcacgtcc tgcacgacgc   6180
gagctgcggg gcggggggga acttcctgac taggggagga gtagaaggtg gcgcgaaggg   6240
gccaccaaag aacggagccg gttggcgcct accggtggat gtggaatgtg tgcgaggcca   6300
gaggccactt gtgtagcgcc aagtgcccag cggggctgct aaagcgcatg ctccagactg   6360
ccttgggaaa agcgcctccc ctacccggta gagaaacttg atctgtcgcc gcaattcaag   6420
cttcgtgagg ctccggtgcc cgtcagtgac ctgctatact ctggagacgg cacatcgccc   6480
acagtccccg agaagttggg aggggtcggc aattgaaccg gtgcctagag aaggtggcgc   6540
ggggtaaact gggaaagtga tgtcgtgtac tggctccgcc tttttcccga gggtggggga   6600
gaaccgtata taagtgcagt agtcgccgtg aacgttcttt ttcgcaacgg gtttgccgcc   6660
agaacacagg taagtgccgt gtgtggttcc cgcgggcctg gcctctttac gggttatggc   6720
ccttgcgtgc cttgaattac ttccacctgg ctccagtacg tgattcttga tcccgagctg   6780
gagccagggg cgggccttgc gctttaggag ccccttcgcc tcgtgcttga gttgaggcct   6840
ggcctgggcg ctggggccgc cgcgtgcgaa tctggtggca ccttcgcgcc tgtctcgctg   6900
ctttcgataa gtctctagcc atttaaaatt tttgatgacg tgctgcgacg ctttttttct   6960
ggcaagatag tcttgtaaat gcgggccagg atctgcacac tggtatttcg gtttttgggc   7020
ccgcggccgg cgacggggcc cgtgcgtccc agcgcacatg ttcggcgagg cggggcctgc   7080
gagcgcggcc accgagaatc ggacgggggt agtctcaagc tggccggcct gctctggtgc   7140
ctggcctcgc gccgccgtgt atcgccccgc cctgggcggc aaggctggcc cggtcggcac   7200
cagttgcgtg agcggaaaga tggccgcttc ccggccctgc tccagggggc tcaaaatgga   7260
ggacgcggcg ctcgggagag cgggcgggtg agtcacccac acaaaggaaa agggcctttc   7320
cgtcctcagc cgtcgcttca tgtgactcca cggagtaccg ggcgccgtcc aggcacctcg   7380
attagttctg gagcttttgg agtacgtcgt ctttaggttg gggggagggg ttttatgcga   7440
tggagtttcc ccacactgag tgggtggaga ctgaagttag gccagcttgg cacttgatgt   7500
aattctcctt ggaatttggc ctttttgagt ttggatcttg gttcattctc aagcctcaga   7560
cagtggttca aagttttttt cttccatttc aggtgtcgtg aacacgtctc ggggggccgc   7620
cacccatgaa caacaccatc atcaactccc tgatcggcgg cgacgactcc atcaagcggt   7680
ccaacgtgtt cgccgtggac tcccagatcc ccaccctgta catgccccag tacatctccc   7740
tgtccggcgt gatgaccaac gacggccctg acaaccaggc tatcgcctcc ttcgagatcc   7800
gggatcagta catcaccgcc ctgaaccacc tggtgctgtc cctggaactg cccgaagtga   7860
agggcatggg cagattcggc tacgtgccct acgtgggcta caagtgcatc aaccacgtgt   7920
ccatctccag ctgcaacggc gtgatctggg aaatcgaggg cgaggaactg tacaacaact   7980
gcattaacaa cacaatcgcc ctgaagcact ccggctactc ctccgagctg aacgacatct   8040
ccatcggcct gacccccaac gacaccatca aagaaccctc caccgtgtac gtgtacatca   8100
agacccccct cgacgtggaa gataccttct ccagcctgaa gctgtccgac tccaagatca   8160
ccgtgaccgt gaccttcaac cctgtgtccg acatcgtgat ccgggactcc agcttcgact   8220
tcgagacatt caacaaagaa tttgtgtacg tgcccgagct gtccttcatc ggctacatgg   8280
tcaagaacgt gcagatcaag cccagcttca tcgagaagcc tcggagagtg atcggccaga   8340
tcaaccagcc taccgccacc gtgacagagg tgcacgccgc cacatccctg agcgtgtaca   8400
```

-continued

```
ccaagcccta ctacggcaac accgacaaca agttcatctc ctaccccggc tacagccagg   8460
acgagaagga ctacatcgac gcctacgtgt cccggctgct ggacgacctc gtgatcgtgt   8520
ctgatggccc ccctaccggc taccctgagt ctgccgagat cgtggaagtg cccgaggacg   8580
gcatcgtcag catccaggac gccgatgtgt atgtgaagat cgacaacgtg ccagacaaca   8640
tgtccgtgta cctgcacacc aacctgctga tgttcggcac ccggaagaat tccttcatct   8700
acaacatctc caagaagttc tccgccatca ccggcaccta ctccgacgcc accaagcgga   8760
ccatcttcgc ccacatctcc cacagcatca acatcatcga cacctccatc cccgtgtccc   8820
tgtggacctc tcagagaaac gtgtacaacg gcgacaacag atccgccgag tccaaggcca   8880
aggacctgtt catcaacgac cccttcatca agggcatcga cttcaagaac aagaccgaca   8940
tcatctcccg gctggaagtg cgcttcggca acgacgtgct gtactccgag aacggcccta   9000
tcagccggat ctacaacgag ctgctgacca agtccaacaa cggcaccaga accctgacct   9060
ttaactttac ccccaagatc ttcttccggc ccaccaccat caccgctaac gtgtccagag   9120
gcaaggacaa gctgagcgtg cgggtggtgt actccaccat ggacgtgaac caccccatct   9180
actacgtgca gaaacagctg gtggtcgtgt gcaacgatct gtacaaggtg tcctacgacc   9240
agggcgtgtc cattaccaag atcatgggcg ataacaacga ctacaaggac gacgacgaca   9300
agtgaaaaag cgtcttcctg ttctcatcac atcatatcaa ggttatatac catcaatatt   9360
gccacagatg ttacttagcc ttttaatatt tctctaattt agtgtatatg caatgatagt   9420
tctctgattt ctgagattga gtttctcatg tgtaatgatt atttagagtt tctctttcat   9480
ctgttcaaat ttttgtctag ttttattttt tactgatttg taagacttct ttttataatc   9540
tgcatattac aattctcttt actggggtgt tgcaaatatt ttctgtcatt ctatggcctg   9600
acttttctta atggtttttt aattttaaaa ataagtctta atattcatgc aatctaatta   9660
acaatctttt ctttgtggtt aggactttga gtcataagaa atttttctct acactgaagt   9720
catgatggca tgcttctata ttattttcta aaagatttaa agttttgcct tctccattta   9780
gacttataat tcactggaat ttttttgtgt gtatggtatg acatatgggt tccctttttat  9840
tttttacata taaatatatt tccctgtttt tctaaaaaag aaaaagatca tcattttccc   9900
attgtaaaat gccatatttt tttcataggt cacttacata tatcaatggg tctgtttctg   9960
agctctactc tattttatca gcctcactgt ctatccccac acatctcatg ctttgctcta  10020
aatcttgata tttagtggaa cattctttcc cattttgttc tacaagaata tttttgttat  10080
tgtctttggg ctttctatat acattttgaa atgaggttga caagttaata atcaacctct  10140
ggattacaaa atttgtgaaa gattgactgg tattcttaac tatgttgctc cttttacgct  10200
atgtggatac gctgctttaa tgcctttgta tcatgctatt gcttcccgta tggctttcat  10260
tttctcctcc ttgtataaat cctggttgct gtctctttat gaggagttgt ggcccgttgt  10320
caggcaacgt ggcgtggtgt gcactgtgtt tgctgacgca acccccactg gttggggcat  10380
tgccaccacc tgtcagctcc tttccgggac tttcgctttc cccctcccta ttgccacggc  10440
ggaactcatc gccgcctgcc ttgcccgctg ctggacaggg gctcggctgt tgggcactga  10500
caattccgtg gtgttgtcgg ggaaatcatc gtcctttcct tggctgctcg cctgtgttgc  10560
cacctggatt ctgcgcggga cgtccttctg ctacgtccct tcggccctca atccagcgga  10620
ccttccttcc cgcggcctgc tgccggctct gcggcctctt ccgcctcttc gccttcgccc  10680
tcagacgagt cggatctccc tttgggccgc ctccccgcat cgcctgctat tgtcttgcca  10740
atcctccccc ttgctgtcct gccccacccc accccccaga atagaatgac acctactcag  10800
```

-continued

```
acaatgcgat gcaatttcct cattttatta ggaaaggaca gtgggagtgg caccttccag  10860
ggtcaaggaa ggcacggggg aggggcaaac aacagatggc tggcaactag aaggcacatt  10920
tgttacttta tagaagaaat tttgagtttt tgtttttttt taataaataa ataaacataa  10980
ataaattgtt tgttgaattt attattagta tgtaagtgta aatataataa aacttaatat  11040
ctattcaaat taataaataa acctcgatat acagaccgat aaaacacatg cgtcaatttt  11100
acgcatgatt atctttaacg tacgtcacaa tatgattatc tttctagggt taagaagact  11160
g                                                                  11161
```

VIRAL VECTOR MANUFACTURE

RELATED APPLICATIONS

This application is the U.S. National Phase under 35 U.S.C. § 371 of International Patent Application No. PCT/AU2014/050330, filed on Nov. 3, 2014, which in turn is associated with and claims priority from Australian patent application no. 2013904242 filed on Nov. 1, 2013 and Australian patent application no. 2014900370 filed on Feb. 7, 2014, the entire contents of each of these applications are incorporated herein by reference.

SEQUENCE LISTING

The instant application contains a Sequence Listing which has been submitted electronically in ASCII format and is hereby incorporated by reference in its entirety. Said ASCII copy, created on Sep. 30, 2016, is named 052392-0021_SL.txt and is 72,814 bytes in size.

FIELD OF THE INVENTION

The present invention relates to the development of cells and cell lines suitable for propagating and therefore manufacturing poxvirus-based medicaments. In particular, the specification relates to recombinant modified cellular substrates for propagating such poxviruses for the manufacture of therapeutic or prophylactic agents.

BACKGROUND

Bibliographic details of references in the subject specification are listed at the end of the specification.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All publications mentioned in this specification are herein incorporated by reference in their entirety.

The pox virus family comprises two subfamilies, the Chordopoxvirinae and the Entomopoxvirinae. The Chordopoxvirinae comprises eight genera including the Orthopoxviridae comprising species which infect man (for example, variola virus, the causative agent of smallpox, cowpox virus (which formed the original smallpox vaccine reported by Jenner in 1796), vaccinia virus (used as a second generation smallpox vaccine) and monkeypox virus), and the Avipoxviridae viruses comprising species that infect birds, such as fowlpox and canarypox viruses. In addition to their use as antigens in smallpox vaccines, there is much interest in the use of recombinant vaccinia-based viruses and avipox viruses as a "backbone" vectors. As intra-cytoplasmic vectors, the Orthopoxviridae are able inter alfa to deliver foreign antigens to the host cytoplasm and antigen processing pathways that process antigens to peptides for presentation on the cell surface. Such vectors expressing foreign antigens are used in the development of vaccines for diseases such as AIDS, tuberculosis, malaria and cancer which have proven difficult to treat by other vaccination strategies.

The Chordopoxvirinae have linear double-stranded DNA genomes ranging in size from 130 kb in parapoxviruses to over 300 kb in avipoxviruses and their life cycle in the host is spent entirely in the host cell cytoplasm. The poxviruses operate substantially independently of their host cell and host cell molecules, especially for processes involved in early mRNA synthesis. However, host molecules appear to be used for the initiation or termination of intermediate and late viral transcription. The poxviruses produce structurally diverse "host range factors" which specifically target and manipulate host signaling pathways to permit cellular conditions allowing viral replication. Most poxviruses can bind and infect mammalian cells, but whether or not the subsequent infection is permissive (able to produce infectious virions) or non-permissive (substantially unable to produce infectious virions) is dependent upon the specific poxvirus and specific cell type involved. There is currently a relatively poor understanding at the molecular level of pox virus-host interactions, in particular host-range genes, and which factors are necessary to modulate the relationship to facilitate both viral and cellular propagation. For a review of host range genes reference may be made to Werden et al. 2008 incorporated herein in its entirety.

Observations on strains of vaccinia relevant to their use as small pox vaccines and subsequently as viral vectors, have been published from the early 1960's through to the present day. Certain strains of vaccinia, including strains employed as small pox vaccines, are able to propagate in human cells and therefore represent health risks, such as the development of viral encephalitis. With a view to developing a safer vaccine, a vaccinia strain from Ankara (referred to as "CVA") was passaged more than 500 times in non-human cells. During this process the vaccinia genome changed substantially involving the development of at least six major deletions compared to the original CVA genome. The modified virus was less pathogenic in man but still able to engender a protective immune response. This attenuated vaccinia virus is referred to as MVA (Modified Vaccinia Ankara) and is also categorized by passage number, as viruses with different passage numbers were found to be genetically and phenotypically distinct. However, by passage number 515 MVA515 was understood to be genetically stable. In the early 1990s, it was observed that MVA strains, such MVA572, and its derivative, MVA F6 were able to express vaccinia proteins and heterologous (recombinant) proteins at high levels in non-permissive cells (in which the virus will not propagate), enabling the development of MVA as a vector for heterologous molecules of interest, such as those encoding antigens for vaccine or therapy delivery.

More recently, attempts have been made to produce a modified vaccinia virus with the qualities of MVA by introducing the six large known deletions of MVA into CVA. Interestingly, this did not result in a virus with the attenuated qualities of MVA. It was proposed that the absence of host range genes might be responsible for the observed attenuation, however this has not been substantiated (see for example, Meyer et al., *Journal of General Virology* (1991) 72:1031-1038.

The poxviruses constitute a large family of viruses characterized by a large, linear dsDNA genome, a cytoplasmic site of propagation and a complex virion morphology. Vaccinia virus is the representative virus of this group of virus and the most studied in terms of viral morphogenesis. Vaccinia virus virions appear as "brick shaped" or "ovoid" membrane-bound particles with a complex internal structure featuring a walled, biconcave core flanked by "lateral bodies". The virion assembly pathway involves a fabrication of membrane containing crescents which develop into immature virions (IVs), and then evolve into mature virions (MVs). Over 70 specific gene products are contained within the vaccinia virus virion, where the effects of mutations in over 50 specific genes on vaccinia virus assembly are now described.

Vaccinia virus enter cells by fusion of its surface membranes with the plasma membrane of the host cell, releasing the core (and lateral bodies) into the cytoplasm and activating the virus' transcriptional program. The virion cores contain the full complement of virus-coded enzymes required for synthesis and modification of early mRNA. Early genes encode enzymes required for DNA propagation, and thus as early gene expression peaks, viral DNA propagation ensues in cytoplasmic sites termed "factories." Early genes also encode intermediate transcription factors, and intermediate genes, in turn, encode late transcription factors, so that intermediate and late genes are expressed in succession after the prerequisite initiation of viral DNA propagation. Thus, the full complement of viral genes are transcribed in a temporal cascade, with the early, intermediate and late classes being distinguished by class-specific transcriptional promoters and virally encoded transcription factors. Furthermore, only propagated genomes are competent templates for intermediate and late transcription. These two classes of genes together encode virion structural proteins, virion enzymes, and assembly factors and are required for assembly of new progeny virus particles.

Shortly after viral uptake and early expression infection-specific cytoplasmic domains form within the cell that are uniform in density and are sometimes surrounded by endoplasmic reticulum (ER) derived cisternae which increase in size with time. These domains represent sites of viral DNA propagation and are often called "viral factories".

Viral assembly starts with the formation of rigid crescent-shaped structures (cupules in three dimensions) within the viral factories. In high resolution electron micrographs the outer layer of these crescent shaped structures are composed of regularly spaced projections termed "spicules". Crescents apparently grow in length while maintaining the same curvature until they become closed circles (spheres in three dimensions) called immature virions (IV). IV are filled with "viroplasm" material that is uniform in density but discernibly more electron dense than the surrounding factory. As the IVs form uptake of encapsidated DNA also takes place: these are seen in electron micrographs as electron dense, round or ovoid subdomain within the IVs called a "nucleoid". IVs that contain nucleoids of condensed DNA that are often referred to as "IVN." Maturation of several virion protein precursors via proteolytic cleavage is required for the morphogenesis of IVN to mature virions (MV). The majority of mature virions are found outside factories and may exist in clusters either at the periphery of a factory or apparently separated by a significant distance from the nearest factory.

Poxvirus virions exist in three infectious forms: mature virions (MV), wrapped virions (WV), and extracellular virions (EV). MV, the simplest form of the virus, are membraned particles containing a biconcave, DNA-containing core flanked by lateral bodies, which fill the concavities of the core. MV are normally found exclusively inside cells and are liberated only by cell lysis. WV consist of MV which are surrounded by two additional lipid bilayers derived from trans-Golgi cisternae. WV, whose outer membranes contain characteristic viral proteins, are precursors of EV and are also found within the cell. EV consist of WV which have been exocytosed via fusion of the outermost WV membrane with the plasma membrane, leaving an MV wrapped in one additional membrane. A fraction of EV are found attached to the cell surface, while some are found free in the extracellular medium. EV are thought to be important for spread of the virus within an organism.

Removal of essential genes from viruses and complementation in host cells is know in the art as a general proposed strategy for generating safe and effective viral vectors for treatment and therapy. There is a need for improved attenuated orthopox vectors with enhanced safety, expression and/or immunogenicity and a commensurate need for methods of propagating and manufacturing such orthopox vectors safely and economically.

A number of mammalian cell lines are used for the manufacture of recombinant proteins for research purposes. These include, rabbit, hamster, primate and human derived cell lines such as, without limitation, and as known in the art, HEK293, 293T, 143B, CHO, HeLa, Vero and BHK, HepG2, and 3T3 cells. Notably, however, the GMP manufacture of the majority of recombinant therapeutic proteins have been made in CHO cells making this cell line the most well studied and approved cell line for human therapeutics. CHO cells can grow to very high densities in suspension cultures, and down stream processes for purifying products are very well developed. Of relevance, is that neither vaccinia, such as vaccinia-COP or vaccinia-WR nor its derivatives such as MVA and NYVAC will propagate in CHO cells.

Expression of viral host range genes from within the pox virus under the control of local viral promoters and pox viral RNA polymerase is known in the art.

Expression of certain viral host range genes from the genome of a mammalian cell in a timely fashion to rescue or permit viral replication and permit host cell survival has not previously been described.

SUMMARY

The present specification describes in vitro cultured mammalian cells, transformed to express a poxviral host range factor and a method for propagating viral vectors, comprising culturing such cells.

In a first aspect the present invention provides a modified mammalian cell in which the genome of the cell is modified to comprise a sequence encoding CP77 under the control of a promoter such that the modified cell line sustains propagation of a poxvirus that is less able or unable to propagate in the unmodified cell.

In a second aspect the present invention provides a process for propagating an orthopoxvirus that does not propagate in CHO cells, the process comprising propagating the poxvirus in vitro in a mammalian cell line wherein the cell line is modified to encode and express CP77 under the control of a promoter.

In various alternative embodiments the modified cells are further modified to comprise a sequence encoding D13L under the control of a promoter and/or to comprise a sequence encoding K1L under the control of a promoter Reference herein to "CP77", "K1L" and "D13L" includes functional orthologs and functional variants.

DETAILED DESCRIPTION OF PARTICULAR EMBODIMENTS

The subject invention is not limited to particular procedures or agents, specific formulations of agents and various medical methodologies, as such may vary. The terminology used herein is for the purpose of describing particular embodiments only and is not intended to be limiting. Unless defined otherwise, all technical and scientific terms used herein have the same meanings as commonly understood by one of ordinary skill in the art to which this invention belongs.

Any materials and methods similar or equivalent to those described herein can be used to practice or test the present invention. Practitioners are particularly directed to: Sambrook et al., (1989) Molecular Cloning: A Laboratory Manual, 2nd ed., Cold Spring Harbor Press, Plainsview, N.Y.; Ausubel et al. (1999) *Current Protocols in Molecular Biology* (Supplement 47), John Wiley & Sons, New York; Murphy et al. (1995) Virus Taxonomy Springer Verlag: 79-87, Mahy Brian W J and Kangro O Hillar (Eds): Virology Methods Manual 1996, Academic Press; and Davison A J and Elliott R M (Eds): Molecular Virology, A practical Approach 1993, IRL Press at Oxford University Press; Perkus et al., *Virology* (1990) 179(1):276-86 or definitions and terms of the art and other methods known to the person skilled in the art.

Although any methods and materials similar or equivalent to those described herein can be used in the practice or testing of the present invention, preferred methods and materials are described. For the purposes of the present invention, the following terms are defined below.

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. In the context of attenuated orthopox vectors, the subject vectors are modified for attenuation by comprising deletion of an essential maturation or assembly gene however, further modification such as to vector an antigen or other protein is encompassed.

By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein the singular forms "a", "an" and "the" include plural aspects unless the context clearly dictates otherwise. Thus, for example, reference to "a cell" includes a single cell, as well as two or more cells; reference to "an organism" includes one organism, as well as two or more organism; and so forth. In some embodiments, "an" means "one or more than one".

As used herein, "and/or" refers to and encompasses any and all possible combinations of one or more of the associated listed items, as well as the lack of combinations when interpreted in the alternative (or).

"Attenuation" or "attenuated" as used herein means a reduction of viral vector virulence. Virulence is defined as the ability of a virus to cause disease in a particular host. A poxviral vector that is unable to produce infectious viruses may initially infect cells but is unable substantially to replicate itself fully or propagate within the host or cause a condition. This is desirable as the vector delivers its protein or nucleic acid to the host cell cytoplasm, but does not harm the subject.

By "control element" or "control sequence" is meant nucleic acid sequences (e.g., DNA) necessary for expression of an operably linked coding sequence in a particular poxvirus, vector, plasmid or cell. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment.

Where sequences are provided, corresponding sequences are encompassed. By "corresponds to" "corresponding" or "corresponding to" is meant a nucleic acid sequence that displays substantial sequence identity to a reference nucleic acid sequence (e.g., at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence identity to all or a portion of the reference nucleic acid sequence) or an amino acid sequence that displays substantial sequence similarity or identity to a reference amino acid sequence (e.g., at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 97, 88, 89, 90, 91, 92, 93, 94, 95, 96, 97, 98, 99% or even up to 100% sequence similarity or identity to all or a portion of the reference amino acid sequence).

By "effective amount", in the context of treating or preventing a condition or for modulating an immune response to a target antigen or organism is meant the administration of an amount of an agent (e.g., an attenuated orthopox vector as described herein) or composition comprising same to an individual in need of such treatment or prophylaxis, either in a single dose or as part of a series, that is effective for the prevention of incurring a symptom, holding in check such symptoms, and/or treating existing symptoms, of that condition or for modulating the immune response to the target antigen or organism. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the terms "encode," "encoding" and the like refer to the capacity of a nucleic acid to provide for another nucleic acid or a polypeptide. For example, a nucleic acid sequence is said to "encode" a polypeptide if it can be transcribed and/or translated to produce the polypeptide or if it can be processed into a form that can be transcribed and/or translated to produce the polypeptide. Such a nucleic acid sequence may include a coding sequence or both a coding sequence and a non-coding sequence. Thus, the terms "encode," "encoding" and the like include an RNA product resulting from transcription of a DNA molecule, a protein resulting from translation of an RNA molecule, a protein resulting from transcription of a DNA molecule to form an RNA product and the subsequent translation of the RNA product, or a protein resulting from transcription of a DNA molecule to provide an RNA product, processing of the RNA product to provide a processed RNA product (e.g., mRNA) and the subsequent translation of the processed RNA product.

The term "endogenous" refers to a gene or nucleic acid sequence or segment that is normally found in a host organism.

The terms "expressible," "expressed," and variations thereof refer to the ability of a cell to transcribe a nucleotide sequence to RNA and optionally translate the mRNA to synthesize a peptide or polypeptide that provides a biological or biochemical function.

As used herein, the term "gene" includes a nucleic acid molecule capable of being used to produce mRNA optionally with the addition of elements to assist in this process. Genes may or may not be capable of being used to produce a functional protein. Genes can include both coding and non-coding regions (e.g., introns, regulatory elements, promoters, enhancers, termination sequences and 5' and 3' untranslated regions).

The terms "heterologous nucleic acid sequence," "heterologous nucleotide sequence," "heterologous polynucleotide," "foreign polynucleotide," "exogenous polynucleotide" and the like are used interchangeably to refer to any nucleic acid (e.g., a nucleotide sequence comprising an IRES) which is introduced into the genome of an organism by experimental manipulations and may include gene sequences found in that organism so long as the introduced gene contains some modification (e.g., a point mutation, deletion, substitution or addition of at least one nucleotide, the presence of a endonuclease cleavage site, the presence of a loxP site, etc.) relative to the viral genomic sequence before the modification.

The terms "heterologous polypeptide," "foreign polypeptide" and "exogenous polypeptide" are used interchangeably to refer to any peptide or polypeptide which is encoded by an "heterologous nucleic acid sequence," "heterologous nucleotide sequence," "heterologous polynucleotide," "foreign polynucleotide" and "exogenous polynucleotide," as defined above.

The term "mammalian cell" means a cell into which a vector including the attenuated orthopox vector of the invention may be introduced for the purpose of propagating the poxvirus vector. In one embodiment, the cell is a continuous cell line. It is less imperative that the modified cell is a cell line able to divide continuously. A mammalian or higher eukaryotic cell may be modified in accordance with the present invention and subsequently transformed or immortalised to become a continuously dividing cell line. However, the cell prior to modification is conveniently a well characterised and continuously dividing biotechnology compatible continuous cell line known in the art. Such cells are conveniently available from depositing organisations such as the American Type Culture Collection (ATCC) or European Collection of Cell Cultures (ECACC).

Suitable mammalian cell lines include, but are not limited to, RK18, BHK, VERO, HBOC-143B, HaCat, HepG2, HeLa, HT1080, HEK-293, RD, COS-7, CHO, Jurkat, HUT, SUPT, C8166, MOLT4/clone8, MT-2, MT-4, H9, PM1, CEM, myeloma cells (e.g., SB20 cells) and CEMX174 are available, for example, from the ATCC.

Any art recognised genome engineering method for producing modified cell lines expressing heterologous genes may be employed. Reference is made to use of transposon technology to insert genes into the cellular genome by using piggyBac vectors. However, many method are recognised for introducing gene into cells, including, without limitation, retrovirus transduction (e.g., MoMLV, etc), lentivirus transduction, plasmid transfection and integration, other viral system for transducing cell lines such as Adenovirus, AAV (Adenovirus Associated Virus), EBV and genome editing techniques for site specific insertion by homologous recombination with linear DNA, engineered meganucelases, transcription-activator like effector nucleases (TAL-nuclease), Zinc-finger-nucleases (ZFNs) and CRISPRs.

In one embodiment, the mammalian cell is a CHO cell. Prior art CHO cell lines, which do not encode viral host name genes, do not support manufacture of vaccinia or vaccinia derivatives substantially unable to propagate in man. As known to those of skill in the art, Chinese hamster ovary (CHO) cells, derived from the ovary of the hamster, *Cricetulus griseus*, are the most commonly used mammalian cell for bio-industrial and GMP production of recombinant protein therapeutics, including antibodies. The popularity of CHO cells for this purpose stems, in part, from their rapid growth and high protein production. As a result, CHO cell lines have been well characterized. Suitable CHO cell lines include without limitation A2, A2H, XrS6, CHO-K1, CHO/dhfr, RR-CHO-K1, UT-I, P22, CHO-1C6, Lec1, Lec2, Lec8, Pro-5 an CDKXB1 lines. The CHO-K1 cell line deposited with the ATCC under Accession Number ATCC CLL-61 or ATCC CRL-9618 is frequently employed. The CHO-K1 cell line was derived as a subclone from the parental CHO cell line initiated from a biopsy of an ovary of an adult Chinese hamster by Puck T. (1957). The present specification describes modified cells other than modified CHO cells.

In some embodiments, the mammalian cell is a human cell, a primate cell, a hamster cell or a rabbit cell.

Cells may be unicellular, or can be grown in tissue culture as liquid cultures, monolayers or the like. Host cells may also be derived directly or indirectly from tissues or may exist within an organism including animals.

It will be understood that "inducing" an immune response as contemplated herein includes eliciting or stimulating an immune response and/or enhancing a previously existing immune response.

As used herein, the term "internal ribosomal entry site" or "IRES" refers to a viral, cellular, or synthetic (e.g., a recombinant) nucleotide sequence which allows for initiation of translation of an mRNA at a site internal to a coding region within the same mRNA or at a site 3' of the 5' end of the mRNA, to provide for translation of an operably linked coding region located downstream of (i.e., 3' of) the internal ribosomal entry site. This makes translation independent of the 5' cap structure, and independent of the 5' end of the mRNA. An IRES sequence provides necessary cis-acting sequences required for initiation of translation of an operably linked coding region.

As used herein the term "isolated" is meant to describe a cell, a compound of interest (e.g., a recombinant poxvirus, a nucleic acid molecule such as a genome, a polypeptide, etc.) that is in an environment different from that in which the compound naturally occurs. "Isolated" is meant to include compounds that are within samples that are substantially enriched for the compound of interest and/or in which the compound of interest is partially or substantially purified.

The term "operably connected" or "operably linked" as used herein refers to a juxtaposition wherein the components so described are in a relationship permitting them to function in their intended manner. For example, a transcriptional control sequence "operably linked" to a coding sequence refers to positioning and/or orientation of the transcriptional control sequence relative to the coding sequence to permit expression of the coding sequence under conditions compatible with the transcriptional control sequence. In another example, an IRES operably connected to an orthopox virus coding sequence refers to positioning and/or orientation of the IRES relative to the orthopox virus coding sequence to permit cap-independent translation of the orthopox virus coding sequence.

As used here the terms "open reading frame" and "ORF" are used interchangeably herein to refer to the amino acid sequence encoded between translation initiation and termination codons of a coding sequence. The terms "initiation codon" (e.g., ATG) and "termination codon" (e.g., TGA, TAA, TAG) refer to a unit of three adjacent nucleotides ('codon') in a coding sequence that specifies initiation and chain termination, respectively, of protein synthesis (mRNA translation).

As used herein, the term "parent virus" will be understood to be a reference to a virus that is modified to incorporate heterologous nucleic acid sequence to form a recombinant virus of the present invention.

The terms "polynucleotide," "polynucleotide sequence," "nucleotide sequence," "nucleic acid" or "nucleic acid sequence as used herein designate mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of RNA or DNA.

"Polypeptide," "peptide," "protein" and "proteinaceous molecule" are used interchangeably herein to refer to molecules comprising or consisting of a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

As used herein the term "recombinant" as applied to "nucleic acid molecules," "polynucleotides" and the like is understood to mean artificial nucleic acid structures (i.e., non-replicating cDNA or RNA; or replicons, self-replicating cDNA or RNA) which can be transcribed and/or translated in host cells or cell-free systems described herein. Recombinant nucleic acid molecules or polynucleotides may be inserted into a vector. Non-viral vectors such as plasmid expression vectors or viral vectors may be used. The kind of vectors and the technique of insertion of the nucleic acid construct according to this invention is known to the artisan. A nucleic acid molecule or polynucleotide according to the invention does not occur in nature in the arrangement described by the present invention. In other words, an heterologous nucleotide sequence is not naturally combined with elements of a parent virus genome (e.g., promoter, ORF, polyadenylation signal, ribozyme).

As used herein, the term "recombinant virus" will be understood to be a reference to a "parent virus" comprising at least one heterologous nucleic acid sequence.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gin, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

The terms "signal sequence" or "signal peptide refers to a short (about 3 to about 60 amino acids long) peptide that directs co- or post-translational transport of a protein from the cytosol to certain organelles such as the nucleus, mitochondrial matrix, and endoplasmic reticulum, for example. For proteins having an ER targeting signal peptide, the signal peptides are typically cleaved from the precursor form by signal peptidase after the proteins are transported to the ER, and the resulting proteins move along the secretory pathway to their intracellular (e.g., the Golgi apparatus, cell membrane or cell wall) or extracellular locations. "ER targeting signal peptides," as used herein include amino-terminal hydrophobic sequences which are usually enzymatically removed following the insertion of part or all of the protein through the ER membrane into the lumen of the ER. Thus, it is known in the art that a signal precursor form of a sequence can be present as part of a precursor form of a protein, but will generally be absent from the mature form of the protein.

"Similarity" refers to the percentage number of amino acids that are identical or constitute conservative substitutions as defined in Table A below. Similarity may be determined using sequence comparison programs such as GAP (Deveraux et al. 1984, *Nucleic Acids Research* 12: 387-395). In this way, sequences of a similar or substantially different length to those cited herein might be compared by insertion of gaps into the alignment, such gaps being determined, for example, by the comparison algorithm used by GAP.

TABLE A

Exemplary Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

The terms "subject" "patient," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice, rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of treatment or prophylaxis of a condition. However, it will be understood that the aforementioned terms do not imply that symptoms are present.

The term "transgene" is used herein to describe genetic material that has been or is about to be artificially introduced into a genome of a host organism and that is transmitted to the progeny of that host. In some embodiments, it confers a desired property to a mammalian cell or an orthopox vector into which it is introduced, or otherwise leads to a desired therapeutic or diagnostic outcome.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "wild-type," "natural," "native" and the like with respect to an organism, polypeptide, or nucleic acid sequence, that the organism polypeptide, or nucleic acid sequence is naturally occurring or available in at least one naturally occurring organism which is not changed, mutated, or otherwise manipulated by man.

Variants include nucleic acid molecules sufficiently similar to a referenced molecule or their complementary forms over all or part thereof such that selective hybridisation may be achieved under conditions of medium or high stringency, or which have about 60% to 90% or 90 to 98% sequence identity to the nucleotide sequences defining a referenced poxvirus host range factor over a comparison window comprising at least about 15 nucleotides. Preferably the hybridisation region is about 12 to about 18 nucleobases or greater in length. Preferably, the percent identity between a particular nucleotide sequence and the reference sequence is at least about 80%, or 85%, or more preferably about 90% similar or greater, such as about 95%, 96%, 97%, 98%, 99% or greater. Percent identities between 80% and 100% are encompassed. The length of the nucleotide sequence is dependent upon its proposed function. Homologs are encompassed. The term "homolog" "homologous genes" or "homologs" refers broadly to functionally and structurally related molecules including those from other species. Homologs and orthologs are examples of variants.

Nucleic acid sequence identity can be determined in the following manner. The subject nucleic acid sequence is used to search a nucleic acid sequence database, such as the GenBank database (accessible at web site www.nchi.nln.nih.gov/blast/), using the program BLASTM version 2.1 (based on Altschul et al. (1997) *Nucleic Acids Research* 25:3389-3402). The program is used in the ungapped mode. Default filtering is used to remove sequence homologies due to regions of low complexity. The default parameters of BLASTM are used.

Amino acid sequence identity can be determined in the following manner. The subject polypeptide sequence is used to search a polypeptide sequence database, such as the GenBank database (accessible at web site http://www.ncbi.nln.nih.gov/blast/), using the BLASTP program. The program is used in the ungapped mode. Default filtering is used to remove sequence homologies due to regions of low complexity. The default parameters of BLASTP are utilized. Filtering for sequences of low complexity may use the SEG program.

Preferred sequences will hybridise under stringent conditions to a reference sequence or its complement. The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. With respect to nucleic acid molecules greater than about 100 bases in length, typical stringent hybridization conditions are no more than 25° C. to 30° C. (for example, 10° C.) below the melting temperature (Tm) of the native duplex (see generally, Sambrook et al., (supra); Ausubel et al., (1999)). Tm for nucleic acid molecules greater than about 100 bases can be calculated by the formula Tm=81.5+0.41% (G+C−log ($Na^+$)). With respect to nucleic acid molecules having a length less than 100 bases, exemplary stringent hybridization conditions are 5° C. to 10° C. below Tm.

The term "deletion" in the present context removal of all or part of the coding region of the target gene. The term also encompasses any form of mutation or transformation which ablates gene expression of the target gene or ablates or substantially down regulates the level or activity of the encoded protein.

Reference to "gene" includes DNA corresponding to the exons or the open reading frame of a gene. Reference herein to a "gene" is also taken to include: a classical genomic gene consisting of transcriptional and/or translational regulatory sequences and/or a coding region and/or non-translated sequences (i.e. introns, 5'- and 3'-untranslated sequences); or mRNA or cDNA corresponding to the coding regions (i.e. exons) and 5'- and 3'-untranslated sequences of the gene.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

Chimeric constructs suitable for effecting the present modified mammalian cells comprise a nucleic acid sequence encoding an orthopox host range factor, which is operably linked to a regulatory sequence. The regulatory sequence suitably comprises transcriptional and/or translational control sequences, which will be compatible for expression in the cell. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated. The promoters may be either naturally occurring promoters, or hybrid promoters that combine elements of more than one promoter.

Promoter sequences contemplated may be native to mammalian cells or may be derived from an alternative source, where the region is functional in the chosen organism. The choice of promoter will differ depending on the intended host cell. For example, promoters which could be used for expression in mammalian cells include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumor virus LTR promoter, the adenovirus major late promoter (Ad MLP), the herpes simplex virus promoter, and a HPV promoter, particularly the HPV upstream regulatory region (URR), among others. All these promoters are well described and readily available in the art.

Enhancer elements may also be used herein to increase expression levels of the mammalian constructs. Examples include the SV40 early gene enhancer, as described for example in Dijkema et al. (1985) *EMBO J.* 4:761, the enhancer/promoter derived from the long terminal repeat (LTR) of the Rous Sarcoma Virus, as described for example in Gorman et al., (1982) *Proc. Natl. Acad. Sci. USA* 79:6777 and elements derived from human CMV, as described for example in Boshart et al. (1985) *Cell* 41:521, such as elements included in the CMV intron A sequence.

The chimeric construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the chimeric construct further contains a selectable marker gene to permit selection of cells containing the construct. Selection genes are well known in the art and will be compatible for expression in the cell of interest.

In one embodiment, expression of the orthopox structural or assembly gene is under the control of a promoter. In one non-limiting embodiment the promoter is a cellular constitutive promoter, such as human EF1 alpha (human elongation factor 1 alpha gene promoter), DHFR (dihydrofolate reductase gene promoter) or PGK (phosphoglycerate kinase gene promoter) that direct expression of a sufficient level of CP77 to sustain viral propagation in the absence of significant toxic effects on the host cell. Promoters may also be inducible, such as the cellular inducible promoter, MTH (from a metallothionein gene) viral promoters are also employed in mammalian cells, such as CMV, RSV, SV-40, and MoU3.

In a first aspect the present invention provides a modified mammalian cell in which the genome of the cell is modified to comprise a sequence encoding CP77 under the control of a promoter such that the modified cell line sustains propagation of a poxvirus that is less able or unable to propagate in the unmodified cell.

In a second aspect the present invention provides a process for propagating an orthopoxvirus that does not propagate in CHO cells, the process comprising propagating the poxvirus in vitro in a mammalian cell line wherein the cell line is modified to encode and express CP77 under the control of a promoter.

In an embodiment the genome of the cell further comprises a sequence encoding D13L under the control of a promoter and/or further comprises a sequence encoding K1L under the control of a promoter.

In another embodiment the cell is a continuous cell line, preferably a CHO cell.

In other embodiments the cell may be a human cell, a primate cell, a hamster cell or a rabbit cell.

In another embodiment the CP77 gene, D13L gene and/or the K1L gene is under the control of a mammalian promoter.

In another embodiment the expression of the CP77 gene supports propagation of the virus to generate virus yields equivalent to that observed in a permissive cell line and preferably supports a virus replication amplification ratio of more than 500.

In another embodiment the CP77, D13L and/or K1L is/are encoded by a contiguous sequence of nucleotides codon optimised for expression in mammalian cells.

An example K1L sequence is provided in SEQ ID NO:6 and SEQ ID NO:7.

The specification relates broadly to modified (recombinant or transformed) cells and to a process for in vitro manufacture of virus vectors in cultured higher eukaryotic host cells, wherein the cell is genetically modified in such a way as to enhance or facilitate multiplication of the virus vector within or via a population of the cells in vitro. In one non-limiting embodiment, the specification provides for the propagation of vaccinia-based poxviruses in modified Chinese hamster ovary (CHO) cells.

As known to those of skill in the art, Chinese hamster ovary (CHO) cells, derived from the ovary of the hamster, *Cricetulus griseus*, are the most commonly used mammalian cell for bio-industrial and GMP production of recombinant protein therapeutics, including antibodies. The popularity of CHO cells for this purpose stems, in part, from their rapid growth and high protein production. As a result, CHO cell lines have been well characterized. Suitable CHO cell lines include without limitation A2, A2H, XrS6, CHO-K1, CHO/dhfr, RR-CHO-K1, UT-I, P22, CHO-1C6, Lec1, Lec2, Lec8, Pro-5 an CDKXB1 lines. The CHO-K1 cell line deposited with the ATCC under Accession Number ATCC CLL-61 or ATCC CRL-9618 is frequently employed. The CHO-K1 cell line was derived as a subclone from the parental CHO cell line initiated from a biopsy of an ovary of an adult Chinese hamster by Puck T. (1957). The present specification describes modified cells other than modified CHO cells.

To maximise the yield of virus produced, cell lines such as CHO cells may be adapted to suspension culture using standard techniques. Reference to a recombinant or modified cell includes its progeny. Cells may be sold in any form, including frozen or in liquid suspension form. Cells may be sold infected with a poxvirus vector.

Reference herein to CP77 means the cowpox host range gene referred to in Sphener et al. (1988), and Hsiao et al. (2006) and to functional orthologs and modified forms thereof able as determined herein to support pox viral growth when expressed as a heterologous gene in the genome of a mammalian host cell. Reference to "modified forms" includes a variation (such as a deletion, substitution or addition) from the wild-type or reference sequence. A reference nucleotide sequence is provided in SEQ ID NO: 1. Modified forms share at least 80% sequence identity over the coding region or one or more portions thereof comprising at least 200 contiguous basepairs. Modified forms include codon optimised forms as described herein that are optimised for expression in a mammalian or other higher eukaryotic cells including CHO cells. Reference to CP77 includes orthologs i.e., genes with the same function present in other species or identified by different names. The cowpox host range factor, CP77 is also referred to as VHR1, CHOhr, and CPXV025. The CHOhr/CP77 gene in the Western Reserve (WR) strain of vaccinia is substantially fragmented and fails to produce a functional factor. CP77 is absent in MVA and the Copenhagen strain.

Reference herein to "CP77", "D13L" and "K1L" includes functional orthologs and functional variants. "Functional" refers to the herein described quality of expression, (i.e., transcription and translation) directed from the mammalian genome of a cultured cell, to support poxvirus propagation within the expressing cell cytoplasm. The term "propagate" includes intracellular propagation and intercellular propagation and encompasses the production of mature viral particles.

In one embodiment, a population of the modified cells sustains propagation of a poxvirus that is less able or substantially unable to propagate in an unmodified control cell. The inability to propagate means that cell to cell or subject to subject transmission does not typically occur.

Reference to "unmodified control cell" includes the modified cell as it existed prior to modification to encode at least one viral host range factor selected from the group consisting of CP77, K1L and SPI-1 and to express same from its genome under control of a promoter, as well as other suitable control cells known in the art.

For example, poxviruses such as MVA and vaccinia are unable to propagate in CHO cells. However, as surprisingly determined herein, CHO cells that are recombinantly modified to express CP77 from their genome under the control of a promoter are able to support propagation of not only vaccinia but also derivatives of vaccinia such as MVA. After propagation in the subject modified CHO-CP77 cells, MVA and vaccinia are still unable to propagate in unmodified CHO cells or other suitable control.

Reference herein to "poxvirus" includes a recombinant poxvirus vector encoding a heterologous molecule of interest (such as an antigen of interest) as a medicament, prophylactic, diagnostic or therapeutic agent. Such recombinant poxvirus vectors are typically for use as vaccines against non-poxviral induced diseases or conditions. Also, the term poxvirus includes isolated poxviruses and derivatives thereof proposed for use as a therapeutic or prophylactic vaccine against a poxvirus infection, such as variola or small pox infection.

Reference herein to "vaccinia-based" includes vaccinia and derivatives and modified forms of vaccinia virus. Vaccinia based derivatives include, but are in no way limited to, MVA and NYVAC. Reference to MVA and NYVAC includes strains or derivates of these poxviruses known in the art. Modified forms may have modifications in one to ten or more genes. The term "modification" is intended to mean a variation (such as a deletion, substitution or addition) from the wild-type or reference sequence. Reference to "attenuated" includes poxvirus that do not propagate or which propagate to a substantially lesser degree in a relevant subject compared to a non-attenuated form of the same virus. The term also includes viruses that are non-pathogenic in a subject.

In one embodiment, the cell is a continuous cell line. It is less imperative that the modified cell is a cell line able to divide continuously. A mammalian or higher eukaryotic cell may be modified in accordance with the present invention and subsequently transformed or immortalised to become a continuously dividing cell line. However, the cell prior to modification is conveniently a well characterised and continuously dividing biotechnology compatible continuous cell line known in the art. Such cells are conveniently available from depositing organisations such as the American Type Culture Collection (ATCC) or European Collection of Cell Cultures (ECACC).

Suitable mammalian cell lines include, but are not limited to, RK18, BHK, VERO, HBOC-143B, HaCat, HepG2, HeLa, HT1080, HEK-293, RD, COS-7, CHO, Jurkat, HUT, SUPT, C8166, MOLT4/clone8, MT-2, MT-4, H9, PM1, CEM, myeloma cells (e.g., SB20 cells) and CEMX174 are available, for example, from the ATCC.

In one embodiment, the cell is a CHO cell. Prior art CHO cell lines, which do not encode viral host name genes, do not support manufacture of vaccinia or vaccinia derivatives substantially unable to replicate in man.

In some embodiments, the cell is a human cell, a primate cell, a hamster cell or a rabbit cell.

Chimeric constructs suitable for effecting the present modified mammalian cells comprise a nucleic acid sequence encoding a poxviral host range factor, which is operably linked to a regulatory sequence. The regulatory sequence suitably comprises transcriptional and/or translational control sequences, which will be compatible for expression in the cell. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated. The promoters may be either naturally occurring promoters, or hybrid promoters that combine elements of more than one promoter.

Promoter sequences contemplated may be native to mammalian cells or may be derived from an alternative source, where the region is functional in the chosen organism. The choice of promoter will differ depending on the intended host cell. For example, promoters which could be used for expression in mammalian cells include the metallothionein promoter, which can be induced in response to heavy metals such as cadmium, the β-actin promoter as well as viral promoters such as the SV40 large T antigen promoter, human cytomegalovirus (CMV) immediate early (IE) promoter, Rous sarcoma virus LTR promoter, the mouse mammary tumor virus LTR promoter, the adenovirus major late promoter (Ad MLP), the herpes simplex virus promoter, and a HPV promoter, particularly the HPV upstream regulatory region (URR), among others. All these promoters are well described and readily available in the art.

Enhancer elements may also be used herein to increase expression levels of the mammalian constructs. Examples include the SV40 early gene enhancer, as described for example in Dijkema et al. (1985) *EMBO J.* 4:761, the enhancer/promoter derived from the long terminal repeat (LTR) of the Rous Sarcoma Virus, as described for example in Gorman et al., (1982) *Proc. Natl. Acad. Sci. USA* 79:6777 and elements derived from human CMV, as described for example in Boshart et al. (1985) *Cell* 41:521, such as elements included in the CMV intron A sequence.

The chimeric construct may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nts and may contain transcriptional and translational termination sequences in addition to a polyadenylation signal and any other regulatory signals capable of effecting mRNA processing or gene expression.

In some embodiments, the chimeric construct further contains a selectable marker gene to permit selection of cells containing the construct. Selection genes are well known in the art and will be compatible for expression in the cell of interest.

In one embodiment, expression of the viral host range gene is under the control of a promoter. In one non-limiting embodiment the promoter is a cellular constitutive promoter, such as human EF1 alpha (human elongation factor 1 alpha gene promoter), DHFR (dihydofolate reductase gene promoter) or PGK (phosphoglycerate kinase gene promoter) that direct expression of a sufficient level of CP77 to sustain viral propagation in the absence of significant toxic effects on the host cell. Promoters may also be inducible, such as the cellular inducible promoter, MTH (from a metallothionein gene) viral promoters are also employed in mammalian cells, such as CMV, RSV, SV4, and MoU3.

Conveniently, in one embodiment, the expression of the viral host range gene supports propagation of the virus to generate virus yields equivalent to that observed in permissive cell lines. The expression of the viral host range gene, for example, supports a virus replication amplification ratio of more than 500. The expression of the viral host range gene supports viral propagation in the absence of significant host cell toxicity. Significant host cell toxicity refers to a level of viral host range factor expression that reduces viral yield due to premature host cell death or failure to divide. The skilled artisan is familiar with methods for qualitatively or quantitatively assessing host cell parameters such as host cell survival and multiplication, and viral parameters, such as viral host range gene expression, viral replication and viral yield.

In one embodiment, the poxvirus is a chordopox virus, other than an orthopox virus that encodes a functional CP77 or CP77 ortholog. Cowpox virus encodes CP77 and is therefore not encompassed in this aspect. Orthopox viruses include, buffalopox virus, cowpox virus, camelpox virus, ectromelia virus, monkeypox virus, rabbitpox virus, racconpox virus, teterapox virus, vaccinia virus, volepox virus, skunkpox virus, and Uasin Gishu disease virus of horses. Other genus include the parapoxviruses, avipoxviruses, capripoxviruses, leporipoxviruses, swinepoxviruses, molluscipoxviruses and yatapoxviruses.

In one embodiment, the poxvirus is MVA or a derivative of MVA that is substantially unable to replicate in man/a subject.

In one embodiment, the poxvirus is vaccinia or an derivative of vaccinia that is substantially non-replicative in vivo in man.

In another embodiment, the poxvirus is suitable for use as a poxviral vaccine.

In one further embodiment, the poxvirus is a recombinant poxviral vector which encodes and expresses a heterologous molecule of interest, such as an antigen of medical interest, wherein the recombinant poxviral vector is for use as a diagnostic, therapeutic or prophylactic agent in a subject.

Reference herein to K1L means the gene described by Shisler and Jin (2004) and orthologs or modified forms thereof.

Reference herein to SPI-1 means the host range gene described by Brookes et al. (1995) or orthologs and modified forms thereof.

In some embodiments, and for the avoidance of doubt, the instant enhanced viral propagative process does not require addition of genes to the poxviral genome. This does not, of course, exclude modifications of viral vectors for other purposes, such as, without limitation, to encode heterologous molecules as antigens of interest for vaccine purposes or to engender an immune response in a subject.

Transcription of the poxviral host range gene from within the host cell nucleus and translation of the encoded product takes place in the infected cell and is sufficient for pox viral propagation in the host cell cytoplasm. Without limitation to any particular mode of action, it is proposed that CP77 is a viral protection agent.

In one illustrative embodiment, the poxviral host range gene expressed by the infected cell line is CP77. As shown in Example 4, when a CHO cell nucleus is modified to encode and express CP77 it is able to sustain viral amplification as if it were a permissive cell line such as 143B. Typically, confluent plaques are observed within two days from infection.

In another embodiment, the level of viral propagation in the modified cell provides an amplification ratio of at least 10 to 5000. Amplification ratios are, in some embodiments, between 500 and 3000, or between 1000 and 4000.

In another embodiment, the promoter driving expression of the heterologous pox viral host range gene provides a level of pox viral host range heterologous gene expression in the cell. The level of CP77 expression can be similar to or exceed that produced by cowpox virus in permissive cells.

In another embodiment, the promoter driving expression of the heterologous pox viral host range gene provides a level of heterologous gene expression in the cell sufficient to allow viral propagation at least to the level of viral propagation in a permissive cell.

In one embodiment, poxviral production in a CHO cell line is equal to or exceeds the level of poxviral production in a positive control cell.

In one embodiment, the level of MVA viral production in CHO cells is substantially equal to or exceeds the level of MVA viral production in CEF cells.

In one embodiment, CP77, K1L and/or SPI-1 is/are encoded by a contiguous sequence of nucleotides that is codon optimised for expression in mammalian cells.

As described further herein, the codon optimised nucleic acid sequence encoding CP77 may have less than 80% or less than 75% nucleotide sequence identity to the sequence encoding the cowpox CP77 protein of the Brighton Red strain (UniprotKB/Swiss-Prot:P12932.1). In some embodiments the codon optimised sequence has the sequence set forth in SEQ ID NO: 1 or is a functional variant comprising a nucleic acid sequence that has at least 70% sequence identity to the sequence set forth in SEQ ID NO: 1. In some embodiments, the CP77 virus host range factor has an amino acid sequence set forth in SEQ ID NO: 2 or has at least 70% amino acid sequence identity to the amino acid sequence set forth in SEQ ID NO:2.

In some embodiments, a kit is contemplated comprising or consisting essentially of a population, such as a clonal population, of modified mammalian cells expressing CP77 from their genome as described herein. In some embodiments, the modified cell does not contain a vaccinia virus.

The present description further describes a process for or method of manufacturing a poxvirus that does not propagate in CHO cells, the process comprising propagating the poxvirus in vitro in a mammalian cell line wherein the cell line is modified to encode and express CP77 under the control of a promoter. The process may further comprise isolating viral particles.

The cell line is conveniently a mammalian cell line known to those of skill in the art to be suitable for the manufacture of a medicament or therapeutic, diagnostic or prophylactic agent.

The specification describes a modified CHO cell, wherein the CHO cell is modified to encode CP77 and express same from its genome under control of a promoter.

In one embodiment, the modified CHO cell line sustains propagation of a virus that is less able or unable to propagate in an unmodified control CHO cell which is one that does not express CP77.

In one embodiment, the virus is an orthopox virus other than an orthopox virus that encodes CP77. As known in the art, cowpox virus is a pox virus that encodes CP77.

In some embodiments, the virus is vaccinia or a derivative of vaccinia that is substantially non-replicative in vivo in man/a subject.

In some embodiments, the virus is MVA.

In another embodiment, the specification provides a method of propagating a poxvirus which is substantially non-replicative in man, the method comprising: (i) culturing a CHO cell which has been transformed to express CP77; and (ii) infecting the cultured CHO cell from (i) with the poxvirus which is substantially non-replicative in man.

In another embodiment, the specification provides a method of propagating a poxvirus which is substantially non-replicative in man, the method comprising: (i) culturing a CHO cell which has been transformed to express CP77 and D13L and/or K1L, and (ii) infecting the cultured CHO cell from (i) with the poxvirus which is substantially non-replicative in man.

In another embodiment, the specification provides a method of propagating MVA, the method comprising: (i) culturing a CHO cell which has been transformed to express CP77 and D13L and/or K1L and (ii) infecting the cultured CHO cell from (i) with MVA.

In another embodiment, the specification provides a method of propagating, a vaccinia derivative which is substantially non-replicative in man, the method comprising: (i) culturing a CHO cell which has been transformed to express CP77 and D13L and/or K1L and (ii) infecting the cultured CHO cell from (i) with the vaccinia derivative.

In another embodiment, the specification provides a method of propagating MVA encoding a heterologous protein, the method comprising: (i) culturing a CHO cell which has been transformed to express CP77 and D13L and/or K1L and (ii) infecting the cultured CHO cell from (i) with the MVA.

In another embodiment, the specification provides a method of propagating, a vaccinia derivative encoding a heterologous protein, which is substantially non-replicative in man, the method comprising: (1) culturing a CHO cell which has been transformed to express CP77 and D13L and/or K1L and (ii) infecting the cultured CHO cell from (i) with the vaccinia derivative.

In another embodiment, the present specification provides an artificially created vector, polynucleotide or plasmid comprising the nucleic acid sequence of a virus host range gene operably connected to regulatory elements such as a promoter for expression in a mammalian cell line. In some embodiments, the virus gene is cowpox ankyrin repeat domain-containing protein CP77 gene (UniProtKBSwiss-Prot P12932.1 [025LBR CP77 protein]. In one embodiment the virus host range gene, such as CP77, is codon optimised for expression in a mammalian cell line. Suitable vectors and plasmids are known in the art.

In one embodiment, the polynucleotide encodes CP77. In some embodiments, the polynucleotide comprises the nucleotide sequence set forth in SEQ ID NO: 1 (codon optimised for expression in mammalian cells such as CHO). In some embodiments, the isolated polynucleotide comprises the nucleotide sequence set forth in SEQ ID NO:1 or a variant thereof that encodes the amino acid sequence set out in SEQ ID NO: 2.

In another embodiment, the present specification described a transposition delivery vector for stable insertion of a virus host range gene into a mammalian cell.

The present description also provides a method of transforming a mammalian or higher eukaryotic culture cell which is substantially non-permissive to a virus, into a cell which is permissive to the virus, the method comprising transforming the cell to express CP77.

In some embodiments, the method includes transfecting the cell with a vector capable of directing expression of an encoded CP77 under the control of a mammalian promoter.

In some embodiments the vector is a transposition delivery vector encoding CP77 under the control of a mammalian promoter.

In one non-limiting embodiment the promoter is a cellular constitutive promoter, such as human EF1 alpha (human elongation factor 1 alpha gene promoter), DHFR (dihydofolate reductase gene promoter) or PGK (phosphoglycerate kinase gene promoter) that direct expression of a sufficient level of CP77 to sustain viral propagation in the absence of significant toxic effects on the host cell. Promoters may also be inducible, such as the cellular inducible promoter, MTH (from a metallothionein gene) viral promoters are also employed in mammalian cells, such as CMV, RSV, SV4, and MoU3.

In some embodiments, the cell is a CHO cell.

In some embodiments the virus is a poxvirus.

In some embodiments the poxvirus is a vaccinia derivative which is non-pathogenic or non-replicating in man.

By "isolated" is meant material that is substantially or essentially free from components that normally accompany it in its native state. For example an "isolated polynucleotide" or an "isolated polypeptide" and the like, as used herein, refer to in vitro isolation and/or purification of a polynucleotide or polypeptide molecule from its natural cellular environment, and from association with other components of the cell. Without limitation, an isolated composition, complex, polynucleotide, peptide, or polypeptide can refer to a native sequence that is isolated by purification or to a sequence that is produced by recombinant or synthetic means.

Variants include nucleic acid molecules sufficiently similar to a referenced molecule or their complementary forms over all or part thereof such that selective hybridisation may be achieved under conditions of medium or high stringency, or which have about 60% to 90% or 90 to 98% sequence identity to the nucleotide sequences defining a referenced poxvirus host range factor over a comparison window comprising at least about 15 nucleotides. Preferably the hybridisation region is about 12 to about 18 nucleobases or greater in length. Preferably, the percent identity between a particular nucleotide sequence and the reference sequence is at least about 80%, or 85%, or more preferably about 90% similar or greater, such as about 95%, 96%, 97%, 98%, 99% or greater. Percent identities between 80% and 100% are encompassed. The length of the nucleotide sequence is dependent upon its proposed function. Homologs are encompassed. The term "homolog" "homologous genes" or "homologs" refers broadly to functionally and structurally related molecules including those from other species. Homologs and orthologs are examples of variants.

Nucleic acid sequence identity can be determined in the following manner. The subject nucleic acid sequence is used to search a nucleic acid sequence database, such as the GenBank database (accessible at web site http://www.ncbi.nln.nih.gov/blast/), using the program BLASTM version 2.1 (based on Altschul et al. (1997) *Nucleic Acids Research* 25:3389-3402). The program is used in the ungapped mode. Default filtering is used to remove sequence homologies due to regions of low complexity. The default parameters of BLASTM are used.

Amino acid sequence identity can be determined in the following manner. The subject polypeptide sequence is used to search a polypeptide sequence database, such as the GenBank database (accessible at web site http://www.ncbi.nln.nih.gov/blast/), using the BLASTP program. The program is used in the ungapped mode. Default filtering is used to remove sequence homologies due to regions of low complexity. The default parameters of BLASTP are utilized. Filtering for sequences of low complexity may use the SEG program.

The term "hybridize under stringent conditions", and grammatical equivalents thereof, refers to the ability of a nucleic acid molecule to hybridize to a target nucleic acid molecule (such as a target nucleic acid molecule immobilized on a DNA or RNA blot, such as a Southern blot or Northern blot) under defined conditions of temperature and salt concentration. With respect to nucleic acid molecules greater than about 100 bases in length, typical stringent hybridization conditions are no more than 25° C. to 30° C. (for example, 10° C.) below the melting temperature (Tm) of the native duplex (see generally, Sambrook et al., (supra); Ausubel et al., (1999)). Tm for nucleic acid molecules greater than about 100 bases can be calculated by the formula $Tm=81.5+0.41\%\ (G+C-\log(Na^{+}))$. With respect to nucleic acid molecules having a length less than 100 bases, exemplary stringent hybridization conditions are 5° C. to 10° C. below Tm.

By "vector" is meant a polynucleotide molecule, suitably a DNA molecule derived, for example, from a plasmid, bacteriophage, yeast, virus, mammal, avian, reptile or fish into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can also include a selection marker such as an antibiotic resistance gene that can be used for selection of suitable transformants. Examples of such resistance genes are known to those of skill in the art.

Reference to "gene" includes cDNA corresponding to the exons of a gene. Reference herein to a "gene" is also taken to include: a classical genomic gene consisting of transcriptional and/or translational regulatory sequences and/or a coding region and/or non-translated sequences (i.e. introns, 5'- and 3'-untranslated sequences); or mRNA or cDNA corresponding to the coding regions (i.e. exons) and 5'- and 3'-untranslated sequences of the gene.

By "regulatory element" or "regulatory sequence" is meant nucleic acid sequences (e.g., DNA) necessary for expression of an operably linked coding sequence in a particular host cell. The regulatory sequences that are suitable for prokaryotic cells for example, include a promoter, and optionally a cis-acting sequence such as an operator sequence and a ribosome binding site. Control sequences that are suitable for eukaryotic cells include promoters, polyadenylation signals, transcriptional enhancers, translational enhancers, leader or trailing sequences that modulate mRNA stability, as well as targeting sequences that target a product encoded by a transcribed polynucleotide to an intracellular compartment within a cell or to the extracellular environment.

Complementary sequences and parts of these sequences are encompassed. The term "complement" and "complementary" when used in connection with a nucleic acid molecule refers to the complementary nucleic acid sequence as determined by Watson-Crick base pairing. For example, the complement of the nucleic acid sequence 5'CCATG3' is 5'CATGG3'.

The phrase "hybridizing specifically to" and the like refer to the binding, duplexing, or hybridizing of a molecule only to a particular nucleotide sequence under stringent conditions when that sequence is present in a complex mixture (e.g., total cellular) DNA or RNA.

The terms "subject" or "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a primate such as a human in need of treatment or prophylaxis. However, it will be understood that the aforementioned terms do not imply that symptoms are present.

The various embodiments enabled herein are further described by the following non-limiting examples.

Example 1

VACV-COP Fails to Grow in CHO Cells

Materials and Reagents

VACV-COP, VSS02, SEM120213, Titre: 1.6×10(8) pfu/mL

Vero: WHO-VERO-MCB passage No 141, Aug. 8, 2005, Virax Holdings Limited

CHO: SA-Pathology Jul. 5, 2004

Growth medium: RPMI, 10% FBS, Pen/Strep

Maintenance medium: RPMI, 2% FBS, Pen/Strep

CHO and Vero cells were cultured to confluency in one 6-Well plate (6-WP) per cell line. Each well was infected with 4×10(4) pfu of VACV-COP VSSO2 for 45 minute at room temperature and then incubated at 37° C./5% CO2 thereafter. From each cell line, the contents of 2 wells where harvested and pooled at 24 h, 48 h, 72 h post infection. Viral extracts were made by freeze thawing three times and storing at −80° C. until ready for titrations. Each extract was titred using Vero cells as described in the Protocol described in Example 4.

After freeze-thawing a homogenation probe may be used to break up these large insoluble clumps. Each well to be harvested contains 2 mL of MM. For each time point, 2 wells were pooled to give a total volume of 4 mL per time point. TE buffer may be added to give a total volume of 6 mL per time point.

The titration results, viral yield results and production yields are tabulated in Table 1. The results show that VACV-COP is unable to propagate from a low moi in CHO cells, unlike Vero cells where viral production increases with time. VACP-COP is non-permissive in CHO cells.

Example 2

Multiple-Step Growth for VACV+PH22 [CP77] in CHO Verses Vero-CP77 is Active in VACV The propagation potential in CHO of a recombinant VACV-COP expressing the cow pox virus BRO25L gene encoding CP77 (VACV-PH22 [CP77]) was determined in comparison to Vero cells in a multistep growth study.

VACV-PH22 is a recombinant vaccinia virus Copenhagen strain expressing the native 025L ORF from the Brighton strain of cowpox virus that codes for the CHO host range protein, CP77. This ORF in vaccinia is also under the control of the BRO25L native promoter. The native BRO25L gene (native promoter and ORF) was cloned to create pPH22 which also codes for a red fluorescent protein, DsRed-Express2. pPH22 is an integration vector that will insert the BRO25L gene and the DsRed gene into the B19R ORF of VACV-COP, which codes for the soluble and cell surface IFN alpha/beta receptor protein. Insertion of the BRO25L and DsRed into VACV-COP was achieved by homologous recombination as a result of infecting CHO with a low multiplicity of VACV-COP and transfection with pPH22. Only virus containing the BRO25L gene will be amplified further in CHO cells which can be visually verified by the presence of red fluorescent infected cells or plaques.

Virus extracted 3 days after homologous recombination was amplified three times in CHO and then titred in Vero cells before using in this multistep growth study in CHO cells.

Materials and Reagents

VACV-COP, VSS02, SEM120213, Titre: 1.6×108 pfu/mL

VACV-PH22 [CP77], Titre: 8×106 pfu/mL

Vero: WHO-VERO-MCB passage No 141, Aug. 8, 2005

CHO: SA-Pathology Jul. 5, 2004

Growth medium: RPMI, 10% FBS, Pen/Strep for CHO and Vero

Maintenance medium: RPMI, 2% FBS, Pen/Strep for CHO and Vero

CHO and Vero cells were cultured to confluency in 2× T25 flasks per cell line. 1 flask of each cell line was infected with $1\times10^5$ pfu of VACV-COP VSS02 and one each with $1\times10^5$ pfu of VACV-PH22 for 45 minutes at room temperature and then incubated at 37° C./5% CO2 thereafter. From each cell line, the contents of each flask where harvested 96 h post infection. Viral extracts were made by freeze thawing three times and storing at −80° C. until ready for titrations. Each extract was titred using Vero cells as described in the protocol detailed in Example 4 in 24 well plate formats.

Infections were done in T25 flask, 2 flask per cell line where flask 1 was infection with VACV-COP and flask 2 infection with VACV-PH22. Harvesting was only performed at 96 h post infection. The results are tabulated in Table 2. From Table 2 it can be seen that: CHO cells cannot support VACV-COP viral progeny production. This confirms the results described in Example 1. Further, VACV-COP was viable as infection of a permissive cell line, Vero cells in this study, amplified the inoculum level to over 200 fold, therefore the results seen in CHO where due to host cell restriction. However, when the CP77 was expressed by a recombinant vaccinia virus, VACV-PH22, amplification of the inoculum was achieved by about 700 fold. Expression of the CP77 did not limit vaccinia host range to only CHO cells, as infection of vero cells with VACV-PH22 also amplified the inoculum. However, the level of amplification may not be as good as vaccinia without CP77. Since the standard error of the titration results are so large the difference in yield may not be significant.

These results show that CP77 expressed from the viral genome is more than adequate at enabling VACV-COP to amplify in the non-permissive CHO cell line by producing yields similar to that expected from a permissive cell substrate such as Vero.

A possible function for the CP77 protein during vaccinia virus infection of CHO cells has been reported by Hsiao et al. (2006). They propose that CP77 binds to and removes the HMG20A from the newly synthesized vaccinia genome located in the viral factories, thus enabling the vaccinia life cycle to continue in CHO cells. It is postulated herein that CP77 enables the newly synthesized genome to be available for packaging which otherwise would not be available in CHO cells due to HMG20a binding to and "locking up" the genome. Since the function of CP77 is not required for viral amplification in permissive cell lines, such as Vero, it is proposed herein that there is an alternative equivalent protein, even a cellular protein, that has this function which maybe be inactive or absent in at least CHO cells but active or present in permissive cell lines. The alternative protein could render CP77 not required and thus over the evolution of vaccinia it was subsequently deleted or rearranged, as its loss of function was not essential for the broad host range.

Example 3

Construction of p-LL07-CHO (Polyclonal Cell Line Expressing CP77)

A CHO cell line was constructed to express the CP77 protein. A VACV-COP recombinant virus expressing a green fluorescent protein (EGFP) forms plaques which develop into a confluent infection within a few days of infection.

Vaccinia-COP (SCV401C) is a recombinant vaccinia virus of the Copenhagen strain (VACV-COP) that has inserted into the A39R ORF an expression cassette consisting of a strong vaccinia virus early/late promoter operatively linked to the protein coding sequence of Enhanced Green Fluorescent Protein (EGFP) and terminated by the poxvirus early transcriptional stop sequence. Upon infection of non-permissive and permissive cells, EGFP will be expressed within the infected cells which can be visualised using a fluorescent microscope. In permissive cells, the green fluorescence can be seen to spread from cell to cell as the virus spread throughout the population of cell.

The CP77 protein coding sequence was synthetically made by GeneArt GmbH (Germany) by recreating (back translation or reverse translation) the DNA sequence from the amino acid of the CP77 encoded by the 025L ORF of the cow poxvirus Brighton Red strain UniProtKB/Swiss-Prot: P12932.1, and codon optimised for expression in mammalian cell (CHO) cells. See SEQ ID NO: 1 for the codon optimised nucleotide sequence for the expression of the protein coding sequence of CP77.

The codon optimized CP77 protein coding sequence from pPH51 (a cloning plasmid harbouring the codon optimized CP77 protein coding sequence) was PCR amplified using PCR primers where the 5' primer was designed to add a kozak sequence around the start codon and the 3' primer was designed to add the flag-Tag sequence prior to the stop codon. The amplified PCR product was subcloned into the transposon piggybac vector pJ507-2 (Hyg+) purchased from DNA2.0 Inc (USA) via the Bsa I cloning site. Cloning into the BsaI effectively replaces the comet GPF coding sequence with the CP77 protein coding sequence to create pLL07. The CP77 now becomes under control of the human constitutive Elongation Factor 1 alpha promoter (EF1a) and is co-expressed with the hygromycin resistance gene once both have been stably integrated into the genome of transfected cells.

Transduction of CHO by transposon aided stable insertion of the CP77 and hygromycin resistance expression cassettes: CHO cells were seeded into wells of a 6 well plates so that after an overnight incubation they were around 50% confluency. Using the Effectene transfection reagent from Qiagen, 1 ug of pLL07 was transfected into 1 well of 50% confluent CHO cells following the manufacturer's instructions. The transfected cells were then incubated overnight in growth medium. The next day, the medium was changed with growth medium containing 500 ug/mL hygromycin B for selecting transduced cells. The selection medium was change every 2-3 days and when the transduced cells start to grow in numbers they were recovered using TrypLE Select (Life Technologies) and seeded into a T25 flask for further cell expansion.

Verification of CP77 Expression by Western Blotting (Flag Tagged)

Raising rabbit anti-CP77 sera: Rabbits were injected with a 15 amino acid peptide linked to KHL protein that represented a short internal amino acid sequence of the CP77 protein. This amino acid sequence was: SGSD-VNIRSNNGYTC-amino acid positions 481 to 495 of UniProtKBSwiss-Prot P12932.1 [025LBR CP77 protein] SEQ ID NO: 2.

A total of three injections, 1 month apart, were carried out to raise antibodies to this KHL conjugated amino acid sequence. Blood from the injected rabbit were tested by western blot against bacterial expressed and Ni-NTA purified N-terminal His-tagged CP77 protein. The rabbit anti-CP77 serum was shown to clearly recognise recombinant CP77 protein.

Testing for CP77 expression by p-LL07-CHO: Two T25 flasks were seeded with CHO and p-LL07-CHO and cultured until the cell monolayers in each flask reached 100% confluency. Cells from each flask were harvested, washed with PBS and then resuspended in 200 uL. To this, 50 μl of 5×SDS-PAGE loading buffer to each tube of resuspended cells and then incubated at 98° C. for 5 min. 15 uL of each cell protein extract was loaded into two 10% SDS-PAGE gels, electrophoresed and then blotted onto Hybond ECL nitrocellulose by electro-blotting.

The electro-blotted membranes were then treated with 5% skimmed milk powder dissolved in Tris Buffer Saline containing Tween 20 (TBST) for 1 hour at room temperature to block all available non-specific antibody binding sites on the membrane. The membranes were then washed several times in TBST before probing with antibodies. Membrane 1 was probed with 1:5000 dilution of anti-DDDDK tag antibody [M2] conjugated in HRP (ab49763, Sapphire Bioscience) overnight at 4° C. Membrane 2 was probed with 1:100 dilution of anti-CP77 antisera overnight at 4° C., washed 3 times with TBST, and then probed with secondary antibody, 1:5000 dilution of HRP conjugated anti-rabbit antibody (GE Healthcare) for 2 hours. Both membranes were then washed 3 times in TBST and treated with ECL western blotting detection reagents (GE Healthcare) and exposed to X-ray film as instructed by the user manual.

Plaque assay in CHO and p-LL7-CHO: CHO and p-LL7-CHO cells were seeded into multiple 6 well plates and were cultured until the cell monolayers were 100% confluent.

A recombinant Vaccinia virus (Copenhagen strain) harbouring an EGFP expression cassette (green fluorescent protein) under the control of an early/late vaccinia virus promoter (SCV401C) was used to infect the cells. Due to the unknown titre of SCV401C, 10 μl of the stock virus was firstly diluted in 1 ml of MM medium (Dil 1:1:100 dilution), and then infected each well with 500 μl of the viral diluent. Day 1 post infection, high moi infection was noticed where most cells were fluorescing green. It was decided to perform a further 1:20 dilution of Dil 1, by adding 100 μl Dil 1 into 2 ml of MM medium (Dil 2). Then this was used to infect each well with 500 μl of Dil 2.

The viral infections were viewed under the fluorescent microscope (Olympus IX51) with GFP filter (Cat #U-MG-FPHQ, Olympus). The image was captured using celiSens Digital Imaging Software (Olympus).

It was seen from the results that VACV-COP expressing green fluorescent protein (SCV401C) does not propagate in CHO cells as expected. The single cells fluorescing green are the result of virus entering the cell, expressing its gene including EGFP but unable to produce new infectious viral particles and therefore unable to spread the infection to the neighbouring cells. However, in a CHO cell line expressing CP77, the vaccinia virus is able to produce new infectious viruses that spreading to the neighbouring cells for form a foci of infection by day 1 post infection. These foci of infection became a confluent infection by the next two days post infection where by day 3 the entire cell monolayer was infected with SCV401C. CHO cells expressing the host range protein, CP77, are permissive to vaccinia virus infections unlike the parental (native) CHO cells.

HMG20A belongs to a family of proteins containing the HMG box domain. HMG proteins are chromosome remodeling proteins that recognize distorted DNA structures, such as cruciforms. They can also induce DNA bending by binding to the minor groove in DNA. HMG box-containing proteins are therefore considered important in chromosome remodeling during DNA replication, recombination, or repair. In addition, certain HMG box-containing proteins can affect gene transcription by interacting with transcription factors at the promoter site.

Work published by Hsiao et al. 2006 had shown that CP77 binds HMG20A in CHO-K1 cells. This host cell protein, HMG20A, seems to bind the viral DNA in the viral factories of vaccinia infected CHO cells and it was postulated that this host cell protein "locks up" the DNA in viral factories and prevents then next stage of the vaccinia life cycle and thus preventing the production of progeny infectious virus. Expression of CP77 by the cowpox virus seems to remove host HMG20A off the viral DNA and allow the viral life cycle to recommence with the eventual production of progeny infectious virus particles.

However, with the expression of CP77 in CHO in the absence of a viral infection, one would expect this protein to sequester the newly synthesized HMG20A present in the cytoplasm before it translocate to the nucleus. If this was the case, the function of the HMG20A in the nucleus would be lost, and as it plays a critical role during DNA replication, recombination and repair plus its function during gene transcription, one would expect expression of CP77 would harm the integrity of the CHO cell during cell multiplication and maintenance. This unexpectedly does not seem to be the case as the CHO cell line expressing CP77 was readily maintained as a continuous culture with no noticeable effects on its ability to replicate over many generation compared to the parental CHO cell line.

Example 4

Multistep Growth Studies

Multistep growth kinetic study was conducted in p-LL07-CHO: The permissive nature of a CHO cell line expressing the host range gene CP77 to vaccinia virus infection was assessed and the level of viral production to the production levels attained in a naturally permissive human cell line—143B was compared.

The aim was to compare the propagation characteristic of VACV-COP in p-LL07-CHO, CHO and 143B cell lines. In this study, the functionality of the expressed CP77 by p-LL07-CHO was tested by examining the amplification characteristic of VACV-COP within this cell line compared to its amplification characteristic in CHO (non-permissive) and 143B (permissive) cells.

Materials and Methods

Cell Line Setup

CHO setup: One 6-Well Plate (6WP) was seeded with CHO cells and was cultured until confluent in growth medium (RPMI+10% FBS).

143B setup: One 6-Well Plate (6WP) was seeded with 143B cells and was cultured until confluent in growth medium (RPMI+10% FBS).

p-LL07-CHO setup: 6-Well Plate (6WP) was seeded with p-LL07-CHO cells and was cultured until confluent in growth medium (RPMI+10% FBS+500 ug/ml HygromycinB).

Dilution of VACV-COP: Each well of each 6WP was infected with 0.01 pfu in a total volume of 500 uL. It was assumed the cell count per well at 100% confluency was $4\times10^6$cells. For an infection rate of 0.01 pfu/well, $4\times10^4$ pfu per well was required and so the stock virus was diluted to $8\times10^4$ pfu/mL in maintenance medium (RPMI/2% FBS).

Infections: Culture medium was removed from each well of each plate where 500 μL of diluted virus was added and left to incubate at room temperature for 1 hr for cell to adsorb the virus. Virus inoculum was then removed and each infected well was washed once with 1 mL sterile PBS and then incubated in 2 mL of MM per well at 37° C./5% $CO_2$.

Harvesting: Two sets of wells from each plate where harvested at the following times post infection: 24 h, 48 h, and 72 h. On the day of harvesting, cells were scraped into the culture medium where two set of wells from each cell line was combined and the cells pelleted by centrifugation at 1000 g for 5 min. Each cell pellet was resuspended in 1 mL of 10 mM TrisHCl pH8. The resuspended cell pellet was then subjected to three cycles of freeze-thawing and stored at −80° C. until ready for titration.

Titrations were done in Vero and 143B cells cultured to 100% confluency in 24-well plates.

Dilution: The viral extracts were removed from the freezer, thawed and sonicated to homogenise any visible clumps. The viral extracts were serial diluted to $10^{-8}$ in maintenance medium.

Infections: Growth medium was removed from each well and infected with 1 mL of each dilution (4 wells per dilution, one plate for each virus starting from $10^{-2}$ dilution) for 1 h at room temperature. After the incubation, each plate was move to the incubator and incubated at 37° C./5% CO2 for 3 days for plaques to develop.

Calculation of Titre: the dilution that contains 20 to 50 plaques, the plaques were counted and then averaged. This average count was multiplied by the reciprocal of the dilution and because 1 mL infection were used, the resulting figure will be the titre in pfu/mL.

Calculation of standard Error: Standard error (SE) at 95% confidence was calculated from the 4 titration values that constituted the mean using the following formula: 1.95×(SD/√n) where: SD is the standard deviation from a small sample, n is the number of titration replicates (4 in this case).

Calculation of yield: This is the total amount of virus within the viral extract that was being titred: Mean Titration (pfu/mL)×Total volume of Viral Extract=pfu.

Calculation of Amplification Ratio: This figure represents the fold amplification over the amount used as inoculum: Yield in pfu/Inoculum size in pfu.

Multistep growth kinetic studies were carried out in 6 well plates—two wells per cell line per time point. Each well was infected with $4\times10^4$ pfu of VACV-COP and for harvesting the 2 well for each cell line and time point was harvested and combined from which a viral extract was prepared. This viral extract, total volume of 1 mL represent 2 combined infection resulting from an inoculum size of $8\times10^4$ pfu ($4\times10^4$ pfu×2) was then titred. Titration was carried out using two indicator cell lines 143B and Vero.

The titration and viral yield results are tabulated in Tables 3 and 4 respectively. VACV-COP did not amplify in the non-permissive CHO cells, i.e., it produced less virus than the amount used in the input inoculum. However, virus amplification in the CHO cell line expressing the host-range gene CP77 was about 2000 times more than the input inoculum (based on titration results using 143B cells as the indicator cell line). Amplification from the permissive cell was about 3000 times more than the input inoculum. Because the standard errors overlap the difference in amplification between the p-LL07-CHO and 143B cells are not statistically significant.

If viral amplification between the two cell lines are compared using the titration results from the Vero indicator cells it would seem amplification was marginally more in the p-LL07-CHO than in the 143B cells, however this was not statistically significant.

In this study it was further confirmed that vaccinia virus is not permissive in CHO cells as the level of viral production was very much less that the amount of virus used as inoculum. However, if CHO express the cowpox virus host range gene encoding CP77 protein, it now becomes permissive to vaccinia virus and support the production of virus to the same levels seen in a permissive cell line. It is also noteworthy that it only required expression of one host range gene, CP77, to convert this cell line into a “usable” permissive cell substrate for the production of vaccinia. Producing vaccinia from CHO is very desirable as CHO is a biotechnology friendly cell line in that it grows as fast as bacteria, it can be cultured in defined synthetic culture medium without the requirement for biological additives such as Foetal Bovine Serum and can be cultured as a cell suspension in bioreactor. CHO also has a history of producing biological medicinal products, has been well characterised and is known and liked by the biomedical control agencies such as FDA and EMEA.

A transgenic CHO cell line expressing the CP77 protein under the control of a constitutive cellular promoter is permissive to vaccinia virus replication and propagation to the same levels seen in a naturally permissive cell line that yields high levels of progeny virus.

Example 5

MVA Propagation in CHO-CP77 Cells

MVA+GFP Propagation in CHO, 143B and p-LL07-CHO

Materials and Methods

Growth Medium (GM): RPMI-1640, supplemented with 10% FBS, 2 mM L-Glutamine, Penicillin and gentamicin, Hepes Maintenance Medium (MM): RPMI-1640, supplemented with 2% FBS, 2 mM L-Glutamine, Penicillin and gentamicin, Hepes Notes on culturing p-LL07-CHO: General propagation and maintenance of the p-LL07-CHO cell line was carried out in GM plus 500 ug/mL of hygromycin B but however, for plating out and culturing to 100% confluency prior to infection, cells were cultured in GM without hygromycin B.

Cell setup: 143B, CHO and P-LL07-CHO cells were seeded into multiple 6-well plates and were cultured in growth medium (GM) at 37° C./5% $CO_2$until the cell monolayers were 100% confluent. One plate per cell line was cultured.

Infection

A recombinant MVA harbouring a GFP expression cassette (green fluorescent protein) was used to infect cells cultured in the 6-well plates. Due to the unknown titre of MVA-GFP, the virus was serially diluted in maintenance medium (MM) as follows:

Dil 1: 20 ul of the stock virus was diluted in 2 ml of MM medium (1:100 dilution) and mixed by vigorous vortexing.

Dil 2: 500 ul of Dil 1 was added to 4.5 ml of MM (1:$10^3$ dilution) and mixed by vigorous vortexing.

Dil 3: 500 ul of Dil 2 was added to 4.5 ml of MM (1:$10^4$ dilution) and mixed by vigorous vortexing.

Dil 4: 500 ul of Dil 3 was added to 4.5 ml of MM (1:$10^5$ dilution) and mixed by vigorous vortexing.

One well of each plate was infected with 500 ul of the following virus dilutions Dil 2, Dil 3, and Dil 4.

Each plate was incubated over a 5 day period and examine for the development and spread of foci of fluorescent cells. In this study, Dil 4 produced discernable foci of fluorescent cells over a three day period. The uninfected wells of each plate were controls for autofluorescence.

Microscope Viewing

The viral infection was viewed under the fluorescent microscope (Olympus IX51) with GFP filter (Cat #U-MG-FPHQ, Olympus). The image was captured using cellSens Digital Imaging Software (Olympus).

Results

The results showed that MVA expressing green fluorescent protein (GFP) does not propagate in CHO and 143B cells as expected. The single cells fluorescing green are the result of virus entering the cell, expressing it’s gene including GFP but unable to produce new infectious viral particles and therefore unable to spread the infection to the neighbouring cells. However, in a CHO cell line expressing CP77, MVA is able to produce new infectious viruses that spreads to the neighbouring cells to form a foci of infection by day 1 post infection with further development by day 3.

Example 6

Confirmation of Host Range Restriction of MVA Harvested from p-LL07-CHO Infection Cell Setup 143B, CHO and BHK-21 cells were seeded into multiple 6-well plates and were cultured in growth medium (GM) at 37° C./5% CO2 until the cell monolayers were 100% confluent. One plate per cell line was cultured.

Virus Harvesting from Example 5

The MVA+GFP from Dil 3 infected P-LL07-CHO well in Example 5 was harvested after 5 days of infection as follows:

- Both supernatant and cells were collected from the well and centrifuge for 5 min at 1000 g to pellet the infected cells.
- The cell pellet was resuspended in 500 ul of 100 mM Tris-HCl pH8 buffer.
- The resuspended cell pellet was freeze and thawed at least three times to release virus from the infected cells.

Infection

- Due to the unknown titre of the crude viral extract the virus was serially diluted in MM medium in the same manner as in Example 5.
- One well of each plate was infected with 500 μl of the following virus dilutions Dil 2, Dil 3, and Dil 4.
- Each plate was incubated over a 5 day period and examine for the development and spread of foci of fluorescent cells. In this experiment, Dil 3 produced discernable foci of fluorescent cells over a three day period.

Microscope Viewing

The viral infection was viewed under the fluorescent microscope (Olympus IX51) with GFP filter (Cat #U-MG-FPHQ, Olympus). The image was captured using cellSens Digital Imaging Software (Olympus).

Results

MVA that was harvested from the CHO cell line expressing CP77 still maintained its restricted host range by not being able to propagate in the non-permissive cells line CHO (hamster) and 143B cell (human). The lack for green fluorescent foci over the three day period post infection of CHO and 143B cells demonstrates that no infectious progeny virus was produced in these cell lines. However, this MVA still maintained its host range for BHK21 cells (hamster) as green fluorescent foci of infection could be seen by day 1 post infection which grew in size over the next 3 days.

Conclusions

- CHO cells expressing the host range protein CP77, are permissive to MVA infections unlike the parental (native) CHO cells.
- MVA that was propagated in a CHO cell line expressing CP77 did not increase its host range to non-permissive cell lines such as CHO and 143B (human).

Example 7

Construction of pLL07

Background Information: CP77 (CHO codon optimised) CDS PCR product from pPH51 DNA template was cloned into pJ507-2 (Hyg+) PiggyBac system by Clontech's InFusion cloning system to create pLL07. The flag-tagged CP77 sequence was inserted into the BsaI of pJ507-2 thereby removing the comet GFP sequence (SEQ ID NO:3).

PCR primer pair used to PCR amplify CP77-CHO gene from pPH51 plasmid DNA:

```
                                        (SEQ ID NO: 4)
AACACGTCTCGGGGGgccgccaccATGTTCGACTACCTGGAAAATGAGGA

AGTG
and

                                        (SEQ ID NO: 5)
CAGGAAGACGCTTTTtcaCTTGTCATCGTCATCCTTGTAATCCTGCTGCT

CGAAGATCTTGTACT.
The Flag Tag sequence is shown in bold in the Inf-
LL07-CP77-Rv primer.
```

The Plasmid INSERT/CASSETTE Configuration is as follows. Insert/Cassette Map. pLL7 clone #3 was sent for sequencing.

15 ABI sequencing files together with the pLL07 reference file "pLL07_ref.sbd" where entered into Lasergene's DNAstar Seqman computer program and assembled into 1 consensus contig. The alignment sequences where trimmed to match the start and end of the reference sequence thereafter the reference sequence was deleted from the alignment so as have no influence on the establishment of the consensus sequence. The consensus sequence of the contig was saved as a DNA sequence file named "pLL07_#3 consensus.seq". The reading direction of the contig was determined and found to represent the same reading direction as the reference sequence. Using Megalign (DNAstar) "pLL07_#3 consensus" was manually aligned to "pLL07_ref.sbd" reference sequence to help identify discrepancies between the reference sequence and the sequence in pLL07_#3. Assembling the 15AB1 files for pLL07Clone#3 from AGRF-sequencing service using Seqman (default settings) resulted in one consensus contig that covered the full length of the pLL07 insertion reference sequence. There was no discrepancy between the sequence in pLL07_#3 and the reference sequence. The insertion sequences in pLL07_#3 contig consensus are identical to the reference sequence.

Example 8

Expression of G1L and I7L in Mammalian Cells

Expression plasmids encoding Flag-tagged-G1L or Flag-tagged-I7L were constructed and used to make transgenic 143B cell lines expressing these proteins. Even though these cells had been amplified in the presence of Geneticin to positively select transduced cells and PCR analysis had confirmed the presence of these protein coding sequences within the genomes of these cell lines, western blot analysis failed to detect the presence of expressed Flag-tagged-proteins when probing with an anti-DDDDK antibody.

The protein coding sequences of C-terminal Flag-tagged COP-G1L and COP-17L where synthesized by GeneArt (Life Technologies) and subcloned into the Bsa I site of pJ503-2 (piggyBac—neomycin antibiotic selection) purchased from DNA2.0 Inc (USA). This cloning procedure exchanges the cometGFP with the Flag-tagged-G1L or -I7L protein coding sequences. The resulting clones were designated pLL08 for the G1 L piggyBac vector and pLL10 for the I7L piggyBac vector.

The key features of these two plasmid vectors are: the flag-tagged protein coding sequences are under the control of constitutive human promoter EF 1 alpha, these expression cassette together with the NPT II expression cassette (neomycin resistance gene) are flanked by Left and Right Transposon borders to form an artificial transposon element. External to the artificial transposon element but contained within the same plasmid is the Transposon enzyme expression cassette that mediates irreversible integration of the transposon element into the host genome. Cells carrying these transposon elements can be positively selected for by including G418 (Geneticin) into the cell growth medium.

The plasmid vector pLL08 (Flag-tagged-G1L) and pLL10 (Flag-tagged-I7L) were transfected into 143B cells to create two transduced transgenic cell lines: G1L-143B (containing the G1L expression cassette), and I7L-143B (containing the I7L expression cassette). Cells with successful transposon integration were amplified to workable amounts by the inclusion of Geneticin in the growth medium. To verify successful integration, total cellular DNA was extracted from these transgenic cells using the DNeasy DNA extraction kit from Qiagen following the instructions from the kit's instruction manual. Extracted DNA was then used as template for PCR amplification reactions using PCR primer pairs specific for PCR amplification of G1L and I7L. Both cell line were positive for the presence of G1L and I7L DNA sequence in their genomes To test for G1L and I7L expression by these cell lines Western blot analysis was carried out by detecting the presence of each Flag-tagged protein using an anti-Flag Tag antibody [M2] conjugated to HRP (anti-DDDDK antibody, Abcam #ab49763). The results of these western blot analysis using total protein extracted from the G1L-143B and I7L-143B cell lines showed that the anti-Flag-tag antibody does not recognise any proteins extracted from 143B as expected and that if can recognise a Flag-tag protein expressed in a Flag-tag-CP77 transgenic CHO cell line (CP77-CHO) confirming the anti-flag-tag antibody can recognise flag-tagged proteins. However, no Flag-tagged-G1L protein could be detected in the protein extract from the G1L-143B sample. Bacterially expressed Flag-tagged-I7L protein can be detected by the anti-Flag-tag antibody but the antibody could not detect Flag-tagged-I7L expression by the I7L-143B cell line.

Since the G1L and I7L expression cassettes could be detected in their respective cell line, the conclusions could be either the expressed proteins are rapidly degraded after synthesis in the absence of a vaccinia infection, i.e., both the G1 and I7 proteins are virus specific enzymes and could be unstable without their vaccinia specific enzyme substrates, or the promoter driving these two expression cassette are defective. Another hypothesis, expression of these proteins in the absence of a vaccinia infection are "toxic" to the cells and during the Geneticin selection process, cells that had silenced the transgenic G1L and I7L expression cassettes but not the NPT II expression cassette enabled the amplification of Geneticin resistant cells that did not expressed the G1L or I7L proteins. Since pJ503-2 piggyBac plasmid has been used successfully in our lab for the expression of COP-D13L in 143B cells it is proposed that the EF1alpha promoter was functional and these proteins were unstable in the absence of a vaccinia infection or the promoter driving the expression of these proteins where selectively silenced to prevent the expression of "toxic" proteins during cell amplification in the presence of Geneticin.

Example 9

D13L As an Example of an Essential Structural Maturation or Assembly Protein is Expressed by Mammalian Cell and Rescues Vaccinia with Deletion of the D13L Gene and D13L Deleted Vaccinia Expresses Protein in Infected Cells Construction of D13-Rescue Cell Line—As an example of attenuating vaccinia by blocking the assembly/maturation process, the D13L ORF of the Copenhagen strain was targeted for deletion. In doing so, a cell line expressing this protein would first have to be constructed so that a COP-D13L-deleted virus can be propagated. For construction of the rescue cell line the Chinese Hamster Ovary cell line, often referred to as CHO, was chosen as this cell line is "biotechnology" friendly. In order to rescue infectious vaccinia virus with a COP-D13L deletion, this cell line must express the D13-protein from its nuclear genome using the transcription machinery of the cell and not of vaccinia virus. The protein amino acid sequence of the cellular expressed D13-protein containing a C-terminal tagged amino acid sequence of DYKDDDDK (Flag-tag, Hopp et al. 1988) and was CHO codon optimized to produce the corresponding nucleotide sequence. Stable integration of this tagged D13L-CHO codon optimised expression cassette consisting of a mammalian promoter and a mammalian poly-adenylation signal sequence into the nuclear DNA was achieved by Transposon integration technology of the type reported by Urschitz et al. 2010 and Matasci et al. 2011. Transduction of CHO was achieved by using the piggy Bac vector system purchased from DNA2.0 Inc (USA).

Construction of D13L protein coding sequence—The D13L protein coding sequence was synthetically made by GeneArt of LifeTechnologies by recreating the DNA sequence from the D13-amino acid encoded by the D13L ORF of the Vaccinia virus Copenhagen strain and codon optimised for expression in CHO cells. The protein coding sequence of the VACV-COP D13L ORF is shown in the Sequence listing.

Construction of D13L cell transducing vector—The codon optimized D13-protein coding sequence (D13LchoTagged) from pLL17 was PCR amplified and subcloned into the transposon piggyBac vector pJ503-2 (pHULK piggyBac Mammalian Expression Vector with CometGFP and Neo+) purchased from DNA2.0 Inc (Cat #pJ503-2) via the Bsa I cloning sites to produce pLL19. Cloning between the BsaI by In-Fusion cloning (Clontech: ligase free cloning) removes the comet GPF coding sequence and replaces it with the tagged D13-protein coding sequence by in vitro homologous recombination. The D13LchoTaggedprotein coding sequence is now under control of the human Elongation Factor 1 alpha promoter (EF1a) and will be co-expressed with the Neomycin resistance gene once both have been stably integrated into the genome of transfected cells. Stable integration into the host genome is mediated by Transposon integration of the DNA sequence bound by the Left and Right Transposon boarder of the piggyBac vector.

PCR amplification of the D13LchoTagged sequence was done using the following primer pair:

```
Forward Primer sequence:
Inf-LL19-D13LC-Fw:
5'-AACACGTCTCGGGGGgccgccaccATGAACAACACCATCATCAA-3'
```

The sequence in uppercase, bold and underline text represent sequence homologous to the Bsa I site up-stream of the comet GFP in pJ503-2 (Neo+) necessary for In-fusion cloning. The sequence in lowercase red and underlined text is a modified Kozak sequence. The sequence in normal uppercase text is homologous to the 5' end of the D13LchoTagged sequence in pLL17.

```
Reverse Primer sequence
Inf-LL19-D13LC-Rv:
5'-CAGGAAGACGCTTTTTCACTTGTCGTCGTCGTCCTTGTAG-3'
```

The sequence in uppercase, bold and underline text represent sequence homologous to the Bsa I site down-stream of the comet GFP in pJ503-2 (Neo+) necessary for In-fusion cloning. The sequence in normal uppercase text is homologous to the 3' end of the D13LchoTagged sequence in pLL17. The expected 1719 bp PCR product was cloned into BsaI cut pJ503-2 (Neo+) by InFusion cloning (Clontech) following the manufacturer's instructions to create pLL19.

Construction of a CHO cell line expressing D13 protein: p-LL19-CHO-CHO cells were seeded into wells of a 6-well plate so that after an overnight incubation they were around 50% confluency. Using the Effectene transfection reagent from Qiagen (Cat #301425), 1 ug of pLL19 was transfected into 1 well of 50% confluent CHO cells following the manufacturer's instructions. The transfected cells were then incubated overnight in growth medium (RPMI 1640/10% FBS/2 mM Glutamax/Pen-Strep). The next day, the medium was changed with growth medium containing 1000 ug/mL Geneticin for selecting transduced cells. The selection medium was changed every 2 to 3 days. When the transduced cells grew to over 90 to 100% confluency, they were recovered using TrypLE Select (Gibco-Invitrogen Corp, Cat #12563-029) and seeded into a T25 flask for further cell expansion.

Verification of D13 expression by Western blotting—Rabbit anti-D13 antisera production: Rabbits were injected with a 16 amino acid peptide linked to KLH protein that represented the C-terminal amino acid of the native D13-protein. This amino acid sequence was: CYDQGVSITKIMGDNN. A total of three injections, 1 month apart, were carried out to raise antibodies to this amino acid sequence. Serum from the injected rabbit were tested by western blot analysis against the following cell extracts: 143B whole cell extract, whole extract from 143B transgenic cell line expressing Flag-tagged-D13L (p-LL06-143b) and VACV-COP infected 143B cell extract. The results clearly demonstrated that the rabbit anti-D13 serum can clearly recognise specifically the D13-protein.

CHO-transduced cell preparation—D13LchoTagged transduced CHO polyclonal expanded cell line (p-LL19-CHO) was cultured to 100% confluency in a T25 flask as was normal CHO cells. Cells from each flask were harvested with TrypLE Select (Gibco-Invitrogen Corp, Cat #12563-029), pelleted by low speed centrifugation (300 g for 5 minutes) washed with PBS and resuspended in 200 uL of PBS.

Western Blot analysis—50 uL of 5×SDS-PAGE loading buffer was added to each cell suspension and then incubated at 98° C. for 5 min. 15 uL of each cell protein extract was loaded into two 10% SDS-PAGE gels, electrophoresed and then blotted onto Hybond ECL nitrocellulose by electroblotting. The electroblotted membranes were then treated with 5% skimmed milk powder dissolved in Tris Buffer Saline containing Tween 20 (TBST) for 1 hour at room temperature to block all available non-specific antibody binding sites on the membrane. Membranes were washed several times in TBST before probing with antibodies. Membrane 1 was probed with 1:5000 dilution of anti-DDDDK tag antibody [M2] conjugated in HRP (Abcam, Cat #ab49763) overnight at 4° C. Membrane 2 was probed with 1:2000 dilution of Rabbit D13-antisera overnight at 4° C., washed 3 times with TBST, and then probed with secondary antibody, 1:5000 dilution of HRP conjugated anti-rabbit antibody (Abcam, Cat #ab97069) for 2 hours. Both membranes were then washed 3 times in TBST and treated with ECL western blotting detection reagents (GE Healthcare) and exposed to X-ray film as instructed by the user manual.

Example 10

Attenuation of VACV-COP by D13L ORF Deletion

To attenuate vaccinia virus, the conserved late promoter sequence together with the majority of the protein coding sequence of the COP-D13L ORF was earmarked for deletion by homologous recombination and in its place, a selection/reporter cassette was inserted so that successful deletion by homologous recombination can be selected for in a CHO cell line expressing D13-protein and where infection can be visualised by red fluorescence. The selection/reporter cassette consist of the CHO host range gene expressing CP77 and the DsRed-Express2 sequence under the control of a vaccinia promoter.

Construction of COP-D13L deletion homologous recombination vector—For deletion of the D13L ORF from VACV-COP by homologous recombination, two homologous recombination arms were design flanking each side of the COP-D13L ORF. However, since the promoter sequence of the COP-D12L ORF might lays within the 3' end of the COP-D13L ORF, approximately 200 bp of the 3' end of COP-D13L ORF was left intact.

Construction of homologous recombination arms F1 and F2—The homologous recombination arms were PCR amplified from VACV-COP genomic DNA using the primer pairs shown below. The bold and underline text represent In-Fusion arms for joining the F1 and F2 arms to the selection/report cassette and the linearized pUC19 supplied in the In-Fusion kit from Clontech. In-Fusion ligation will result in circularized plasmid designated pLL09.

PCR Primer Pair Used to PCR Amplify D13L-F1 Arm from VACV-COP DNA:

```
Inf-PCR-D13L-F1-Fw:
5'CGGTACCCGGGGATCACGAAAAATAATAGTAACCA-3'.
```

The bold and underline text (15 bp) represents sequence homologous to the left end of the linearized pUC19 plasmid supplied by the ClonTech In-Fusion kit.

```
Inf-PCR-D13L-F1-Rv:
5'-AATTTAGTGTGCGCGTGGAAAAAGCTTACAATAAACTC-3'.
```

The bold and underline text (15 bp) represents sequence homologous to the 5' end of the Selection/Reporter cassette. Expected PCR product size: 657 bp PCR Primer Pair Used to PCR Amplify D13L-F2 Arm from VACV-COP DNA:

```
Inf-PCR-D13L-F2-Fw:
5'-ATATTTAAATGCGCGCAATAATGGAACAAGAACCCT-3'.
```

The bold and underline text (15 bp) represents sequence homologous to the 3' end of the Selection/Reporter cassette.

```
Inf-PCR-D13L-F2-Rv:
5'-CGACTCTAGAGGATCGCGCTGAGGTCGGCAACTACG-3'.
```

The bold and underline text (15 bp) represents sequence homologous to the right end of the linearized pUC19 plasmid supplied by the ClonTech In-Fusion kit. Expected PCR product size: 621p Construction of selection/reporter cassette—The selection/reporter expression cassette consist of the CP77 CHO host-range gene from cowpox virus 025L ORF (Brighton Red strain) and the red fluorescent protein coding sequence of DsRed-Express2. This expression cassette was synthetically made by Life Technologies GeneArt so that CP77 protein coding sequence is under the control of its native promoter (100 bp of sequence upstream of the CP77 ATG start codon) and terminated with the poxvirus early transcriptional stop sequence ($T_5NT$). The DsRed protein coding sequence is under the control of a vaccinia virus early/late promoter and also terminated in the poxvirus early transcriptional stop sequence.

Assembly of pLL09—The D13L-F1 and D13L-F2 PCR products together with the Selection/Reporter cassette was assembled into pUC19 supplied in the InFusion Kit from ClonTech by In-Fusion cloning following the manufacturer's instructions to produce pLL09.

Deletion of COP-D13L by homologous recombination and plaque purification to produce SCV104—The COP-D13L ORF was made inactive by deleting the majority of the protein coding sequence and the conserved late promoter element "TAAAT". COP-D13L ORF is under the control of a vaccinia virus late promoter where the conserved late promoter element is critical for promoter activity (Moss, 2007)—deletion of this will result in the COP-D13L ORF becoming silenced. Deletion of the protein coding sequence and conserved promoter element is effected by homologous recombination between VACV-COP and pLL09 where the result of homologous recombination is the insertion of the CP77/DsRed expression cassette into the deleted region. Insertion of this expression cassette enables the recombinant virus, now designated as SCV104, to propagate in CHO cells but only cells that express a functional D13-protein such as p-LL19-CHO. After homologous recombination contaminating "carryover" parental virus (VACV-COP) was eliminated by successive rounds of plaque purification. The presence of contaminating parental virus was monitored for by PCR analysis of the insertion site.

Homologous recombination—Three T25 flasks containing growth medium (RPMI-1640/10% FCS/2 mM Glutamax/Pen-Strep and 1000 ug/mL Geneticin) were seeded with p-LL19-CHO and culture until 100% confluent at 37° C./5% $CO_2$. On the day of infection, two flasks were infected with VACV-COP at an moi 0.01 pfu/cell, where the other flask was not infected (uninfected control). After infecting flask 1 and 2 for 45 min at room temperature, the virus inoculums were removed and the monolayer of cells washed twice with PBS. After washing, 4 ml of Maintenance Medium (MM: RPMI-1640/2% FCS/2 mM Glutamax/Pen-Strep) was added to each flask including flask 3 that had also gone through the same washing step.

Transfection was carried out using Effectene Transfection reagent (Qiagen, Cat No 301425) and following the manufacturer's instructions. Briefly, 16 uL of Enhancer was added to 2 ug of linearized pLL09 in 150 uL of EC buffer and left to stand for 5 minutes at room temperature after thoroughly mixing. To this 25 µl of Effectene Transfection reagent was added and left to stand at room temperature for 10 minutes. Finally, 1 ml of MM (RPMI-1640/2% FCS/2 mM Glutamax/Pen-Strep) was added to the mix and thoroughly mixed gently together. This transfection mix was then added to flask 1 that had previously been infected with VACV-COP.

Flasks 1 (homologous recombination), 2 (infection only control), 3 (uninfected control) were incubated overnight at 37° C./5% $CO_2$ where the following day each flask had a media change with fresh MM—5 mL per flask and further incubated at 37° C./5% $CO_2$ until gross CPE can be seen in Flask 1 only. There should be no signs of infection in Flask 2 as VACV-COP is non-infectious to CHO cells and the monolayer should look healthy in Flask 3.

After the overnight infection red fluorescent cells could be clearly distinguishable under examination with an inverted fluorescent microscope. It was decided to harvest the cells in flask 1 by scraping the cells into the culture medium, then pelleted by low speed centrifugation (500 g for 5 minutes at room temperature) and resuspending the cell pellet in 1 mL of 10 mM Tris-HCl pH8. A viral extract was prepared by multiple freeze and thaw cycles and then stored at −80° C. ready for plaque purification phase. The viral construct was designated SCV 104.

Plaque purification process—The rationale is to serially dilute the homologous recombination extract and use each dilution to infect one row of p-LL19-CHO cells cultured in a 48 well plate. The aim is to dilute the virus down to 1 pfu infection per well and then looking for wells that contain only 1 fluorescent plaque after approx. 30 hr of infection before harvesting.

p-LL19-CHO cells were seeded into each well of a 48-well plate and culture to 100% in growth medium (RPMI-1640/10% FBS/2 mM Glutamax/pen-strep) containing 1000 ug/mL Geneticin at 37° C./5% $CO_2$.

For infection, the homologous recombination extract (SCV104) was thawed and briefly sonicated to break up lumps and aggregates. Ten-fold serial dilution down to $10^{-5}$ of the viral extract was performed using MM (RPMI/2% FBS/Glutamax/PenStrep) in 1 mL volumes. For each dilution, one row of the 48-well plate was seeded with 500 uL of diluted virus after removing the growth medium from each well and washed once with PBS. The 48-well plate was left at room temperature for 45 minute for viral adsorption to occur. After viral adsorption, the virus inoculum was carefully removed from each well where residual inoculum was removed by a washing step consisting of 500 uL of PBS per well. After washing, 500 uL of MM (RPMI/2% FBS/Glutamax/PenStrep) was added to each well and then incubated at 37° C./$CO_2$ until fluorescent red foci of infections can be clearly seen under a fluorescent microscope.

For harvesting only wells containing a single fluorescent foci at the lowest dilution possible was selected. The medium from selected wells were carefully removed and 100 uL of 10 mM TrisHCl pH8 was added. The plate was freeze thawed three times and then the contents of the selected wells were recovered. For each recovered plaque, the plaque purification process was repeat another five times.

A selected clone was then further amplified by infecting 1 well of a 6-well plate containing p-LL19-CHO cells at 100% confluency by removing the growth medium from the well and adding 10 uL of viral extract diluted to 500 uL in PBS. After 45 min at room temperature 2 mL of MM was added to the well and incubated further at 37° C./5% $CO_2$ for 3 days until majority of the cells fluoresce red under a fluorescent microscope. The cells within the infected well were scraped into the culture medium and then pelleted at 500 g for 5 minutes. The pelleted cells were resuspended in 500 uL of 10 mM TrisHCl pH8 and briefly sonicated to make a viral extract.

PCR verification of CP77/DsRed expression cassette insertion into the D13L ORF of SCV104—PCR analysis was carried to determine if after homologous recombination and plaque purification that the D13L ORF had in fact been substituted with the CP77/DsRed expression cassette. A PCR primer pair was designed to bind outside the region of the two flanking homologous recombination arms so that they would bind to "native" DNA sequence rather than "introduced" DNA. Designing the primer pair in such a manner means that this primer pair could use VACV-COP and SCV104 as DNA templates for PCR amplification and the size of the PCR products will be indicative for insertion of expression cassette into the D13L ORF or the detection of the virus with no insertion, i.e., VACV-COP. This PCR assay not only indicates the presence of insertion but also can identify if residual contaminating parental virus (VACV-COP) is still present after multiple rounds of plaque purification. The presence of unwanted trace contamination of VACV-COP is highly undesirable as this contaminant can provide in trans D13 help to SCV104 and thereby reduce the attenuation of SCV104.

DNA extractions using the QIAGEN DNeasy Tissue Kit (Cat #69504)—Viral DNA was extracted from 200 uL of the above SCV 104 amplified virus using the DNeasy Tissue kit following the manufacturer's instruction. Briefly this was done by adding 20 ul of Proteinase K to 200 uL of viral extract and mixing well. To this, 200 ul of buffer AL was added and thoroughly mixed-in before incubating at 56° C. (heating block) for 10 minutes. After incubation, 200 ul of 100% ethanol was added and mixed-in well and then the total volume was added to a spin column. The liquid was passed through the spin column by centrifugation as instructed by the manufacturer's user handbook followed by spin column washes with AW1 and AW2 buffers. DNA bound to the spin column was eluted off with two time 100 uL of AE buffer. The eluted DNA was combined into a single tube and was ready for PCR analysis or stored at 4° C. until ready for PCR analysis.

PCR amplification—DNA extracted from SCV104 (see section 4.2.3.1 above) was used a template for PCR amplification to determine if insertion had taken place within the D13L ORF. The PCR primers describe below binds to sequences flanking outside the D13L ORF so that amplification from SCV104 DNA should amplify a PCR product of 4360 bp as appose to a PCR product of 2881 bp amplified from the parental virus, VACV-COP. PCR analysis showed that the $6^{th}$ plaque purified clones of SCV104 only amplify a product corresponding to greater than 4000 bp less than 5000 bp indicating SCV104 contains CP77/DsRed cassette in the D13L ORF. The lack of a PCR product of around 3000 bp means that there are no detectable levels of parental virus contamination in the SCV 104 amplified stocks.

Details of Primer Pair

```
ID_D12L_LL04_Fw:
5'-TACAAAATCAAATAATGGTCGAAAC-3'

ID_A2L_LL04_Rv:
5'-TGCCAAGAAAACACTCCTTCTAAGACAAT-3'
```

Example 11

Testing SCV104 for Attenuation by Plaque Infectivity Assays

As the protein encoded by the D13L ORF is essential for viral assembly one would expect that cell entry of an SCV104 rescued virus would not be able to produce infectious progeny virions in normal cells permissive for vaccinia virus and hence the inability of the initial infection to spread to neighbouring cells to form an ever expanding foci of infection. To confirm if this is the case, the D13L deleted virus described in this invention (SCV104) was serially diluted to a point where low number of plaque forming units can be used to infect cells cultured in a 6-well plate so that cell to cell spread of the infecting virus can be monitored over a period of days. In this study three cell lines were studied: 143B cell which are permissive to vaccinia virus, CHO cells which are not permissive to vaccinia virus but can be if vaccinia virus express CP77 protein and p-LL19-CHO which is a recombinant cell line expressing D13L protein. The virus describe in this invention which has had a CP77/DsRed expression cassette inserted into the D13L ORF so that no function D13-protein can be expressed should only form infectious foci of infection in the p-LL19-CHO cell line. The presence of foci of infections within the 143B cell monolayer indicates the presence of contaminating vaccinia virus within the viral population mix as the contaminant will be providing D13L help in trans. The presence of foci of infections within the CHO monolayer means that insertion of CP77/DsRed cassette had not inactivated the D13L ORF.

Cell setup—143B, CHO and p-LL19-CHO cells were seeded into multiple 6 well plates and were cultured in growth medium (RPMI-1640/10% FBS/2 mM Glutamax/pen-strep, and only for p-LL19-CHO 1000 ug/mL Geneticin) at 37° C./5% $CO_2$ until the cell monolayers were 100% confluent.

Infection—Amplified $3r^d$ plaque purified viral extract was used to infect the cells. Due to the unknown titre of this virus, 10-fold serially diluted of the stock virus was done to $10^{-4}$ as follows: firstly, 60 ul of stock virus was diluted in 6 ml of MM medium (Dil 1; 1:100 dilution), and then further dilutions prepared by adding 800 ul Dilution 1 to 7.2 ml of MM medium (Dilution 2; $10^{-3}$ dilution), and then repeated to make a $10^{-4}$ dilution. For infection, 500 uL of each dilution was added to each well of a 6-well plate—one plate per cell line used. Viral adsorption was carried out at room temperature for 45 min where after the viral inoculum was removed from each well and each well washed with PBS before MM was added at 2 mL per well. The plates were incubated at 37° C./5% $CO_2$ and observed daily under a fluorescent microscope. $10^{-2}$ dilution produced the best viral infection rate for observation.

Microscopy viewing—The viral infection was viewed under the fluorescent microscope (Olympus IX51) with DsRed filter (Cat #U-MRFPHQ, Olympus). The image was captured using CellSens Digital Imaging Software (Olympus).

Results—$10^{-2}$ dilution infection produced the best results for observing initial single cell infection and the spread of infection to neighbouring cells. Examination of the 143B cell shows the presence of single cell infections at day 1 in which the virus was unable to spread to neighbouring cells by day 2 and day 3 indicating that the virus entry into singles cells had occur but no infectious viral progeny had been produced by day 2 and day 3. The same is true for the CHO single infected cells, i.e., no infectious viral progeny was produced from the initial single cell infections.

Examination of the p-LL19-CHO cell line shows that the initial single cell infection had produced progeny infectious virus as seen as small foci of infection by day 1. These foci of infections had rapidly increase in size by day 2 and day 3 indicating viral amplification is taking place with time.

Accordingly, removal of a functional vaccinia crescent scaffold protein coding sequence from any vaccinia virus will grossly attenuate this virus. Even though this virus is unable to produce infectious progeny virus upon initial infection, expression of its protein, especially the DsRed, does occur in the initial single infected cells as evidence from the visual sight red fluorescence. This virus can be rescued from a cell line expressing the vaccinia crescent scaffold protein independently of the vaccinia virus infection. Constitutive expression of the vaccinia crescent scaffold protein by the transgenic cell line has no adverse effect on the growth or physiology of this cell line.

Example 12

Construction of C11-LL19-HeLa Cell Line Expressing D13L

In order to titrate a non-fluorescent SCV with a D13L deletion, a rescue cell line expressing D13 protein consisting of a vaccinia permissive cell line which supports lytic plaque formation was made. In CHO cells, vaccinia virus expressing CP77 or cell line expression of CP77 does not support lytic plaque formations that can be stained with crystal violet and counted by eye. In order to create a titration cell line, HeLa cells were transduced to express D13 protein by stable integration of an expression cassette consisting of a constitutive mammalian promoter, D13-protein coding sequence containing the Kozak sequence around the start codon and terminating in a polyadenylation signal sequence. This cassette was then cloned into a plasmid vector that enable stable gene transfer into the host cell genomic DNA and selection for successful integration by antibiotic selection. Transduced cells were then amplified by using antibiotic selection to select for cells containing the D13 expression cassette and then a plaque assay carried out with SCV104 (D13L ORF deletion) by infecting monolayers of cells at an moi of 0.001 pfu per cells and selecting for cell-line clone that produced the largest plaque size over a 3 day period. SCV104 has had its D13L ORF replaces with two expression cassette: one for the expression of CP77 protein and the other for expression of a red fluorescent protein. Infection of a HeLa cell line expressing D13 protein with SCV104 will result in red fluorescent lytic plaques.

Construction of pLL19—D13 cell transducing vector: the construction of pLL19 is described above. In this plasmid the C-terminal Flag-tagged D13-protrein coding sequence is under the control the constitutive human Elongation Factor 1 alpha promoter and stable gene transfer into the cellular genomic DNA is mediated by transposition. Transposition also inserts a Neomycin antibiotic selection expression cassette so that transduced cells can be positively selected for by adding G418/Geneticin into the growth medium.

Stable insertion of the D13-Flag tagged expression cassette into HeLa cells by transduction with pLL19: HeLa cells were seeded into a T25 flask, and cultured to approximately 50% confluency in RPMI-1640/10% FBS/2 mM Glutamax/pen-strep growth medium. Using the Effectene transfection reagent from Qiagen (Cat #301425), 1 ug of pLL19 was transfected into the T25 flask of 50% confluent HeLa cells following the manufacturer's instructions. The transfected cells were then incubated overnight in growth medium (RPMI 1640/10% FBS/2 mM Glutamax/Pen-Strep). The next day, the medium was changed to fresh growth medium containing 1000 ug/mL Geneticin for selecting transduced cells. When most of the cells died the remaining cells were recovered by detaching them from the flask surface with TrypLE Select (Gibco-Invitrogen Corp, Cat #12563-029) and single cell sorted into 96-well plates containing growth medium and 1000 ug/mL Geneticin. These plates were incubated at 37° C./5% $CO_2$ until colonies of cells could be seen in each well. The selection medium was changed every 2 to 3 days. Each colony of cells were recovered and serially expanded by culturing in to the following: 48-well plate to 24-well plate to 6-well plate to T75 flask and maintained in T75 flask by 1:5 split ratio until ready for making a frozen cell stock.

Screening for a monoclonal cell line that best support SCV104 plaque formation: SCV104 is a vaccinia virus that has had its D13L ORF replaced with cow poxvirus 025L promoter plus ORF which codes for the CP77 protein, and a red fluorescent protein expression cassette (DsRed Express2). The CP77 expression is not important or needed for plaque formation in HeLa cells but this virus will not propagated in the absence of cell line expression of D13 protein. However, in HeLa cell line expressing D13-protein SCV104 should be able to amplify and spread to other neighbouring cells and in doing so form red fluorescent lytic plaques in the cell monolayer. This virus was used in a plaque formation study in clonal LL19-HeLa cell lines to select the clone that best supports plaque formation.

Cell line setup: a number of cell line clones of LL19-HeLa were seeded into wells of 6 well plates and cultured in growth medium containing 1000 ug/mL Geneticin to 100% confluency at 37° C./5% $CO_2$:

Virus infection: SCV 104 was used to infect the cells at 0.001 pfu per cell by diluting the virus in MM (RPMI-1640/2% FBS/2 mM Glutamax/pen-strep) to $10^3$ pfu/ml. 1 ml of diluted virus was added to each well for infection. Each well of a 6-well plate contains approximately $1\times10^6$ cells when confluent, therefore 1 ml of $10^3$ pfu/ml results in an moi 0.001. An moi of 0.001 will ensure plaque formations from single infected cells. All plates were incubated at room temperature for 1 hour so the virus can adsorb to the cells and there after 1 mL of MM was added to each well and all plates were then incubated at 37° C./5% $CO_2$ promoting synchronous viral entry into cells followed by viral amplification resulting in cell to cell spread over time. Red fluorescent plaque formation was observed daily under a fluorescent microscope.

Microscopy viewing: viral infection and plaque formation over a three day period was viewed under the fluorescent microscope (Olympus IX51) with DsRed filter (Cat #U-MR-FPHQ, Olympus). The image was captured using CellSens Digital Imaging Software (Olympus).

Results: A day 1 post infection all infections resulted in sporadic small foci of red fluorescence. By day 3, all clonal cell lines produced sizable red fluorescent lytic plaque where clone 11 (C11) produced the significantly largest plaque sizes of all clones tested.

Conclusion: These results demonstrate that the C11 clone (C11-LL19-HeLa) was expressing enough D13 protein to support largest plaque formation of all the clones tested from an SCV104 infection. This cell line clone (C11) is excellent for quantifying a D13L deleted vaccinia virus using lytic plaque counting method of titration commonly used to titrate vaccinia virus.

Example 13

Construction of p-LL07-LL29-CHO Cell Line Expressing CP77and D13L

In order to rescue a VACV-COP virus with a D13L ORF deletion in CHO cells, a CHO cell line expressing the D13 and CP77 proteins would have to be constructed. This was done by constructing a D13 mammalian expression cassette and CP77 mammalian expression cassette consisting of a mammalian promoter to drive expression, a CHO preferred codon optimised DNA sequencing coding for the D13 or CP77 proteins followed by a polyadenylation signal sequence. These cassettes where then cloned into plasmid vectors that enable stable gene transfer into the host cell genomic DNA and selection for successful integration by antibiotic selection. Transduced cells were then amplified by using antibiotic selection to select for cells that contain both D13 and CP77 expression cassettes. To verify expression of CP77 a vaccinia virus expressing Enhance Green Fluorescent protein (SCV505) was used to infect the transgenic cell line where fluorescent plaque development was monitor over a 4 day period. Ever expanding green fluorescent plaque size over the 4 day period confirmed CP77 expression by the cell line. To verify expression of D13 protein and a D13L deleted vaccinia virus expressing CP77 (SCV 104) and DsRed fluorescent protein was used to infect the transgenic cell line where plaque development was monitor over a 4 day period. Ever expanding red fluorescent plaque size over the 4 day period confirmed D13 protein expression by the cell line.

Construction of pLL07—CP77 Gene Transfer Plasmid

Construction of CP77 protein coding sequence: the CP77 protein coding sequence was synthetically made by GeneArt GmbH (Germany) by recreating (back translation or reverse translation) the DNA sequence from the amino acid sequence of the CP77 encoded by the 025L ORF of cow poxvirus Brighton Red strain UniProtKB/Swiss-Prot: P12932.1 and codon optimized for expression in Chinese Hamster Ovary (CHO) cells.

Construction of CP77 cell transducing vector: the codon optimized CP77 protein coding sequence from pPH51 (a cloning plasmid harbouring the codon optimized CP77 protein sequence) was PCR amplified using PCR primer pair where the 5' primer was designed to add a Kozak sequence around the start codon and the 3' primer was designed to add the Flag-tag sequence prior to the stop codon. The amplified PCR product was subcloned into the transposon piggybac vector pJ507-2 (Hyg$^+$) purchased from DNA2.0 Inc (USA) via the BsaI cloning site. Cloning into the BsaI sites effectively replaces the cometGFP coding sequence with the CP77 protein coding sequence to create pLL07. The CP77 now becomes under the control of the constitutive human Elongation Factor 1 alpha promoter (EF1a) and is co-expressed with the hygromycin resistance gene once both have been stably integrated into the genome of the transfected cells. Stable integration into the host genome is mediated by Transposon integration of the DNA sequence bound by the Left and Right Transposon boarder of the piggyBac vector.

PCR Primer Pair Used to PCR Amplify CP77-CHO Gene from pPH51 Plasmid DNA:

```
Forward Primer sequence:
                                        (SEQ ID NO: 4)
AACACGTCTCGGGGGgccgccaccATGTTCGACTACCTGGAAAATGAGGA

AGTG

Reverse Primer sequence:
                                        (SEQ ID NO: 5)
CAGGAAGACGCTTTTtcaCTTGTCATCGTCATCCTTGTAATCCTGCTGCT

CGAAGATCTTGTACT.
The Flag Tag sequence is underlined followed by the
stop codon (in lowercase).
```

Construction of pLL29—D13 Gene Transfer Plasmid

The CHO-codon optimized D13 protein coding sequence was PCR amplified from pLL19 (as described previously) to exchange the C-terminal Flag-tag sequence to the HA-tag sequence before cloning into pJ503-02 (pHULK piggyBac Mammalian Expression Vector with CometGFP and Neo+) purchased from DNA2.0 Inc (Cat #pJ503-2) via the Bsa I cloning sites.

Construction of D13L-HA cell transducing vector: the codon optimized D13-protein coding sequence without the C-terminal Flag-tag sequence was PCR amplified from pLL19 and subcloned into the transposon piggyBac vector pJ503-2 (pHULK piggyBac Mammalian Expression Vector with CometGFP and Neo+) purchased from DNA2.0 Inc (Cat #pJ503-2) via the Bsa I cloning sites to produce pLL29. Cloning between the BsaI sites by In-Fusion cloning (Clontech: ligase free cloning) removes the cometGPF coding sequence and replaces it with the newly HA-tagged D13-protein coding sequence by in vitro homologous recombination. The D13LchoHA-Tagged protein coding sequence is now under control of the constitutive human Elongation Factor 1 alpha promoter (EF1a) and will be co-expressed with the Neomycin resistance gene once both have been stably integrated into the genome of transfected cells. Stable integration into the host genome is mediated by Transposon integration of the DNA sequence bound by the Left and Right Transposon boarder of the piggyBac vector. A plasmid map of pLL29 is shown below.

PCR Amplification of the D13Lcho-HA Tagged Sequence was Done Using the Following Primer Pair:

```
Forward Primer sequence:
Inf-LL19-D13LC-Fw:
5'-AACACGTCTCGGGGGGCCGCCACCATGAACAACACCATCATCAA-3'

Reverse Primer sequence:
Inf-LL27-D13L-Rv:
5'-CAGGAAGACGCTTTTttaAGCATAATCTGGAACATCATATGGATAGT

TGTTATCGCCCATGATCT-3'
```

The sequence in underline text represent HA coding sequence. "tta" represents the stop codon Stable double insertion of the CP77-Flag tagged and D13-HA tagged expression cassettes into CHO cells by simultaneous transduction with pLL07 and pLL29

CHO cells were seeded into a T25 flask, and cultured to approximately 50% confluency in RPMI-1640/10% FBS/2 mM Glutamax/pen-strep growth medium. Using the Effectene transfection reagent from Qiagen (Cat #301425), 1 ug of pLL07 and 1 ug of pLL29 were transfected into the T25 flask of 50% confluent CHO cells following the manufacturer's instructions. The transfected cells were then incubated overnight in growth medium (RPMI 1640/10% FBS/2 mM Glutamax/Pen-Strep). The next day, the medium was changed to fresh growth medium containing 500 ug/mL Geneticin and 250 ug/ml Hygromycin B for selecting transduced cells. The selection medium was changed every 2 to 3 days until most of the cells died and detached leaving colonies of cells that were derived from single cells. When the transduced cells grew to over 90 to 100% confluency, they were recovered using TrypLE Select (Gibco-Invitrogen Corp, Cat #12563-029) and seeded into a T75 flask for further cell expansion. This new polyclonal cell line was designated p-LL07-LL29-CHO.

Verification of D13 and CP77 Expression by Rescuing Vaccinia Virus and Vaccinia Virus Deleted of D13L ORF SCV505 is a vaccinia virus that expresses the Enhanced Green Fluorescent Protein (EGFP) and only propagate in CHO cells in the presence of CP77 protein. This virus was used in a plaque infectivity study in p-LL07-LL29-CHO to verify CP77 expression by this cell line. SCV104 is a vaccinia virus that has had its D13L ORF replace with cow poxvirus 025L promoter plus ORF which codes for the CP77 protein, and a red fluorescent protein expression cassette (DsRed Express2). This virus will not propagated in the absence of cell line expression of D13 protein. This virus was used in a plaque infectivity study in p-LL07-LL29-CHO to verify D13 expression by this cell line.

p-LL07-LL29-CHO Cell Line Plaque-Infectivity Study

Various cell lines were used in this study to help qualify the expression of D13 and CP77 by p-LL07-LL29-CHO from infection by SCV505 ($D13^+$ $CP77^-$ $EGFP^+$) and SCV104 ($D13^-$ $CP77^+$ $DsRed^+$). The expected results in the following cells lines are as follows:

Vero: This cell line is normally permissive to vaccinia virus infection. Plaque formation indicating cell to cell spread of amplified virus over time as detected by GREEN fluorescence for SCV505 infection as this virus is normally infectious in this cell line. However, no plaque formation as detected by the lack of or only single cell RED fluorescence for SCV 104 infection should be seen indicating there is no cell to cell spread of amplified virus over time due to the lack of D13 protein expression by cell line or virus.

C11-LL19-HeLa: this is a vaccinia virus permissive cell line expressing D13 protein via pLL19 transduction. Plaque formation from SCV505 infection is expected indicating cell to cell spread of amplified virus over time as detected by GREEN fluorescence regardless of cell line expression of D13. Plaque formation from SCV 104 infection is expected since this virus can now amplify in this cell line due to cell line expression of D13 protein.

CHO: this cell line is non-permissive to vaccinia virus infection. No plaque formation from SCV505 and SCV104 infections is expected to be seen as detected by the lack of or only single cell RED or GREEN fluorescence. This indicates that there is no cell to cell spread of amplified virus over time due to the lack of D13 protein expression by cell line needed to rescue SCV104 event though this virus can express CP77 and the lack of CP77 protein expression by cell line needed to rescue SCV505.

p-LL07-LL29-CHO: this is a CHO cell line expressing both D13 and CP77 proteins. Plaque formation from SCV505 infection is expected indicating cell to cell spread of amplified virus over time as detected by GREEN fluorescence indicates the cell line expression of CP77 protein. Plaque formation from SCV104 is expected indicating cell to cell spread of amplified virus over time as detected by RED fluorescence indicates the cell line expression of D13 protein.

Cell line setups: Vero, CHO, C11-LL19-HeLa, and p-LL07-LL29-CHO cell lines were seeded into two sets of multiple 6 well plates (one for SCV505 infection and the other for SCV104 infection) and were cultured in corresponding growth medium (as follows) to 100% confluency at 37° C./5% $CO_2$:

Vero, CHO: RPMI-1640/10% FBS/2 mM Glutamax/pen-strep

C11-LL19-Hela: RPMI-1640/10% FBS/2 mM Glutamax/pen-strep, plus 1000 ug/mL Geneticin p-LL07-LL29-CHO: RPMI-1640/10% FBS/2 mM Glutamax/pen-strep, plus 500 ug/mL Geneticin and 250 ug/ml Hygromycin B Virus infection: SCV104 and SCV505 were used to infect the cells at 0.001 pfu per cell by diluting the virus in MM (RPMI-1640/2% FBS/2 mM Glutamax/pen-strep) to $10^3$ pfu/ml. One virus per plate: 1 ml of diluted virus was added to each well for infection. Each well of a 6-well plate contains approximately $1\times10^6$ cells when confluent, therefore 1 ml of $10^3$ pfu/ml results moi 0.001. At moi of 0.001 will ensure plaque formations from single infected cells. All plates were incubated at room temperature for 1 hour so the virus can adsorb to the cells and there after 1 mL of MM was added to each well and all plates were then incubated at 37° C./5% $CO_2$ promoting synchronous viral entry into cells followed by viral amplification resulting in cell to cell spread over time. Fluorescent plaque formation was observed daily under a fluorescent microscope.

Microscopy viewing: viral infection and plaque formation over a four day period was viewed under the fluorescent microscope (Olympus IX51) with DsRed filter (Cat #U-MR-FPHQ, Olympus) for SCV104 virus and GFP filter (Cat #U-MGFPHQ, Olympus) for SCV505. The image was captured using CellSens Digital Imaging Software (Olympus).

Results:

Infection of CHO cells with SCV104 and SCV505 at moi of 0.001: at day 1 post infection only sporadic single cell fluorescence could be seen indicating both virus had entered into the cells but have not yet amplified to spread the infection to the neighbouring cells. However, this remained the same progressing from day 2 to day 4 post infection, i.e., only single cell infections seen and no viral spread to neighbouring cells with time.

Infection of Vero cells with SCV104 and SCV505 at moi of 0.001: infection with SCV505 was as expected, tiny plaques formed at day 1 post infection which all increased in size to a point where all the plaques merged into one confluent infection of the cell monolayers by day 4. This indicated the virus amplified from day 1 onwards to spread the infection to completeness by day 4 post infection. However, this is completely different from the SCV104 infection. At day 1 post infection only sporadic single cell fluorescence could be seen which the same remained over the next 3 days. This indicated that SCV 104 was unable amplify and propagate in this cell line as the virus was lacking the D13L ORF and unable to initiate viral assemble after viral genome replication and also this cell line did not express D13 protein to help rescue viral amplification.

Infection of C11-LL19-HeLa cells (HeLa cell line expressing D13 protein) with SCV104 and SCV505 at 0.001: infection with SCV505 was as expected, small plaques formed at day 1 post infection which increased in size to a point where all the plaques merged into one confluent infection of the cell monolayers by day 4. This indicated the virus amplified from day 1 onwards to spread the infection to completeness by day 4 post infection. Infection with SCV104 also produce the same results demonstrating that the D13 protein produced by this cell line complemented for the lack of the D13L ORF in SCV104 and the amount produced by this cell line was enough to support viral amplification and spread of infection comparable to SCV505 which has an intact D13L ORF.

Infection of p-LL07-LL29-CHO cells (CHO cell line expressing D13 and CP77 proteins) with SCV104 and SCV505 at moi 0.001: for both SCV104 and SCV505, tiny foci of infections were observed at day 1 post infection. Over the next 3 days, these foci of infections expanded into ever increasingly larger plaques that eventually merged into confluent infections by day 4 post infection. This demonstrated that CP77 was being expressed as it supported SCV505 amplification and propagation and D13 protein also expressed as it supported SCV 104 amplification and propagation.

Conclusion: These results demonstrate that a CHO cell line expressing CP77 and D13 protein can be used as cell substrate for the production and manufacture of a D13L deleted vaccinia virus. During infection of normal permissive cells a D13L deleted virus would not be able to initiate viral assembly and therefore not complete its infectious life cycle thus making it an excellent viral vaccine delivery vector for human and animal vaccinations in terms of safety. However, this highly attenuated vaccinia vector can be manufactured in the biotechnology friendly CHO cell line if this cell line expresses the CHO host-range protein (CP77) and the missing assembly protein (D13-protein).

Example 14

D13 and CP77 Protein Expression Analysis of p-LL07-LL29-CHO Cell Line by Western Blotting Background Information The D13 and CP77 proteins expressed by p-LL07-LL29-CHO are tagged and can be detected using an antibody that specifically recognises the amino acid tag sequence on the C-terminal ends of D13 and CP77 protein. In the absence of antibodies that specifically recognise D13 and CP77 proteins, western-blot analysis can be carried out using these anti-tag antibodies to confirm expression of D13 and CP77 proteins in the p-LL07-LL29-CHO cell line. The C-terminal end of the D13 protein contains the HA-tag amino sequence of "YPYDVPDYA" where the C-terminal end of the CP77 protein contains the Flag-tag amino sequence of "DYKDDDDK".

Western-Blot Analysis Methodology

The following cell lines were seeded into T75 flasks and were cultured to 100% confluency in growth medium (RPMI 1640/10% FBS/2 mM Glutamax/Pen-Strep) containing the appropriate selection antibiotics: CHO without selection antibiotics, p-LL07-LL29-CHO with 500 ug/mL Geneticin and 250 ug/ml Hygromycin B, p-LL07-CHO with 250 ug/ml Hygromycin B, and C11-LL19-HeLa with 1000 ug/mL Geneticin. The confluent cell monolayer was detached and digested into single cells suspension with TrypLE Select at 37° C. for 10 mins. The cells from each flask was recovered and pelleted by centrifugation at 300 g for 5 minutes and washed twice with PBS. After the final wash the cell pellets were resuspended in 500 uL of PBS. $4^x$ SDS-PAGE loading buffer was added to the protein extract to give a final concentration of $1^x$ and heated at 98° C. for 2 to 3 minutes. The denatured protein samples were electrophoresed through a Biorad Mini-PROTEAN® TGX Stain-Free™ Precast Gel (gradient gel) for 30 to 45 minutes at 200V. After electrophoresis, separated proteins were transferred to nitrocellulose membrane by electroblotting for 1 hour at 100V.

For protein detection the nitrocellulose membrane was incubated in 5% Skim milk powder in PBS for 1 hour at room temperature to block non-specific antibody binding sites. For detection of HA tagged proteins, the membrane was incubated in 1:1000 dilution of Anti-HA HRP conjugated (Abcam Cat #AB1265) in blocking buffer overnight at 4° C. For detection of Flag-tagged proteins a separate electroblotted nitrocellulose membrane was incubated 1:1000 dilution of Anti-Flag HRP conjugated (Abeam Cat #AB49763) in blocking buffer overnight at 4° C. Membranes were then washed three times in PBS, 5 minutes per wash and then incubated in ECL substrate (Thermo Scientific Pierce ECL Western-bot substrate, Cat No 32106) for a couple of minutes before taking the imagine using a BioRad XRS gel doc system.

Results

Detection of D13 protein via HA-tag detection: the anti-HA-tag antibody was able to detect a protein of the expected size from a whole cell protein extract prepared from p-LL07-LL29-CHO but no protein from a whole cell protein extract prepared from CHO cells. This cleared indicated that p-LL07-LL29-CHO was expressing the D13 protein.

Detection of CP77 protein via Flag-Tag: the anti-Flag-tag antibody was able to detect a protein of the expected size from a whole cell protein extract prepared from p-LL07-LL29-CHO and p-LL07-CHO (CHO cell line only expressing CP77) but no protein from a whole cell protein extract prepared from CHO cells. This cleared indicated that p-LL07-LL29-CHO and p-LL07-CHO were expressing the CP77 protein.

Detection of D13 protein via Flag-tag detection: The D13-protein expressed by C11-LL19-HeLa expressed the D13-protein with a C-terminal Flag-tag and when a western blot of the whole cell protein extract made from this cell line the anti-Flag-tag antibody was able to detect a protein of the expected size. This cleared indicated that C11-LL19-HeLa was expressing the D13 protein.

Many modifications will be apparent to those skilled in the art without departing from the scope of the present invention.

TABLE A

Summary of sequence identifiers

| SEQUENCE ID NO: | DESCRIPTION |
|---|---|
| 1 | Nucleotide sequence of CP77 codon optimised for expression in mammalian cells (CHO) |
| 2 | Amino acid sequence of CP77 encoded by SEQ ID NO: 1 |
| 3 | Nucleotide sequence of pLL07 |
| 4 | Forward primer for CP77-CHO gene from pPH51 plasmid |
| 5 | Reverse primer for CP77-CHO gene from pPH51 plasmid |
| 6 | Nucleotide sequence of vaccinia Copenhagen K1L gene (extract from Genbank M35027.1) |
| 7 | Amino acid sequence of vaccinia Copenhagen K1L (extract from Genbank M35027.1) encoded by SEQ ID NO: 6 |
| 8 | VACV-COP-D13L-ORF |
| 9 | Nucleotide sequence encoding SEQ ID NO: 1 codon optimised for hamster cell expression with C-terminal flag-tag (DYKDDDK) |
| 10 | Forward primer of Inf-LL19-D13LC |

TABLE A-continued

| Summary of sequence identifiers | |
|---|---|
| SEQUENCE ID NO: | DESCRIPTION |
| 11 | Reverse primer of Inf-LL19-D13LC |
| 12 | Flag-tag protein |
| 13 | D13L protein peptide |
| 14 | Forward primer of Inf-PCR-D13L-F1 |
| 15 | Reverse primer of Inf-PCR-D13L-F1 |
| 16 | Forward primer of Inf-PCR-D13L-F2 |
| 17 | Reverse primer of Inf-PCR-D13L-F2 |
| 18 | CP77 + DsRed expression cassette 2903bp |
| 19 | CP77 + DsRed expression cassette |
| 20 | Forward primer of ID_D12L_LL04 |
| 21 | Reverse primer of ID_A2L_LL04 |
| 22 | pLL09 Homologous recombination vector for the deletion of VACV-COP D13L with CP77/DsRed selection |
| 23 | pLL19 Tagged-D13L-CHO codon optimised transposon mediated transducing vector for stable integration into cellular nuclear genomic DNA |

TABLE 1

| Titration Results | | | |
|---|---|---|---|
| | 24 h | 48 h | 72 h |
| CHO | 53 pfu/mL | 0 | 0 |
| Vero | $8.5 \times 10^2$ pfu/mL | $14.25 \times 10^6$ pfu/mL | $27.7 \times 10^6$ pfu/mL |

Viral Yields (Output)

The amount of virus used for infection (Input) was $4\times10^4$ pfu/mL. For comparison sake, yields are expressed as $10^4$ values. Values present average yield per time point, i.e., yield from 3 mL harvest (6 mL divided by 2 wells).

| | 24 h | 48 h | 72 h |
|---|---|---|---|
| CHO | $0.0159 \times 10^4$ pfu | 0 | 0 |
| Vero | $0.255 \times 10^4$ pfu | $4275 \times 10^4$ pfu | $8310 \times 10^4$ pfu |

Production Yield (Output/Input Ratio)

The table below shows the yield of virus produced above the input level from each cell line at each harvest time point, i.e., OUTPUT/INPUT ratio.

| | 24 h | 48 h | 72 h |
|---|---|---|---|
| CHO | 0.004 | 0 | 0 |
| Vero | 0.06 | 1069 | 2078 |

TABLE 2

| Titration results in pfu/mL | | | |
|---|---|---|---|
| Virus/Cell line | Dil | Count | Titre |
| VACV-COP/CHO | $10^{-1}$ | 0 | 0 pfu/mL |
| | | 0 | |
| | | 0 | |
| | | 0 | |
| | Average | 0 | |
| VACV-COP/Vero | $10^{-7}$ | 2 | $2.8 \times 10^7$ pfu/mL +/− 34% |
| | | 2 | |
| | | 4 | |
| | | 3 | |
| | Average | 2.8 | |

TABLE 2-continued

| Titration results in pfu/mL | | | |
|---|---|---|---|
| Virus/Cell line | Dil | Count | Titre |
| VACV-PH22/Vero | $10^{-6}$ | 8 | $0.75 \times 10^7$ pfu/Ml +/− 43% |
| | | 5 | |
| | | 12 | |
| | | 5 | |
| | Average | 7.5 | |
| VACV-PH22/CHO | $10^{-7}$ | 6 | $7.3 \times 10^7$ pfu/mL +/− 20% |
| | | 9 | |
| | | 8 | |
| | | 6 | |
| | Average | 7.3 | |

Average Virus Output from Infection per Well (Yield)

Virus extract volume per flask was 1 mL. Plating volume for titration was 1 mL. Therefore, virus yield equals the titration in pfu/mL multiplied by 1 mL (plating volume).

| Virus | Cell line | Yield per flask |
|---|---|---|
| VACV-COP | CHO | 0 pfu |
| | Vero | $2.8 \times 10^7$ pfu |
| VACV-PH22 | Vero | $0.75 \times 10^7$ pfu |
| | CHO | $7.3 \times 10^7$ pfu |

Yield per pfu Inoculum, i.e., Total pfu Produced from 1 pfu Inoculum

| Inoculum size per flask: $1 \times 10^5$ pfu | | |
|---|---|---|
| Virus | Cell line | Yield per pfu inoculum |
| VACV-COP | CHO | 0 pfu/input pfu |
| | Vero | 280 pfu/input pfu (280 pfu produced for every pfu used for inoculation) |
| VACV-PH22 | Vero | 75 pfu/input fpu (75 pfu produced for every pfu used for inoculation) |
| | CHO | 730 pfu/input pfu (730 pfu produced for every pfu used for inoculation) |

TABLE 3

| This is the titration of each 1 mL viral extract. | | | | | | |
|---|---|---|---|---|---|---|
| | Indicator Cell line | | | | | |
| Cell | 143B | | | Vero | | |
| substrate | Titration pfu/mL | SE | % SE | Titration pfu/mL | SE | % SE |
| CHO | 5.38E+03 | 5.74E+02 | 10.70% | 7.25E+02 | 2.17E+02 | 30.00% |
| p-LL07-CHO | 1.88E+08 | 2.45E+07 | 13.10% | 3.95E+07 | 1.13E+07 | 28.50% |
| 143B | 2.73E+08 | 3.95E+07 | 14.50% | 3.73E+07 | 5.45E+06 | 14.60% |

TABLE 4

Table 4 provides the total amount of virus in each 1 mL viral extract.

| | Indicator Cell line | | | |
|---|---|---|---|---|
| | 143B | | Vero | |
| Cell substrate | Yield pfu | SE | Yield pfu | SE |
| CHO | 5.38E+03 | 5.74E+02 | 7.25E+02 | 2.17E+02 |
| p-LL07-CHO | 1.88E+08 | 2.45E+07 | 3.95E+07 | 1.13E+07 |
| 143B | 2.73E+08 | 3.95E+07 | 3.73E+07 | 5.45E+06 |

TABLE B

| Strain | ORF | Genome | Protein |
|---|---|---|---|
| Copenhagen | COP-D13L | M35027 | AAA48114 |
| Lister clone 107 | List-114 | DQ121394 | ABD52596 |
| LC16mO | mO-149L | AY678277 | AAW23819 |
| LC16m8 | M8-149L | AY678275 | AAW23537 |
| WR | WR-118 | NC_006998 | YP_233000 |
| Dryvax-3737 | VACV-114 | DQ377945 | ABD57648 |
| Acambis-2000 | VACAC2_129 | AY313847 | AAR17961 |
| Acambis Clone 3 | VACCL3-129 | AY313848 | AAQ93215 |
| CVA | CVA-124 | AM501482 | CAM58288 |
| Tiantan Clone 10 | TT10-148 | JX489137 | AGJ91839 |

TABLE B-continued

| Strain | ORF | Genome | Protein |
|---|---|---|---|
| Cowpox Virus GRI-90 strain | CPXV-GRI-E13L | X94355 | CAD90667 |
| Cowpox Virus Brighton Red | CPXV-131 | NC_003663 | NP 619914 |

BIBLIOGRAPHY

Altschul et al. (1997) *Nucleic Acids Research* 25:3389-3402

Ausubel et al. (1999) Current Protocols in Molecular Biology (Supplement 47), John Wiley & Sons, New York Boshart et al. (1985) *Cell* 41:521

Brooks et al. (1995) *J. Virol.* 69(12):7688-7698

Dijkema et al. (1985) *EMBO J.* 4:761

Drillien R, et al. (1978) *J Virol.* 28(3):843-50

Gorman et al., (1982) *Proc. Natl. Acad. Sci. USA* 79:6777

Ham R G. (1965) *Proc. Natl. Acad. Sci. USA* 53: 288-293

Hsiao J C, et al. (2006) *J. Virol.* 80(15):7714-28

Kibler et al. (2011) *PLOSONE* 6(11)

Meisinger-Henschel et al. (2007) *J. Gen. Virol.* 88(12):3249-3259

Murphy et al. (1995) Virus Taxonomy Springer Verlag:79-87

Puck T T, et al. (1958) *J. Exp. Med.* 108:945-956

Sambrook et al. (1989) Molecular Cloning: A Laboratory Manual, 2nd ed., Cold Spring Harbor Press, Plainsview, N.Y.

Shisler et al. (2004) *J. Virol.* 78(7):3553-3560

Spehner D, et al. (1988) *J Virol.*, 62(4):1297-1304

Werden S J, et al. (2008) Chapter 3: Poxvirus Host Range Genes. In: Advances in Virus Research, 71

The invention claimed is:

1. A modified Chinese Hamster Ovary (CHO) cell in which the genome of the CHO cell is modified to comprise a sequence encoding CP77 under the control of a constitutive promoter such that the modified CHO cell line sustains propagation of a vaccinia virus and wherein the genome of the modified CHO cell further comprises a sequence encoding D13L under the control of a constitutive promoter and/or a sequence encoding K1L under the control of a constitutive promoter; with the proviso that CP77, D13L and K1L do not include functional orthologs and functional variants.

2. The modified CHO cell of claim 1, wherein the genome of the modified CHO cell comprises a sequence encoding D13L under the control of a constitutive promoter and a sequence encoding K1L under the control of a constitutive promoter.

3. The modified CHO cell of claim 1, wherein the CHO cell is a continuous CHO cell line.

4. The modified CHO cell of claim 1, wherein expression of the CP77 gene supports a virus replication amplification ratio of more than 500.

5. The modified CHO cell of claim 1, wherein the CP77 is encoded by a contiguous sequence of nucleotides codon optimised for expression in CHO cells.

6. A process for propagating a vaccinia virus in CHO cells, the process comprising propagating the vaccinia virus in vitro in a Chinese Hamster Ovary (CHO) cell wherein the CHO cell is modified to encode and express CP77 under the control of a constitutive promoter and to encode and express D13L under the control of a constitutive promoter; with the proviso that CP77 and D13L do not include functional orthologs and functional variants.

7. The process of claim 6, wherein the CHO cell is modified to encode and express K1L under the control of a constitutive promoter; with the proviso that K1L do not include functional orthologs and functional variants.

8. The modified CHO cell of claim 1, wherein the genome of the modified CHO cell comprises a sequence encoding D13L under the control of a constitutive promoter.

9. The modified CHO cell of claim 1, wherein the genome of the modified CHO cell comprises a sequence encoding K1L under the control of a constitutive promoter.

* * * * *